(12) United States Patent
Yang et al.

(10) Patent No.: US 11,180,509 B2
(45) Date of Patent: Nov. 23, 2021

(54) THIAZOLIDONE SPIRO PYRIMIDINE TRIONE COMPOUND, PREPARATION METHOD THEREFOR AND USES THEREOF

(71) Applicant: SHANGHAI INSTITUTE OF MATERIA MEDICA, CHINESE ACADEMY OF SCIENCES, Shanghai (CN)

(72) Inventors: Yushe Yang, Shanghai (CN); Yinyong Zhang, Shanghai (CN); Chenghui Shi, Shanghai (CN); Qian Chen, Shanghai (CN)

(73) Assignee: SHANGHAI INSTITUTE OF MATERIA MEDICA, CHINESE ACADEMY OF SCIENCES, Shanghai (CN)

( * ) Notice: Subject to any disclaimer, the term of this patent is extended or adjusted under 35 U.S.C. 154(b) by 92 days.

(21) Appl. No.: 16/625,391

(22) PCT Filed: Jun. 21, 2018

(86) PCT No.: PCT/CN2018/092147
§ 371 (c)(1),
(2) Date: Dec. 23, 2019

(87) PCT Pub. No.: WO2018/233663
PCT Pub. Date: Dec. 27, 2018

(65) Prior Publication Data
US 2021/0079019 A1 Mar. 18, 2021

(30) Foreign Application Priority Data
Jun. 22, 2017 (CN) .......................... 201710481447.9

(51) Int. Cl.
C07D 498/22 (2006.01)
A61P 31/04 (2006.01)

(52) U.S. Cl.
CPC ............ *C07D 498/22* (2013.01); *A61P 31/04* (2018.01)

(58) Field of Classification Search
CPC .............................. C07D 498/22; A61P 31/04
See application file for complete search history.

(56) References Cited

U.S. PATENT DOCUMENTS

| | | | | |
|---|---|---|---|---|
| 8,658,641 | B2 * | 2/2014 | Barvian ............... | C07D 498/22 514/233.2 |
| 8,889,671 | B2 * | 11/2014 | Basarab ............ | A61K 31/5383 514/229.5 |
| 2016/0130281 | A1 | 5/2016 | Basarab et al. | |
| 2018/0169104 | A1 | 6/2018 | Huband | |

FOREIGN PATENT DOCUMENTS

| | | |
|---|---|---|
| CN | 102245605 A | 11/2011 |
| CN | 105229012 A | 1/2016 |
| CN | 106659725 A | 5/2017 |
| WO | 2018/233670 A1 | 12/2018 |

OTHER PUBLICATIONS

Lima et al., Current Medicinal Chemistry, (2005), v12, p23-49.*
Extended European Search Report corresponding to EP 18821069.4 dated Oct. 6, 2020; 7 pages.
Alm, Richard A. et al., "Characterization of the Novel DNA Gyrase Inhibitor AZD0914: Low Resistance Potential and Lack of Cross-Resistance in *Neisseria gonorrhoeae*," *Antimicrobial Agents and Chemotherapy* (Mar. 2015) 59(3):1478-1486.
English Translation of the International Search Report corresponding to PCT/CN2018/092147 dated Sep. 13, 2018; 4 pages.
Basarab, G. S. et al., "Discovery of Novel DNA Gyrase Inhibiting Spiropyrimidinetriones: Benzisoxazole Fusion with N-Linked Oxazolidinone Substituents Leading to a Clinical Candidate (ETX0914)," *Journal of Medicinal Chemistry* (Jul. 9, 2015) 58(15):6264-6282.

* cited by examiner

*Primary Examiner* — Yong L Chu
(74) *Attorney, Agent, or Firm* — Mintz Levin Cohn Ferris Glovsky and Popeo PC

(57) ABSTRACT

Disclosed in the present invention are a thiazolidone spiro pyrimidine trione compound, a preparation method therefor and uses thereof, the compound having a structure represented by formula (I). In the formula, the definitions of the substituents are described in the specification and the claims. The thiazolidone spiro pyrimidine trione compound in the present invention has high in vivo and in vitro antibacterial activity, has better metabolic properties, and is obviously superior to existing compounds of the same kind.

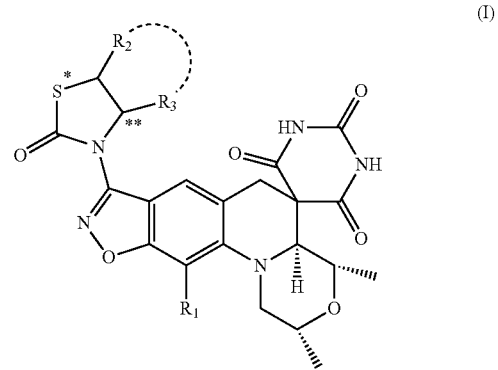

10 Claims, No Drawings

THIAZOLIDONE SPIRO PYRIMIDINE TRIONE COMPOUND, PREPARATION METHOD THEREFOR AND USES THEREOF

TECHNICAL FIELD

The invention relates to a benzoisoxazole spiro pyrimidine trione compound containing thiazolidone, a pharmaceutical composition thereof, a preparation method therefor, and uses in an anti-infective drug.

TECHNICAL BACKGROUND

With the widespread use of antibacterial drugs, the problem of bacterial resistance to existing antibacterial drugs has become increasingly prominent. A series of drug-resistant pathogens represented by multidrug-resistant *Staphylococcus aureus* (MRSA) have seriously threatened human health. In the past 20 years, although some new antibacterial drugs with new mechanisms of action such as linezolid, telithromycin, daptomycin, fidaxomicin, oritavancin, and pleuromutilin topical preparations have entered into the market and effectively alleviated the dilemma when no drug is available for severe infectious diseases caused by multi-drug resistant bacteria such as MRSA, there is still an urgent need in clinic for new antibacterial drugs with novel structure, unique mechanism of action, and effectiveness on drug-resistant bacteria.

Spiro pyrimidine trione compounds are a class of bacterial DNA gyrase/topoisomerase inhibitors having a new mechanism of action. Although these antibacterial compounds and quinolone antibacterials belong to bacterial type II topoisomerase inhibitors, their specific action sites and mechanisms are completely different. Spiro pyrimidine trione compounds have a new mechanism of action and a novel chemical structure type that are different from any existing clinical antibacterial drugs. They have good antibacterial activity against sensitive and resistant Gram-positive bacteria as well as Gram-negative bacteria with better membrane permeability, and there is no cross-resistance with existing clinical antibacterial drugs including fluoroquinolones.

The early structure-activity relationship studies of spiro pyrimidine trione compounds mainly focused on the mono- and poly-substitution of the benzene ring, the modification of the amide nitrogen atom and the morpholine ring of the spiro ring moiety, and the fused ring derivatives reported by AstraZeneca in recent years. These early derivatives have certain bone marrow toxicity and genotoxicity, thereby limiting their further development into useful drugs. A new class of benzoisoxazole spiro pyrimidine trione compounds containing oxazolidinone in side chain overcome these shortcomings, and one representative compound AZD0914 is undergoing Phase II clinical research.

However, these compounds generally have defects such as weak antibacterial activity in vivo and in vitro, unsatisfactory metabolic properties, insufficient drug exposure, etc., so that it is necessary to use a very high dose to meet the requirements. The doses of AZD0914 in Phase II clinical studies are 2 grams and 3 grams.

There is still a need in the art to provide a new class of benzoisoxazole spiro pyrimidine trione compounds having stronger antibacterial activity in vivo and in vitro and better metabolic properties.

SUMMARY OF THE INVENTION

The object of the present invention is to provide a benzoisoxazole spiro pyrimidine trione compound with better activity and better metabolic properties, an enantiomer, diastereomer, racemate and mixtures thereof, and a pharmaceutically acceptable salt thereof.

In the first aspect of the present invention, it provides a compound represented by the general formula I, or an enantiomer, a diastereomer, a racemate and a mixture thereof, or a pharmaceutically acceptable salt thereof,

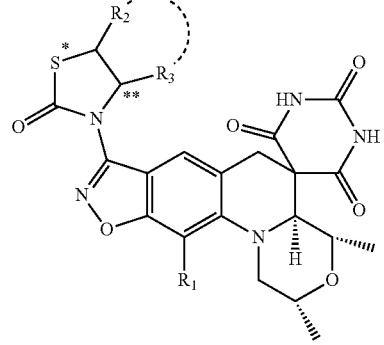

(I)

wherein, $R_1$ is hydrogen, halogen or cyano;

$R_2$ and $R_3$ are each independently hydrogen, phenyl, substituted or unsubstituted $C_1$-$C_6$ alkyl, or =$CH_2$, and the term "substituted" refers to a substitution with a substituent selected from the group consisting of $C_1$-$C_6$ alkoxy, phenyl, halogen, —$N_3$, —$S(O_2)C_1$-$C_6$ alkyl, —$NHCOC_1$-$C_6$ alkyl, —$CONHC_1$-$C_6$ alkyl, —$OR_4$, $C_1$-$C_6$ alkylthio, $C_2$-$C_6$ alkenyl, $C_2$-$C_6$ alkynyl; or $R_2$, $R_3$ and the attached carbon atoms together form a 4-7 membered aliphatic ring;

$R_4$ is hydrogen, or $C_1$-$C_6$ haloalkyl;

\* and \*\* each independently represent a racemic, S-type or R-type.

The general formula (I) of the present invention indicates that the compound contains at least three chiral centers, and there are enantiomers and diastereomers. For enantiomers, two enantiomers can be obtained by general chiral resolution or asymmetric synthesis. Diastereomers can be separated by fractional recrystallization or chromatographic separation. The compound represented by general formula (I) of the present invention includes any of the above isomers or a mixture thereof.

In another preferred embodiment, $R_1$ is fluorine, chlorine or cyano.

In another preferred embodiment, $R_2$ is hydrogen, phenyl, substituted or unsubstituted $C_1$-$C_4$ alkyl, or =$CH_2$, wherein the term "substituted" refers to a substitution with a substituent selected from the group consisting of halogen, —$OR_4$, $C_1$-$C_4$ alkoxy, —$N_3$, —$NHCOC_1$-$C_4$ alkyl, —$S(O_2)$ $C_1$-$C_4$ alkyl; $R_4$ is hydrogen or $C_1$-$C_4$ haloalkyl;

$R_3$ is hydrogen, substituted or unsubstituted $C_1$-$C_4$ alkyl, or phenyl, wherein the term "substituted" refers to a substitution with a substituent selected from the group consisting of: phenyl;

or $R_2$ and $R_3$ together with the attached carbon atoms form a 5-6 membered aliphatic ring.

In another preferred embodiment, $R_2$ is hydrogen, phenyl, substituted or unsubstituted $C_1$-$C_3$ alkyl, or =$CH_2$, and the term "substituted" refers to a substitution with a substituent selected from the group consisting of fluorine, chlorine, —$OR_4$, $C_1$-$C_3$ alkoxy, —$N_3$, —$NHCOC_1$-$C_3$ alkyl, —$S(O_2)$ $C_1$-$C_3$ alkyl; $R_4$ is hydrogen or trifluoromethyl;

$R_3$ is hydrogen, $C_1$-$C_3$ alkyl, phenyl, or benzyl;

or $R_2$ and $R_3$ together with the attached carbon atoms form a 5-6 membered aliphatic ring.

In another preferred embodiment, at most one of $R_2$ and $R_3$ is hydrogen; or $R_2$ and $R_3$ together with the attached carbon atoms form a 5-6 membered aliphatic ring.

In another preferred embodiment, at least one of $R_2$ and $R_3$ is hydrogen; or $R_2$ and $R_3$ together with the attached carbon atoms form a 5-6 membered aliphatic ring.

In another preferred embodiment, $R_4$ is hydrogen or trifluoromethyl.

In another preferred embodiment, the compound is:

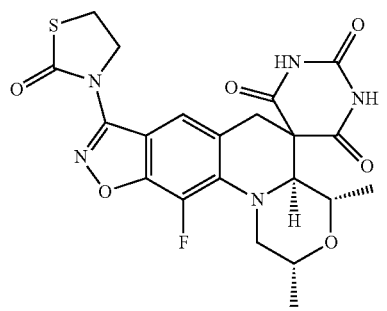

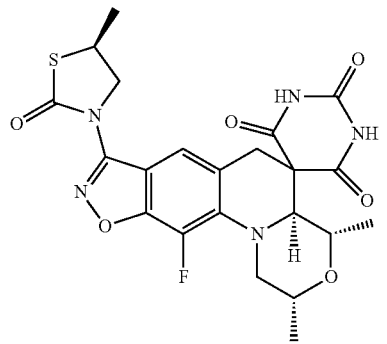

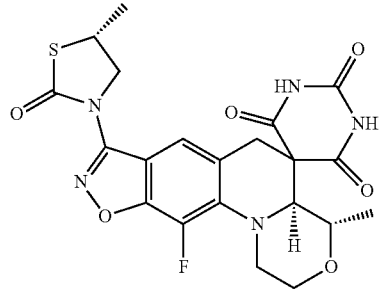

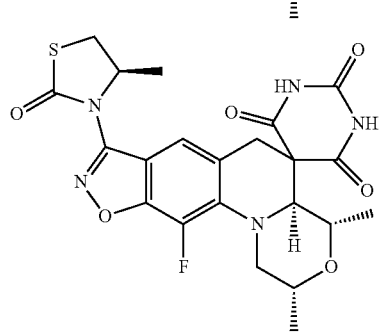

-continued

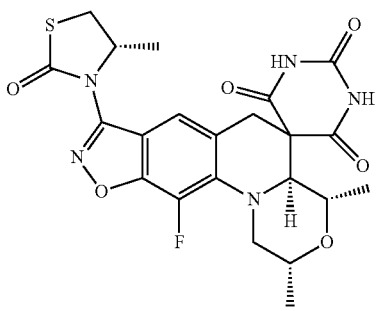

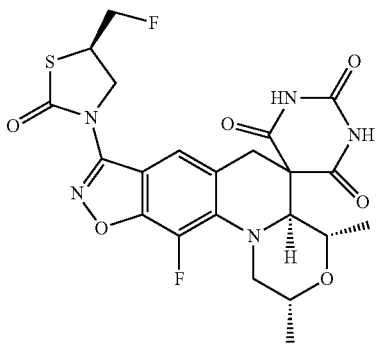

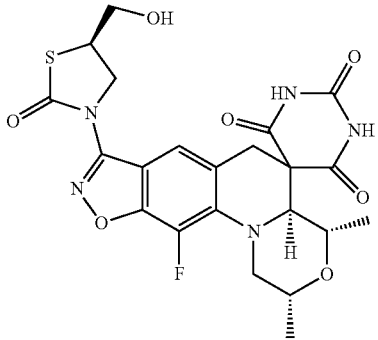

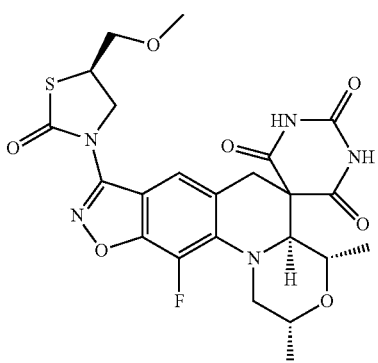

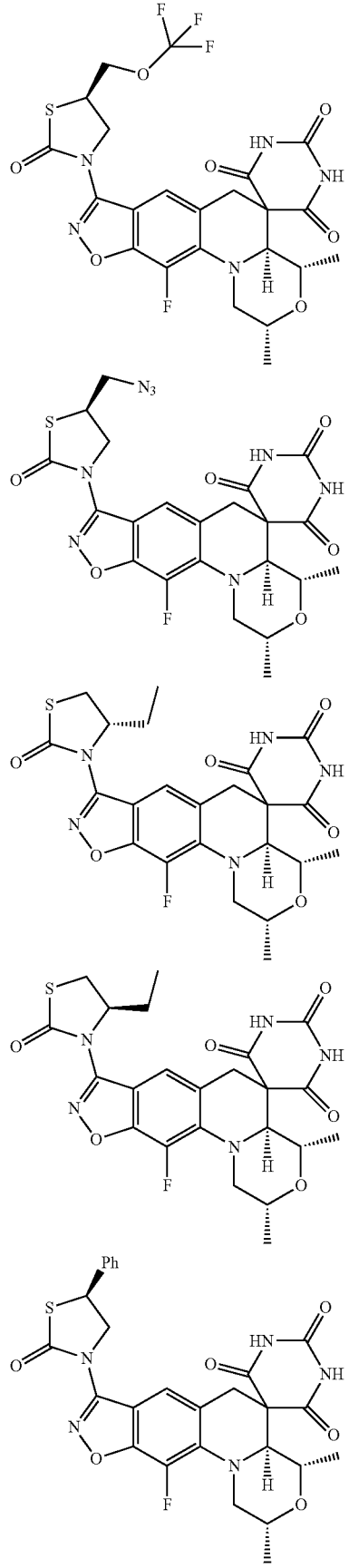
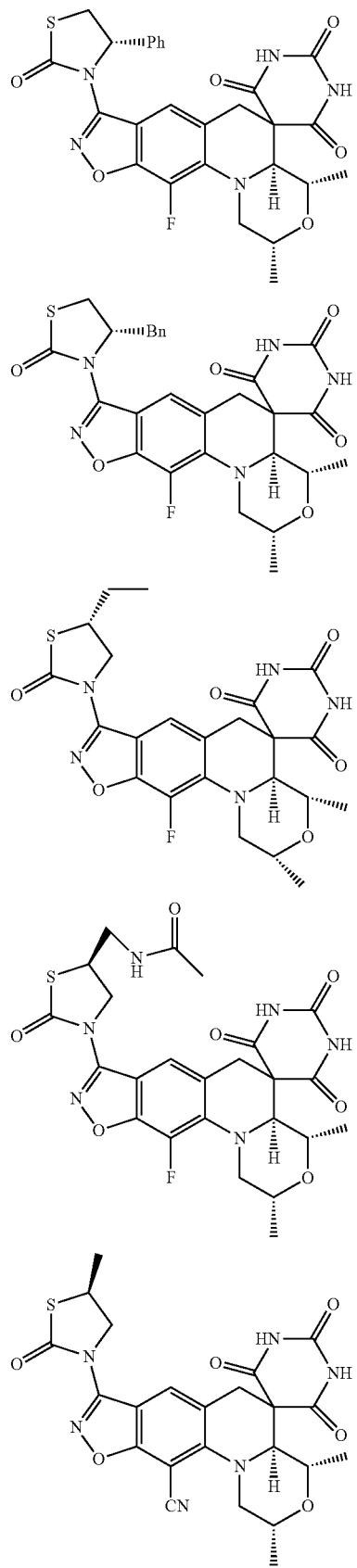

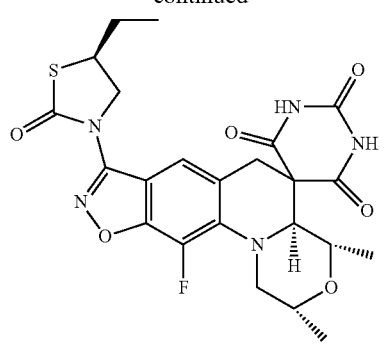
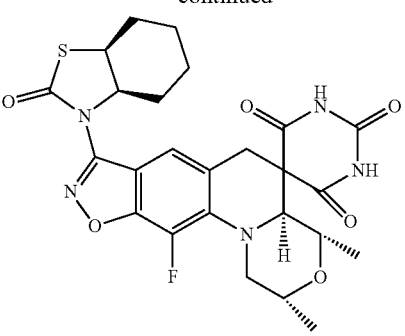
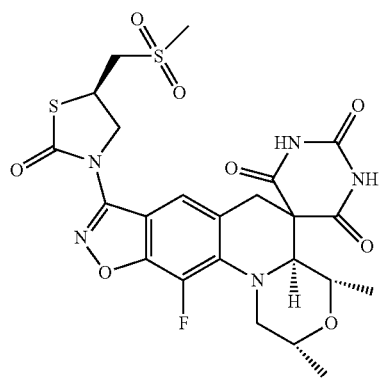
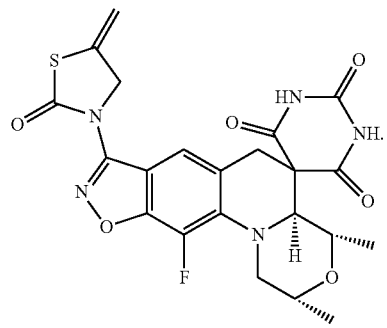
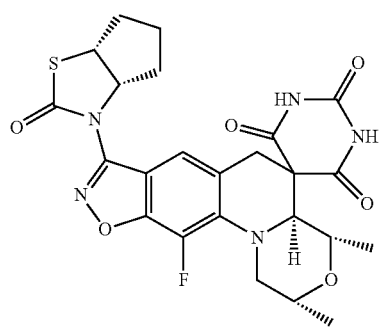
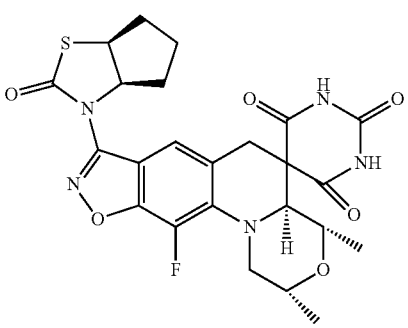
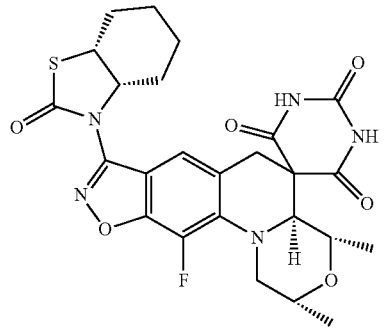
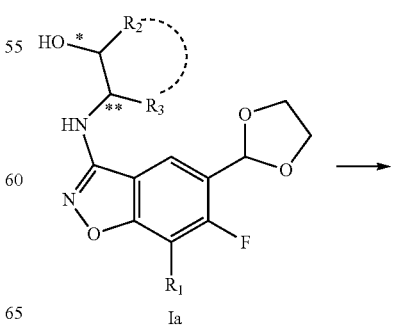

In the second aspect of the present invention, it provides a pharmaceutical composition comprising the compound or enantiomer, diastereomer, racemate and mixture thereof, or pharmaceutically acceptable salt thereof in the first aspect; and a pharmaceutically acceptable carrier or excipient.

The invention provides a novel benzoisoxazole spiro pyrimidine trione compound, which can be used alone, or is mixed with pharmaceutically acceptable excipients (such as excipients, diluents, etc.) and formulated into tablets, capsules, granules or syrups for oral administration. The pharmaceutical composition can be prepared according to a conventional method in pharmaceuticals.

In the third aspect of the present invention, it provides a method for preparing the compound in the first aspect, comprising the following steps:

-continued

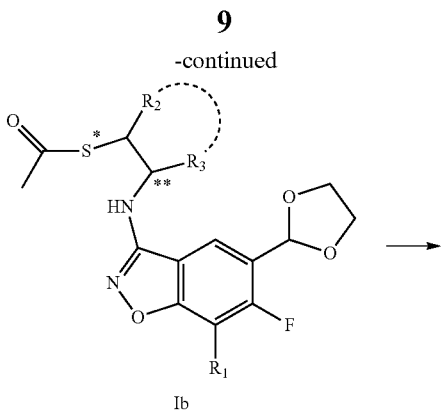

Ib

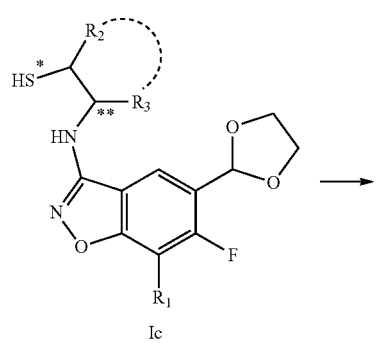

Ic

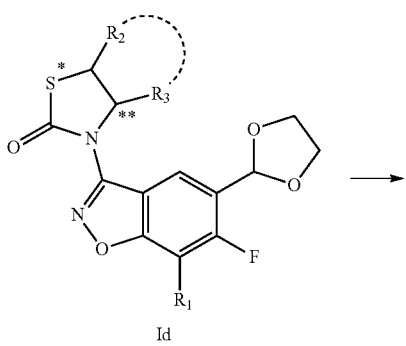

Id

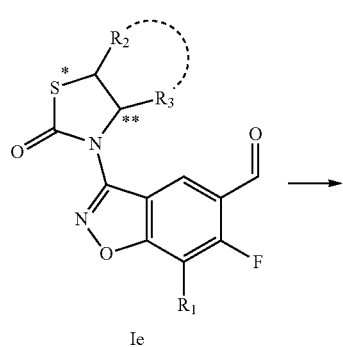

Ie

-continued

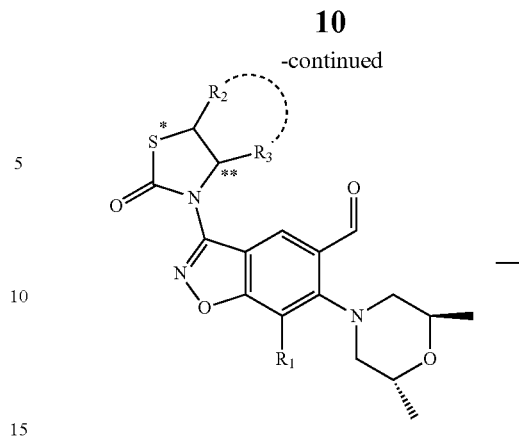

If

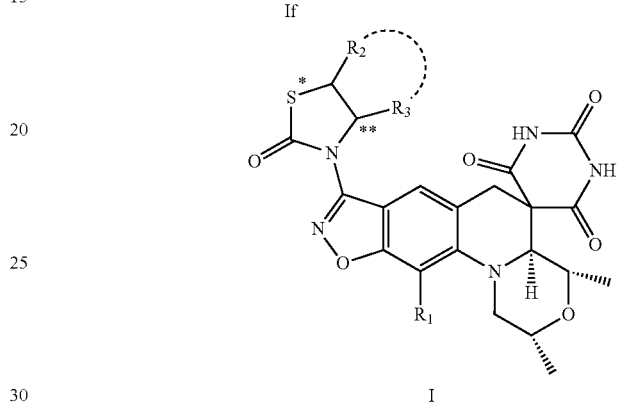

I (i) subjecting an intermediate Ia and thioacetic acid to Mitsunobu reaction, thereby forming an intermediate Ib;

(ii) subjecting the intermediate Ib and sodium hydroxide to hydrolysis reaction, thereby forming an intermediate Ic;

(iii) subjecting the intermediate Ic and N,N'-carbonyldiimidazole to nucleophilic substitution reaction, thereby forming an intermediate Id;

(iv) subjecting the intermediate Id and hydrochloric acid to a deprotection reaction, thereby forming an intermediate Ie;

(v) subjecting the intermediate Ie and 2R,6R-dimethylmorpholine to nucleophilic substitution reaction, thereby forming an intermediate If;

(vi) reacting the intermediate If with barbituric acid, thereby forming a compound represented by formula I, in each formula, *, **, $R_1$, $R_2$, and $R_3$ are defined as above.

In another preferred embodiment, the intermediate Ia is reacted with thioacetic acid via Mitsunobu reaction to form the intermediate Ib.

In another preferred embodiment, the intermediate Ib and sodium hydroxide are subjected to a hydrolysis reaction to form the intermediate Ic.

In another preferred embodiment, the intermediate Ic and N, N'-carbonyldiimidazole undergo a nucleophilic substitution reaction to form the intermediate Id.

In another preferred embodiment, the intermediate Id is reacted with hydrochloric acid to remove the protective group to form the intermediate Ie.

In another preferred embodiment, the intermediate Ie and 2R,6R-dimethylmorpholine undergo a nucleophilic substitution reaction to form an intermediate If.

In the fourth aspect of the present invention, it provides a use of the compound or enantiomer, diastereomer, racemate and mixture thereof, or a pharmaceutically acceptable salt thereof in the first aspect or a use of the pharmaceutical composition in the second aspect for preparation of a medicament for treating a bacterial infectious disease.

In another preferred embodiment, the infectious disease is an infectious disease caused by a multidrug-resistant bacterium.

In another preferred embodiment, the infectious disease is an infectious disease caused by Gram-positive bacterium.

In another preferred embodiment, the multidrug-resistant bacterium is selected from the group consisting of MRSA, MSSA, MRSE, MSSE, PRSP and Spy.

In the fifth aspect of the present invention, it provides a method for inhibiting bacteria in vitro, comprising administering to a subject or the environment the compound or enantiomer, diastereomer, racemate and mixture thereof, or a pharmaceutically acceptable salt thereof in the first aspect or the pharmaceutical composition in the second aspect.

In the sixth aspect of the present invention, it provides an intermediate of a compound of formula I, the structure of which is represented by Formula Ia, Ib, Ic, Id, Ie or If:

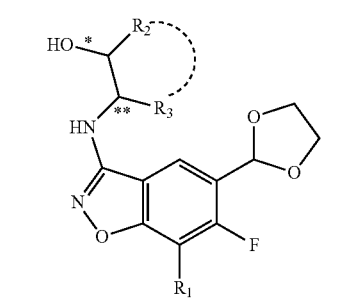

Ia

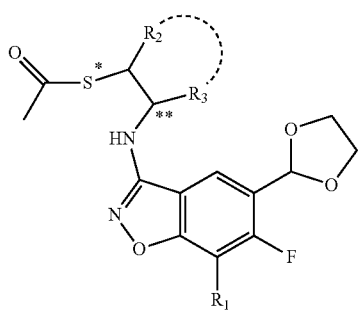

Ib

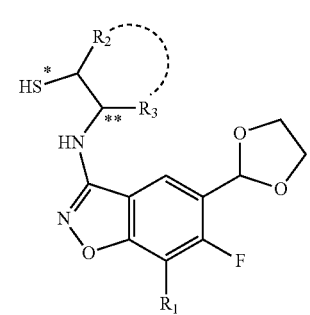

Ic

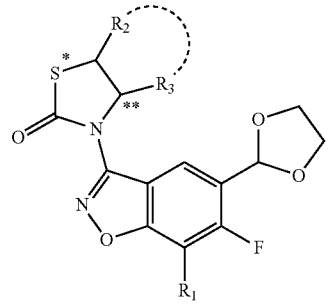

Id

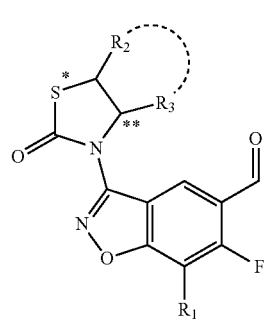

Ie

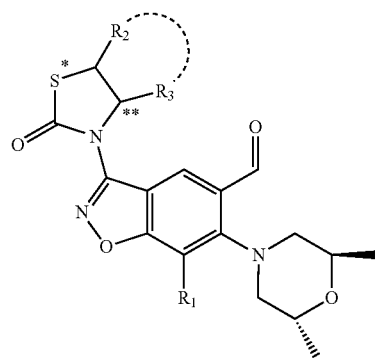

If in each formula, $R_1$, $R_2$, and $R_3$ are defined as above.

The compound of the present invention has much better antibacterial activity in vitro and in vivo and drug metabolism properties than AZD0914, and is very suitable as a novel antibacterial medicine for the antibacterial treatment of human or animal infections.

It should be understood that above each technical feature and each technical feature specifically described hereinafter (as in the examples) within the scope of the present invention may be combined with each other to constitute a new or preferred technical solution. Each feature disclosed in the description may be replaced by any alternative feature serving the same, equivalent, or similar purpose. Due to space limitations, those will not be repeated herein one by one.

DESCRIPTION OF EMBODIMENTS

After extensive and intensive research, the inventors of the present application have firstly developed a class of benzoisoxazole spiro pyrimidine trione compounds having novel structure. It is found that they have much better antibacterial activity in vitro and in vivo and drug metabolism properties than AZD0914, and are very suitable as a novel antibacterial drug for the antibacterial treatment of human or animal infections. Based on this, the present invention has been completed.

Terms

In the present invention, the term "$C_1$-$C_6$ alkyl" refers to a linear or branched alkyl having 1 to 6 carbon atoms, and includes, without limitation, methyl, ethyl, propyl, isopropyl, butyl and the like; and the term "$C_1$-$C_4$ alkyl" has a similar meaning. The term "$C_2$-$C_6$ alkenyl" refers to a linear or branched alkenyl with one double bond having 2 to 6 carbon atoms, and includes but is not limited to vinyl, propenyl, butenyl, isobutenyl, pentenyl and hexenyl. The term "$C_2$-$C_6$ alkynyl" refers to a straight or branched alkynyl having 2 to 6 carbon atoms and containing a triple bond, including, without limitation, ethynyl, propynyl, butynyl, isobutynyl, pentynyl and hexynyl. The term "$C_1$-$C_6$ haloalkyl" refers to an alkyl substituted with one or more halogen atoms, such as —$CH_2F$, —$CF_3$, —$CH_2CHF_3$, and the like.

In the present invention, the term "$C_1$-$C_6$ alkoxy" refers to a straight or branched alkoxy having 1 to 6 carbon atoms, and includes, without limitation, methoxy, ethoxy, propoxy, isopropoxy, butoxy and the like; and the term "$C_1$-$C_4$ alkoxy" has a similar meaning.

In the present invention, the term "4- to 7-membered aliphatic ring" refers to a cycloalkyl having 4 to 7 carbon atoms on the ring, and includes, without limitation, cyclobutyl, cyclopentyl, cyclohexyl, cycloheptyl and the like; and the term "5- to 6-membered aliphatic ring" has a similar meaning.

The "pharmaceutically acceptable salt" includes a pharmaceutically acceptable base addition salt, which includes, but is not limited to, a salt of inorganic base such as sodium salt, potassium salt, calcium salt, magnesium salt and the like, and includes, but is not limited to, a salt of organic base such as ammonium salt, triethylamine salt, lysine salt, arginine salt, and the like. These salts can be prepared by methods known in the art.

Preparation Method

The compound represented by the general formula (I) of the present invention can be prepared by the following method, but the conditions of the method, such as the reactant, solvent, base, amount of the compound used, reaction temperature, reaction time, etc. are not limited to the following explanations. The compounds of the present invention can also be conveniently prepared by optionally combining various synthetic methods described in this specification or known in the art, and such combinations can be easily performed by those skilled in the art to which the present invention belongs.

Route 1

In a preferred embodiment, compounds 1-5, compounds 11-16, compound 19, and compounds 21-24 are prepared according to route 1.

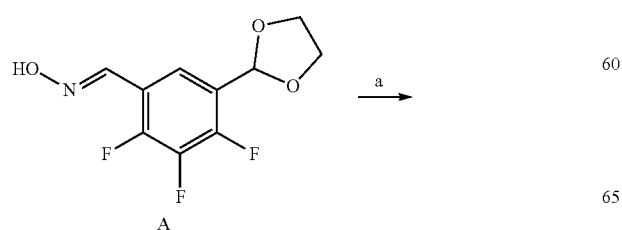

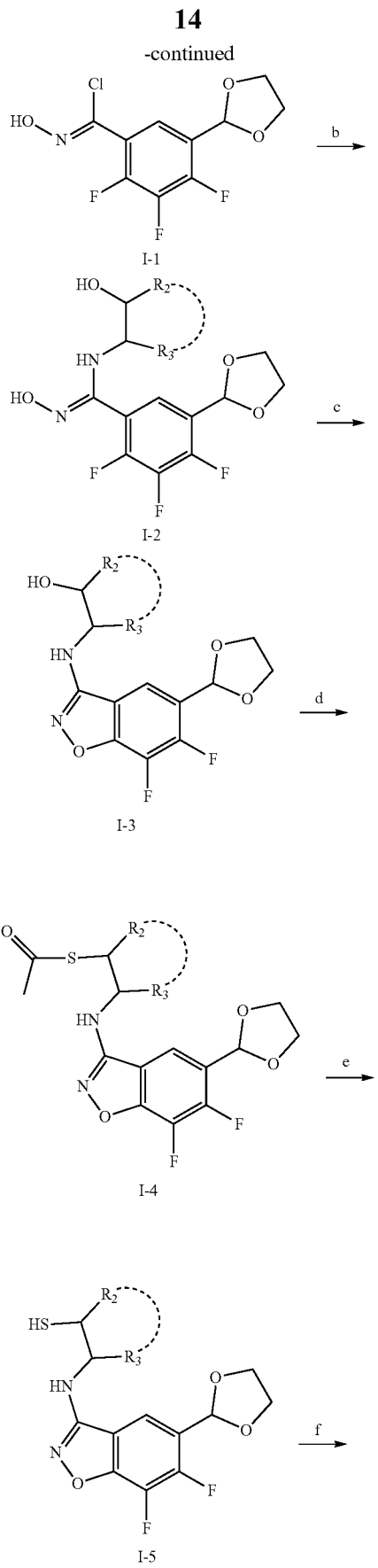

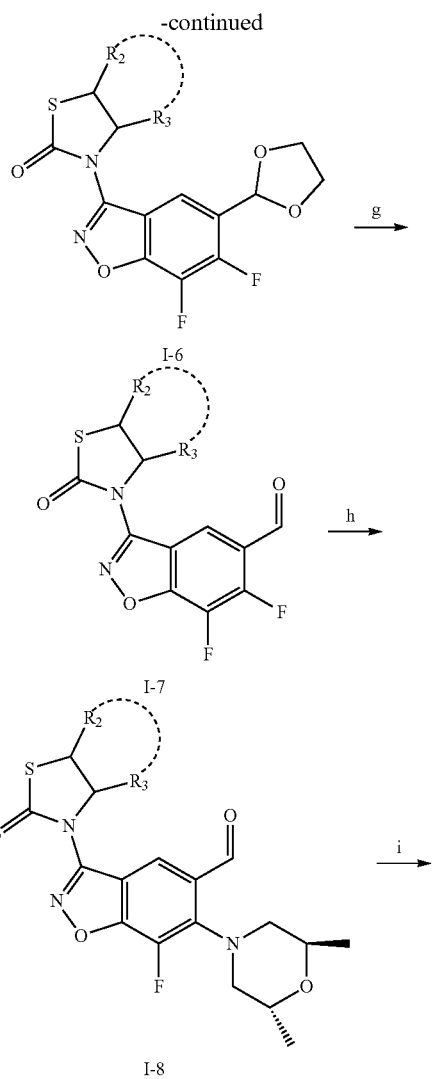

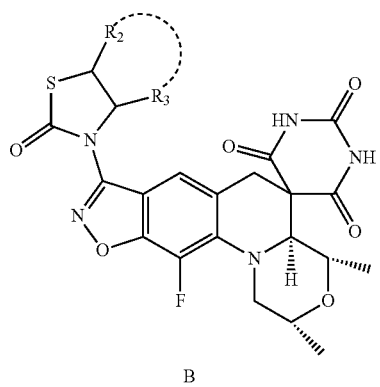

b. The intermediate I-1 is reacted with different primary amines respectively in polar aprotic solvents at 0° C. for 30 min to form a corresponding intermediate I-2 via nucleophilic substitution. The primary amines are various primary amines that meet the requirements and the polar aprotic solvent may be 1,4-dioxane, toluene, tetrahydrofuran, or dimethylformamide (DMF).

c. The intermediate I-2 is reacted in a polar aprotic solvent at 60° C. for 4 h (hours) in the presence of cesium carbonate to generate a corresponding intermediate I-3. The polar aprotic solvent may be 1,4-dioxane, toluene, tetrahydrofuran, or dimethylformamide (DMF).

d. The intermediate I-3 is reacted with thioacetic acid in the presence of an active intermediate formed by diisopropyl azodicarboxylate and triphenylphosphine in a polar aprotic solvent at room temperature for 2 h, thereby forming a corresponding intermediate I-4. The polar aprotic solvent may be 1,4-dioxane, toluene, tetrahydrofuran, or dimethylformamide (DMF).

e. The intermediate I-4 is reacted in the presence of sodium hydroxide and dithiothreitol in a solvent at 0° C. for 1 h to form a corresponding intermediate I-5. The solvent may be methanol, ethanol, 1,4-dioxane, tetrahydrofuran, or dimethylformamide (DMF).

f. The intermediate I-5 is reacted with N,N'-carbonyldiimidazole under the catalysis of 4-dimethylaminopyridine in a polar aprotic solvent at 80° C. for 4 h to generate a corresponding intermediate I-6. The polar aprotic solvent may be 1,4-dioxane, toluene, tetrahydrofuran, or dimethylformamide (DMF).

g. The intermediate I-6 and hydrochloric acid are reacted in a solvent at room temperature for 2 h to form a corresponding intermediate I-7. The solvent may be 1,4-dioxane, tetrahydrofuran, or dimethylformamide (DMF).

h. The intermediate I-7 is reacted with 2R,6R-dimethylmorpholine in the presence of an organic base in a polar aprotic solvent at 90° C. for 15 hours to form a corresponding intermediate I-8. The organic base may be triethylamine or N,N-diisopropylethylamine, and the polar aprotic solvent may be acetonitrile, 1,4-dioxane, tetrahydrofuran, or dimethylformamide (DMF).

i. The intermediate I-8 is reacted with barbituric acid in a mixed solvent of acetic acid and water at 110° C. for 5 hours to form the corresponding compound B.

Route 2

In a preferred embodiment, compound 6 is prepared according to route 2.

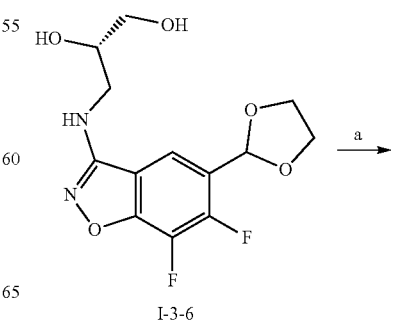

$R_2$ and $R_3$ are defined as above.

a. An intermediate A [J. Med. Chem, 2015, 58 (15): 6264-6282.] is reacted with N-chlorosuccinimide in a polar aprotic solvent at 10-60° C. for 20-60 minutes to obtain an intermediate I-1. The polar aprotic solvent may be 1,4-dioxane, toluene, tetrahydrofuran, or dimethylformamide (DMF). The optimal reaction temperature is room temperature and the optimal reaction time is 30 min.

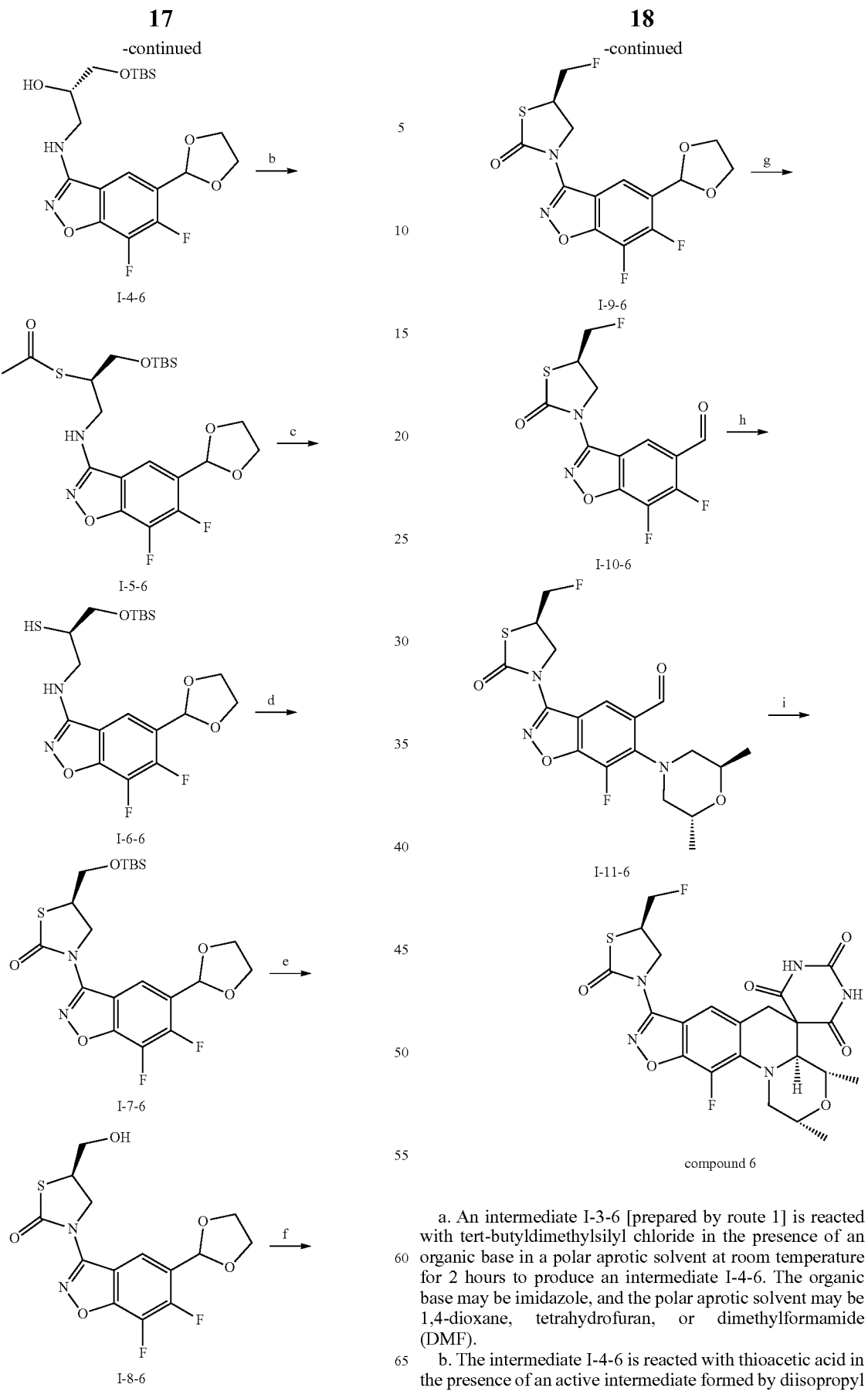

a. An intermediate I-3-6 [prepared by route 1] is reacted with tert-butyldimethylsilyl chloride in the presence of an organic base in a polar aprotic solvent at room temperature for 2 hours to produce an intermediate I-4-6. The organic base may be imidazole, and the polar aprotic solvent may be 1,4-dioxane, tetrahydrofuran, or dimethylformamide (DMF).

b. The intermediate I-4-6 is reacted with thioacetic acid in the presence of an active intermediate formed by diisopropyl azodicarboxylate and triphenylphosphine in a polar aprotic solvent at room temperature for 2 h to form a corresponding intermediate I-5-6. The polar aprotic solvent may be 1,4-dioxane, toluene, tetrahydrofuran, or dimethylformamide (DMF).

c. The intermediate I-5-6 is reacted in the presence of sodium hydroxide and dithiothreitol in a solvent at 0° C. for 1 h to form an corresponding intermediate I-6-6. The solvent can be methanol, ethanol, 1,4-dioxane, tetrahydrofuran, or dimethylformamide (DMF).

d. The intermediate I-6-6 is reacted with N,N'-carbonyldiimidazole under the catalysis by 4-dimethylaminopyridine in a polar aprotic solvent at 80° C. for 4 h to form a corresponding intermediate I-7-6. The polar aprotic solvent may be 1,4-dioxane, toluene, tetrahydrofuran, or dimethylformamide (DMF).

e. The intermediate I-7-6 is reacted with tetrabutylammonium fluoride in a polar aprotic solvent at 0° C. for 10 minutes to form an intermediate I-8-6. The polar aprotic solvent can be 1,4-dioxane, toluene, tetrahydrofuran, or dimethylformamide (DMF).

f. The intermediate I-8-6 is reacted with diethylamino sulfur trifluoride in a polar aprotic solvent at 35° C. for 1 h to form an intermediate I-9-6. The polar aprotic solvent may be 1,4-dioxane, toluene, tetrahydrofuran, or dimethylformamide (DMF).

g. The intermediate I-9-6 and hydrochloric acid are reacted in a solvent at room temperature for 2 h to form a corresponding intermediate I-10-6. The solvent may be 1,4-dioxane, tetrahydrofuran, or dimethylformamide (DMF).

h. The intermediate I-10-6 is reacted with 2R,6R-dimethylmorpholine in the presence of an organic base in a polar aprotic solvent at 90° C. for 15 h to form a corresponding intermediate I-11-6. The organic base may be triethylamine or N,N-diisopropylethylamine, and the polar aprotic solvent may be acetonitrile, 1,4-dioxane, tetrahydrofuran, dimethylformamide (DMF).

i. The intermediate I-11-6 is reacted with barbituric acid in a mixed solvent of acetic acid and water at 110° C. for 5 h to form the corresponding compound 6.

Route 3

In a preferred embodiment, compound 7 is prepared according to route 3.

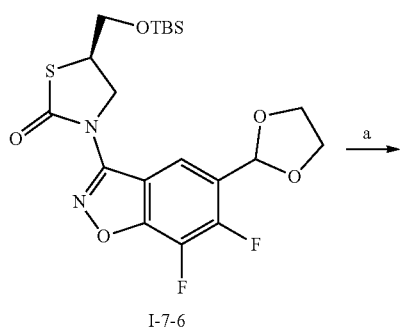

I-7-6

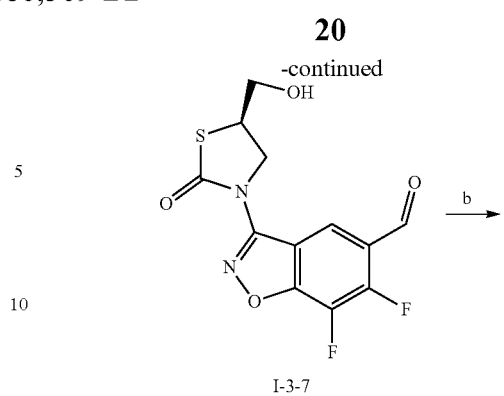

I-3-7

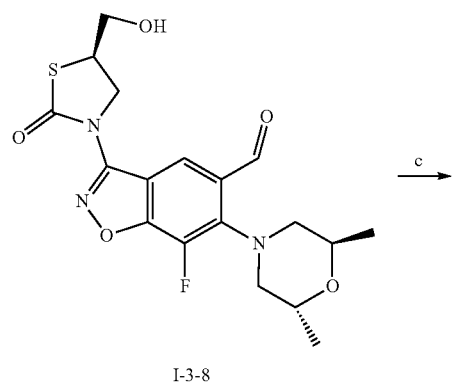

I-3-8

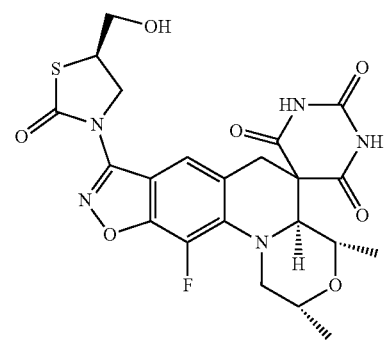

compound 7 a. An intermediate I-7-6 and hydrochloric acid are reacted in a solvent at room temperature for 2 h to form an intermediate I-3-7. The solvent may be 1,4-dioxane, tetrahydrofuran, or dimethylformamide (DMF).

b. The intermediate I-3-7 is reacted with 2R,6R-dimethylmorpholine in the presence of an organic base in a polar aprotic solvent at 90° C. for 15 h to form an intermediate I-3-8. The organic base may be triethylamine or N,N-diisopropylethylamine, and the polar aprotic solvent may be 1,4-dioxane, tetrahydrofuran, or dimethylformamide (DMF).

c. The intermediate I-3-8 is reacted with barbituric acid in a mixed solvent of ethanol and hydrochloric acid at 100° C. for 5 hours to form the corresponding compound 7.

Route 4

In a preferred embodiment, compound 8 is prepared in according to route 4.

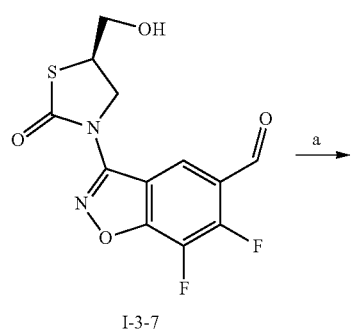

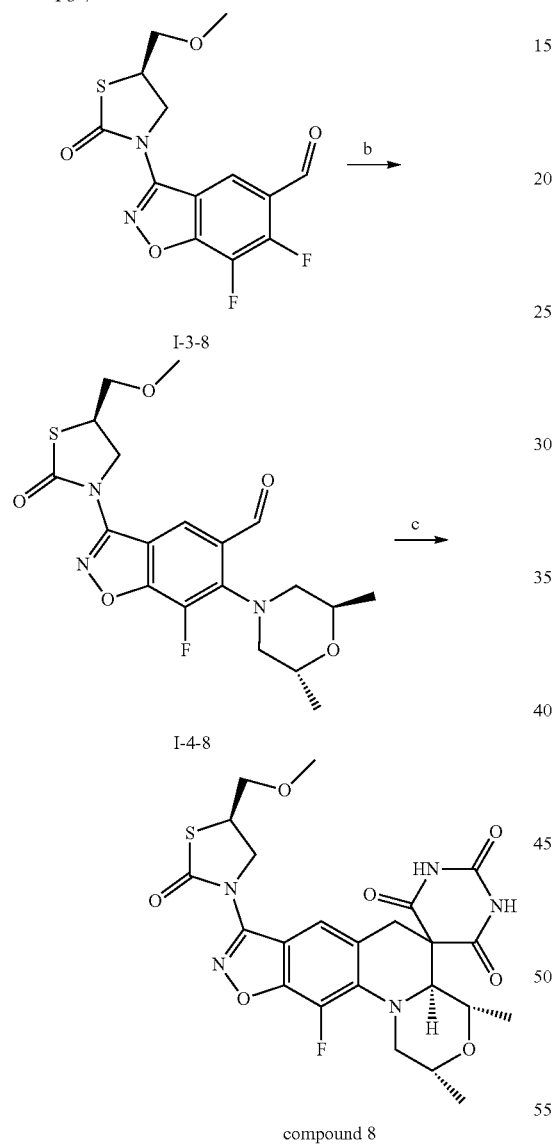

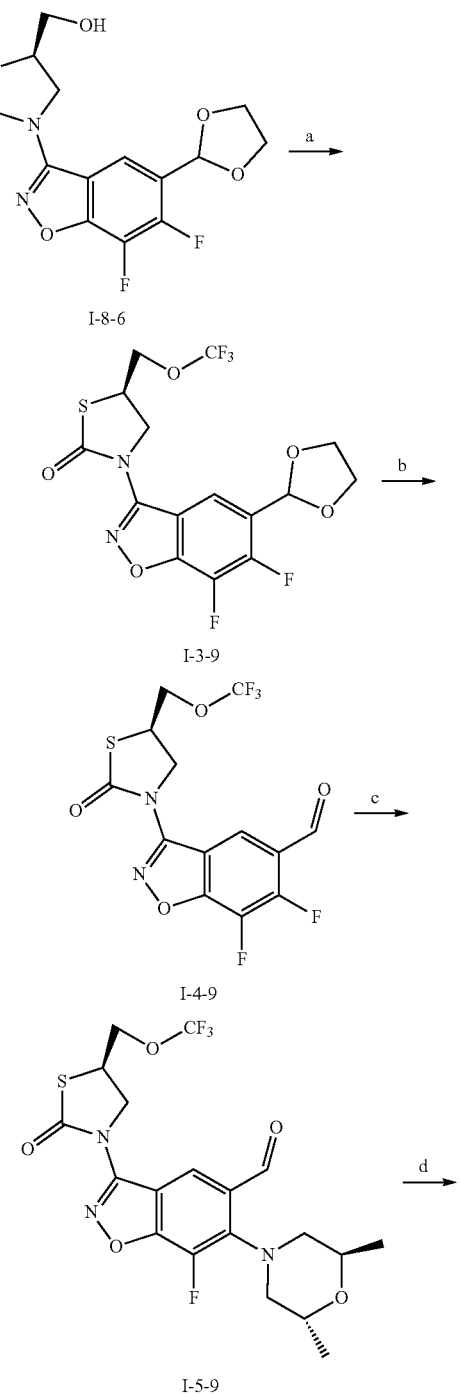

I-4-8. The organic base may be triethylamine or N,N-diisopropylethylamine, and the polar aprotic solvent may be acetonitrile, 1,4-dioxane, tetrahydrofuran, or dimethylformamide. (DMF).

c. The intermediate I-4-8 is reacted with barbituric acid in a mixed solvent of acetic acid and water at 110° C. for 5 hours to form the corresponding compound 8.

Route 5

In a preferred embodiment, compound 9 is prepared according to route 5.

a. An intermediate I-3-7 is reacted with 2,6-di-tert-butylpyridine and trimethyloxonium tetrafluoroborate in a polar aprotic solvent at room temperature for 4 h to form an intermediate I-3-8. The polar aprotic solvent may be dichloromethane, tetrahydrofuran, 1,4-dioxane, or dimethylformamide (DMF).

b. The intermediate I-3-8 is reacted with 2R,6R-dimethylmorpholine in a polar aprotic solvent in the presence of an organic base at 90° C. for 15 hours to form an intermediate

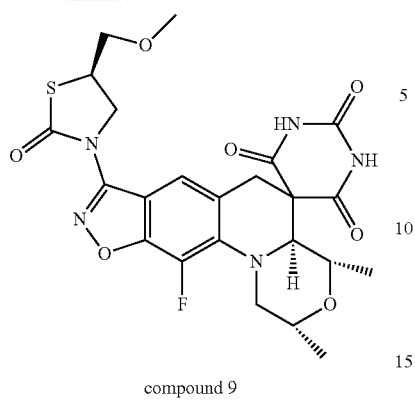

compound 9 a. An intermediate I-8-6 is reacted with silver trifluoromethanesulfonate selective fluorine reagent, potassium fluoride, 2-fluoropyridine, and trifluoromethyltrimethylsilane in ethyl acetate at room temperature for 12 hours to obtain an intermediate I-3-9.

b. The intermediate I-3-9 and hydrochloric acid are reacted in a solvent at room temperature for 2 h to form an intermediate I-4-9. The solvent may be 1,4-dioxane, tetrahydrofuran, or dimethylformamide (DMF).

c. The intermediate I-4-9 is reacted with 2R,6R-dimethylmorpholine in the presence of an organic base in a polar aprotic solvent at 90° C. for 15 h to form an intermediate I-5-9. The organic base may be triethylamine or N,N-diisopropylethylamine, and the polar aprotic solvent may be acetonitrile, 1,4-dioxane, tetrahydrofuran, or dimethylformamide (DMF).

d. The intermediate I-5-9 is reacted with barbituric acid in a mixed solvent of acetic acid and water at 110° C. for 5 hours to form the corresponding compound 9.

Route 6

In a preferred embodiment, compound 10 is prepared according to route 6.

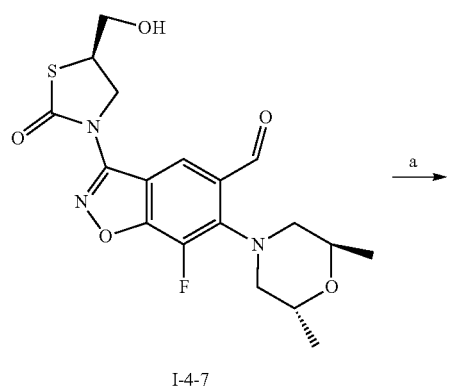

I-4-7

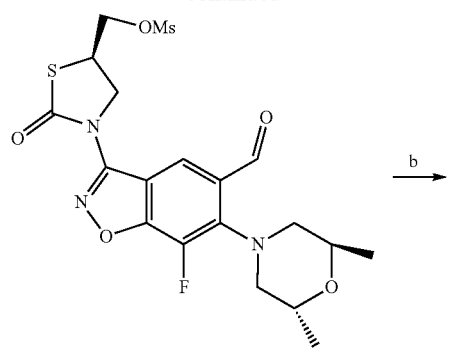

I-3-10

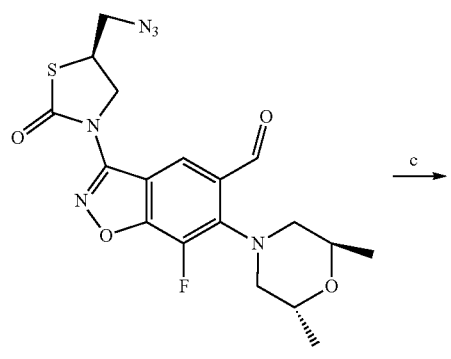

I-4-10

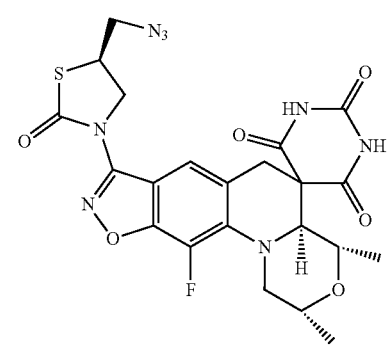

compound 10 a. An intermediate I-4-7 is reacted with methanesulfonyl chloride in the presence of an organic base in a polar aprotic solvent at 0° C. for 15 min to form an intermediate I-3-10. The organic base can be triethylamine or N,N-diisopropylethylamine. The polar aprotic solvent can be dichloromethane, 1,4-dioxane, tetrahydrofuran, or dimethylformamide (DMF).

b. The intermediate I-3-10 is reacted with sodium azide in a polar aprotic solvent at 70° C. for 10 hours to form an intermediate I-4-10. The polar aprotic solvent can be dichloromethane, 1,4-dioxane, tetrahydrofuran, or dimethylformamide (DMF).

c. The intermediate I-4-10 is reacted with barbituric acid in a mixed solvent of acetic acid and water at 110° C. for 5 hours to form the corresponding compound 10.

Route 7

In a preferred embodiment, compound 17 is prepared according to route 7.

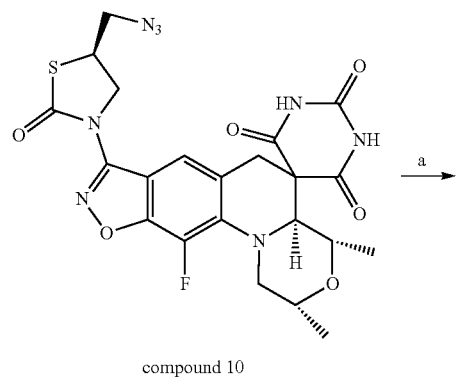

compound 10

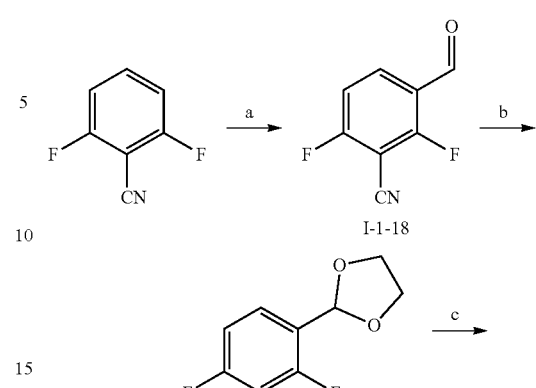

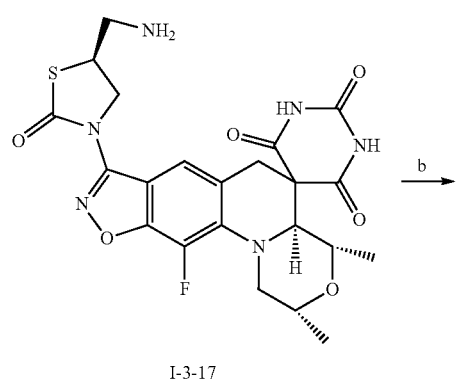

I-3-17

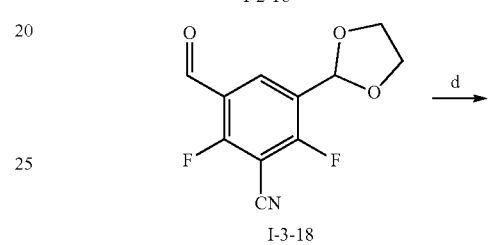

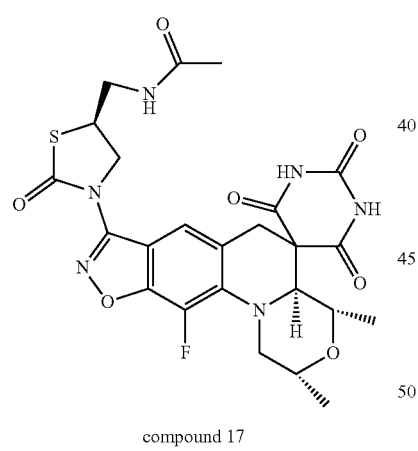

compound 17 a. Compound 10 is reacted with triphenylphosphine in a mixed solvent of tetrahydrofuran and water at room temperature for 12 hours to form an intermediate I-3-17.

d. The intermediate I-3-17 is reacted with acetic anhydride in the presence of an organic base in a polar aprotic solvent at room temperature for 1 h to form compound 17. The organic base may be triethylamine or N N-diisopropylethylamine, and the polar aprotic solvent may be dichloromethane, 1,4-dioxane, tetrahydrofuran, or dimethylformamide (DMF).

Route 8

In a preferred embodiment, compound 18 is prepared according to route 8.

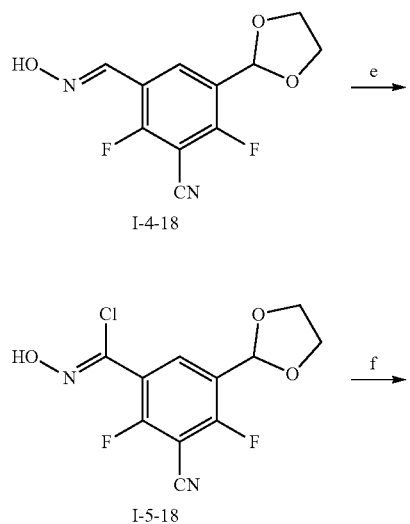

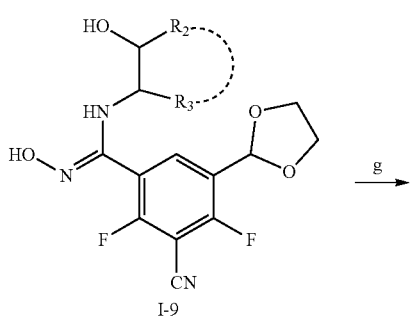

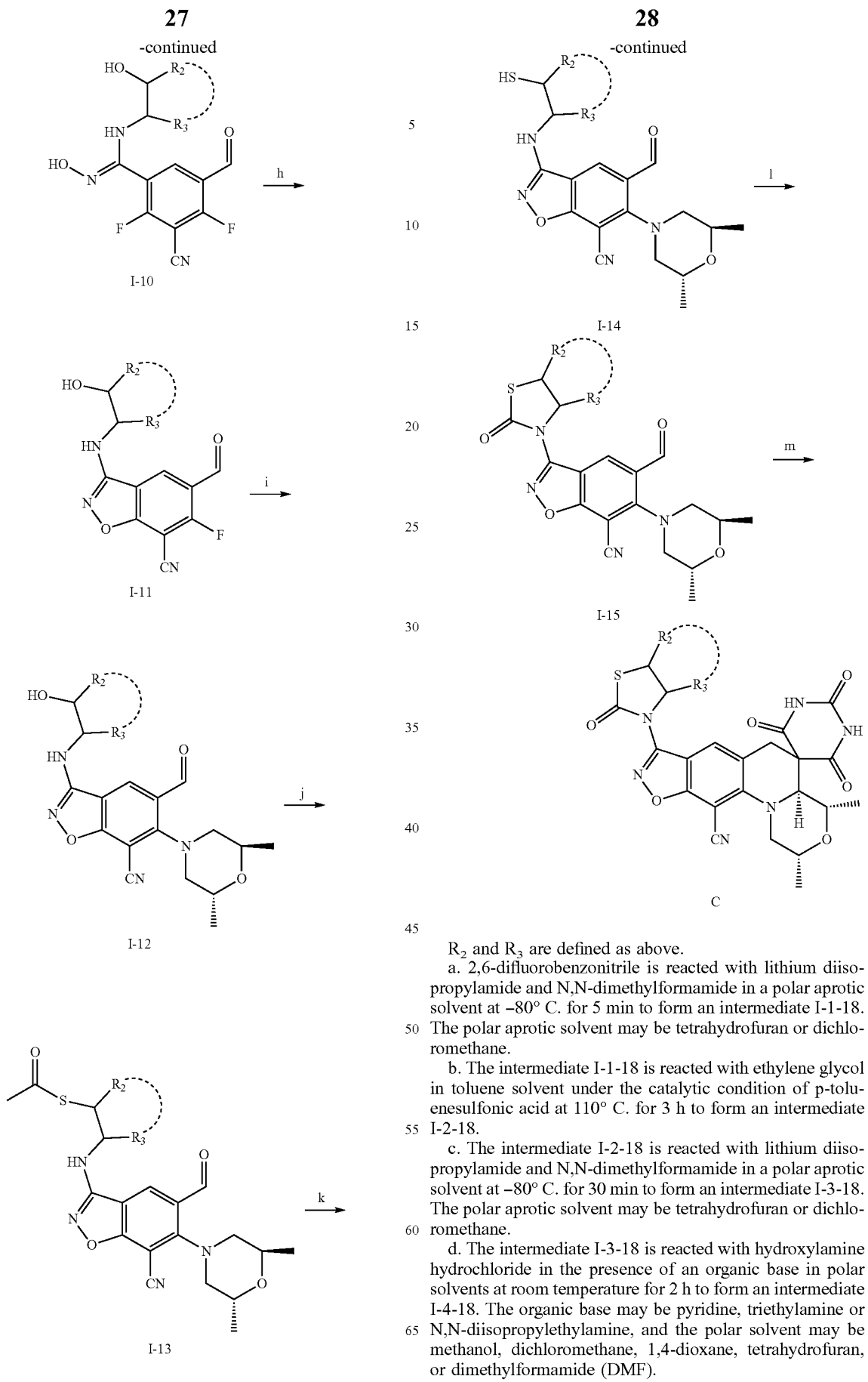

$R_2$ and $R_3$ are defined as above.

a. 2,6-difluorobenzonitrile is reacted with lithium diisopropylamide and N,N-dimethylformamide in a polar aprotic solvent at −80° C. for 5 min to form an intermediate I-1-18. The polar aprotic solvent may be tetrahydrofuran or dichloromethane.

b. The intermediate I-1-18 is reacted with ethylene glycol in toluene solvent under the catalytic condition of p-toluenesulfonic acid at 110° C. for 3 h to form an intermediate I-2-18.

c. The intermediate I-2-18 is reacted with lithium diisopropylamide and N,N-dimethylformamide in a polar aprotic solvent at −80° C. for 30 min to form an intermediate I-3-18. The polar aprotic solvent may be tetrahydrofuran or dichloromethane.

d. The intermediate I-3-18 is reacted with hydroxylamine hydrochloride in the presence of an organic base in polar solvents at room temperature for 2 h to form an intermediate I-4-18. The organic base may be pyridine, triethylamine or N,N-diisopropylethylamine, and the polar solvent may be methanol, dichloromethane, 1,4-dioxane, tetrahydrofuran, or dimethylformamide (DMF).

e. The intermediate I-4-18 is reacted with N-chlorosuccinimide in a polar aprotic solvent at room temperature to 40° C. for 30 minutes to obtain an intermediate I-5-18. The polar aprotic solvent may be 1,4-dioxane, toluene, tetrahydrofuran, or dimethylformamide (DMF).

f. The intermediate I-5-18 is reacted in the presence of various primary amines in a polar aprotic solvent at 0° C. for 30 min to produce an intermediate I-9 via a nucleophilic substitution. The polar aprotic solvent may be 1,4-dioxane, toluene, tetrahydrofuran, or dimethylformamide (DMF).

g. The intermediate I-9 is reacted with hydrochloric acid in a solvent at room temperature for 2 h to form an intermediate I-10. The solvent may be 1,4-dioxane, tetrahydrofuran, or dimethylformamide (DMF).

h. The intermediate I-10 is reacted with an aqueous solution of sodium bicarbonate in a solvent at room temperature for 2 h to form an intermediate I-11. The solvent may be 1,4-dioxane, tetrahydrofuran, or dimethylformamide (DMF).

i. The intermediate I-11 is reacted with 2R,6R-dimethylmorpholine in the presence of an organic base in a polar aprotic solvent at 90° C. for 15 h to form an intermediate I-12. The organic base may be triethylamine or N,N-diisopropylethylamine, and the polar aprotic solvent may be acetonitrile, 1,4-dioxane, tetrahydrofuran, or dimethylformamide (DMF).

j. The intermediate I-12 is reacted with thioacetic acid in the presence of an active intermediate formed by diisopropyl azodicarboxylate and triphenylphosphine in a polar aprotic solvent at room temperature for 2 h to form an intermediate I-13. The polar aprotic solvent may be 1,4-dioxane, toluene, tetrahydrofuran, or dimethylformamide (DMF).

k. The intermediate I-13 is reacted in the presence of sodium hydroxide and dithiothreitol in a solvent at 0° C. for 1 h to form an intermediate I-14. The solvent may be methanol, ethanol, 1,4-dioxane, tetrahydrofuran, or dimethylformamide (DMF).

l. The intermediate I-14 is reacted with N,N'-carbonyldiimidazole under the catalysis of 4-dimethylaminopyridine in a polar aprotic solvent at 80° C. for 4 h to form the corresponding intermediate I-15. The polar aprotic solvent may be 1,4-dioxane, toluene, tetrahydrofuran, or dimethylformamide (DMF).

m. The intermediate I-15 is reacted with barbituric acid in a mixed solvent of acetic acid and water at 110° C. for 5 h to form compound C.

Route 9

In a preferred embodiment, compound 20 is prepared according to route 9.

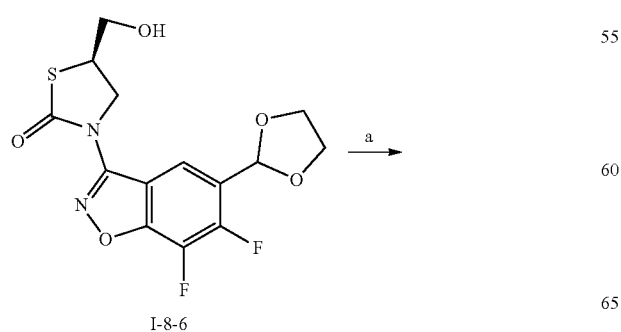

I-8-6

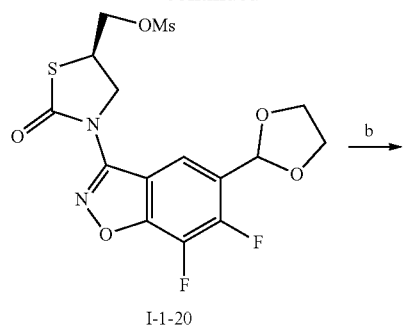

I-1-20

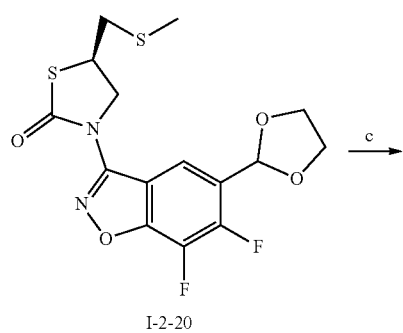

I-2-20

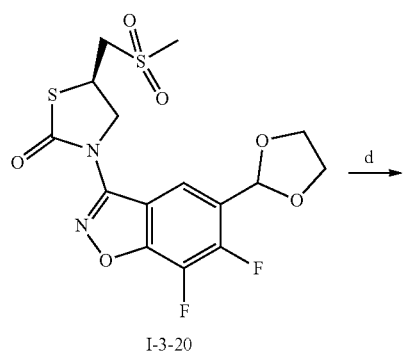

I-3-20

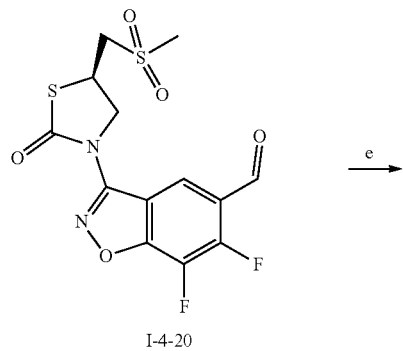

I-4-20

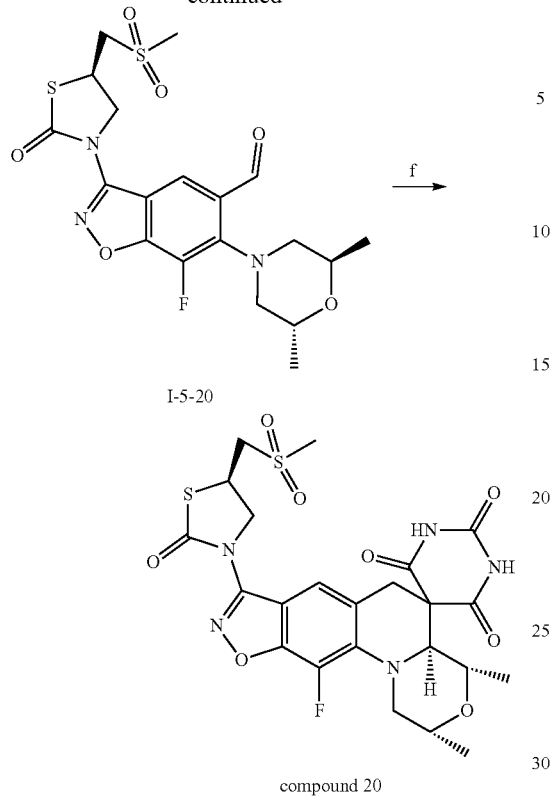

I-5-20

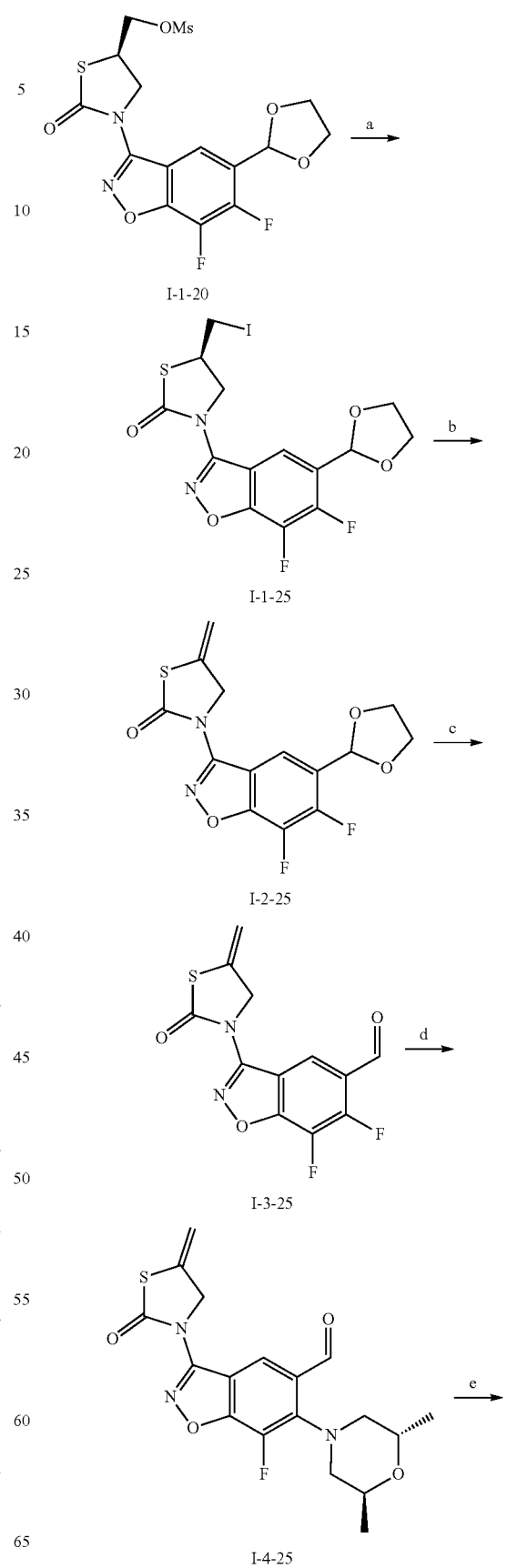

compound 20 a. An intermediate I-8-6 is reacted with methanesulfonyl chloride in the presence of an organic base in a polar aprotic solvent at 0° C. for 30 minutes to produce an intermediate I-1-20. The organic base may be triethylamine or N,N-diisopropylethylamine, and the polar aprotic solvent may be acetonitrile, 1,4-dioxane, tetrahydrofuran, or dimethylformamide (DMF).

b. The intermediate I-1-20 is reacted with sodium methyl mercaptan in a polar aprotic solvent at 0° C. to room temperature for 1 h to form an intermediate I-2-20. The polar aprotic solvent may be acetonitrile, 1,4-dioxane, tetrahydrofuran, or dimethylformamide (DMF).

c. The intermediate I-2-20 is reacted with sodium tungstate and hydrogen peroxide in a polar solvent at 0° C. to room temperature for 30 minutes to form an intermediate I-3-20. The polar solvent may be methanol, acetonitrile, or dimethylformamide (DMF).

d. The intermediate I-3-20 is reacted with hydrochloric acid in a solvent at room temperature for 2 h to form an intermediate I-4-20. The solvent may be 1,4-dioxane, tetrahydrofuran, or dimethylformamide (DMF).

e. The intermediate I-4-20 is reacted with 2R,6R-dimethylmorpholine in the presence of an organic base in a polar aprotic solvent at 90° C. for 15 h to form an intermediate I-5-20. The organic base may be triethylamine or N,N-diisopropylethylamine, and the polar aprotic solvent may be acetonitrile, 1,4-dioxane, tetrahydrofuran, or dimethylformamide. (DMF).

f. The intermediate I-5-20 is reacted with barbituric acid in a mixed solvent of acetic acid and water at 110° C. for 5 hours to form compound 20.

Route 10

In a preferred embodiment, compound 25 is prepared according to route 10.

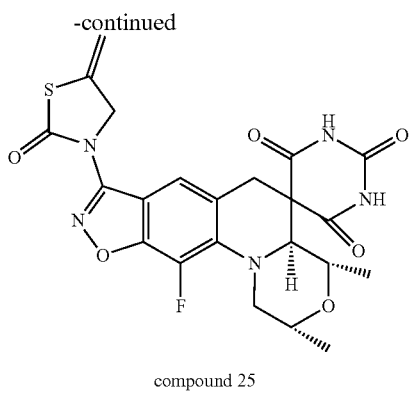

compound 25 a. An intermediate I-1-20 is reacted with sodium iodide in a polar aprotic solvent at 60° C. for 12 hours to form an intermediate I-1-25. The polar aprotic solvent may be acetonitrile, 1,4-dioxane, tetrahydrofuran, or dimethylformamide (DMF).

b. The intermediate I-1-25 is reacted with 1,8-diazabicycloundec-7-ene in a polar aprotic solvent under ultrasonic conditions for 5 minutes to form an intermediate I-2-25. The polar aprotic solvent may be acetonitrile, 1,4-dioxane, tetrahydrofuran, or dimethylformamide (DMF).

c. The intermediate I-2-25 is reacted with hydrochloric acid in a solvent at room temperature for 3 h to form a corresponding intermediate I-3-25. The solvent may be 1,4-dioxane, tetrahydrofuran, or dimethylformamide (DMF).

d. The intermediate I-3-25 is reacted with 2R,6R-dimethylmorpholine in the presence of an organic base in a polar aprotic solvent at 90° C. for 15 hours to form a corresponding intermediate I-4-25. The organic base may be triethylamine or N,N-diisopropylethylamine, and the polar aprotic solvent may be acetonitrile, 1,4-dioxane, tetrahydrofuran, or dimethylformamide (DMF).

e. The intermediate I-4-25 is reacted with barbituric acid in a mixed solvent of acetic acid and water at 110° C. for 5 hours to form compound 25.

Pharmaceutical Composition

The invention also provides a pharmaceutical composition comprising an active ingredient in a safe and effective amount range, and a pharmaceutically acceptable carrier.

The "active ingredient" in the present invention refers to a compound of formula I according to the present invention.

The "active ingredient" and the pharmaceutical composition according to the present invention are used to prepare a medicament for treating infectious diseases. In another preferred embodiment, it is used for preparing a medicament for preventing and/or treating infectious diseases caused by multi-drug resistant bacteria.

By "safe and effective amount", it means that the amount of active ingredient is sufficient to significantly improve the condition without causing serious side effects. Generally, the pharmaceutical composition contains 1-2000 mg of active ingredient/dose, and more preferably 10-200 mg of active ingredient/dose. Preferably, the "one dose" is one tablet.

"Pharmaceutically acceptable carrier" refers to one or more compatible solid or liquid fillers or gel substances that are suitable for human use and must have sufficient purity and low enough toxicity. As used herein, "compatibility" means that each component in the composition can blend with the active ingredient of the present invention each other without significantly reducing the medicinal effect of the active ingredient. Examples of pharmaceutically acceptable carriers are cellulose and its derivatives (such as sodium carboxymethyl cellulose, sodium ethyl cellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerin, mannitol, sorbitol, etc.), emulsifiers (such as Tween*), wetting agents (such as sodium lauryl sulfate), colorants, flavoring agents, stabilizers, antioxidants, preservatives, pyrogen-free water and the like.

The administration method of the active ingredient or the pharmaceutical composition of the present invention is not particularly limited, and representative administration methods include (but are not limited to): oral, intratumoral, rectal, parenteral (intravenous, intramuscular or subcutaneous) administration and the like.

Solid dosage forms for oral administration include capsules, tablets, pills, powders and granules.

Liquid dosage forms for oral administration include pharmaceutically acceptable emulsions, solutions, suspensions, syrups or elixirs.

The compounds of the present invention can be administered alone or in combination with other therapeutic agents, such as antibacterial agents.

When the pharmaceutical composition is used, a safe and effective amount of the compound of the present invention is administered to a mammal (such as a human) in need of treatment, wherein the dose administered is a pharmaceutically effective dose. For a person having 60 kg body weight, the daily dosage is usually 1 to 2000 mg, preferably 20 to 500 mg. Of course, the specific dosage should be determined after considering factors such as the route of administration, the patient's health, and other factors, which are within the skill of a skilled physician.

The present invention will be further described below with reference to specific embodiments. It should be understood that these examples are only used to illustrate the present invention and not to limit the scope of the present invention. The experimental methods without specific conditions in the following examples are generally performed according to conventional conditions (such as the conditions described in Sambrook et al., Molecular Cloning: Laboratory Manual (New York: Cold Spring Harbor Laboratory Press, 1989)) or according to manufacturing conditions recommended by the manufacturer. Unless stated otherwise, percentages are percentages by weight and parts are parts by weight.

Unless otherwise defined, all professional and scientific terms used herein have the same meaning as those familiar to those skilled in the art. In addition, any methods and materials similar or equal to those described can be used in the method of the present invention. The preferred implementation methods and materials described herein are for demonstration purposes only.

In all the examples below, $^1$H-NMR was recorded with a Varian Mercury 400 nuclear magnetic resonance instrument, and $^{13}$C-NMR was recorded with a BRUKER 500 MHz nuclear magnetic resonance instrument (low temperature), and the chemical shift was expressed in δ (ppm); silica gel used for separation were 200-300 mesh unless otherwise stated. The proportion of eluent is volume ratio.

Example 1: (2R,4S,4aS)-11-fluoro-2,4-dimethyl-8-(2-oxothiazolin-3-yl)-1,2,4,4a-tetrahydro-2'H,6H-spiro[isoxazole[4,5-g][1,4]oxazine[4,3-a]quinoline-5,5'-pyrimidine]-2',4',6'(1'H,3'H)-trione (Compound 1)

(a) 2-((5-(1,3-dioxolan-2-yl)-6,7-difluorobenzo[d]isoxazol-3-yl)amino)ethanol (I-3-1)

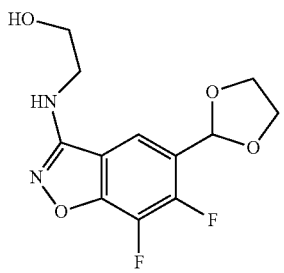 [SMILES: OCCNc1noc2c(F)c(F)c(C3OCCO3)cc12]

An intermediate A (500 mg, 2.024 mmol) and N-chlorosuccinimide (324 mg, 2.429 mmol) were added to 15 ml of N,N-dimethylformamide at room temperature and stirred until the mixture was dissolved. The mixture was warmed to 40° C. for 15 min. The reaction was monitored by TLC. After the reaction completion, the temperature was reduced to 0° C. Ethanolamine (0.300 ml, 5.060 mmol) was slowly added dropwise. After 5 min, TLC detection showed the reaction was completed. Cesium carbonate (3.297 g, 10.120 mmol) was added and the reaction mixture was raised to 60° C. and reacted for 3 h. The reaction was monitored by TLC. After the reaction completion, the temperature was lowered to room temperature. Water was added and the mixture was extracted with ethyl acetate. The combined organic layers was concentrated to remain a small amount of solvent, crystallized, filtered, and dried to obtain 322 mg of white solid in a yield of 55%. $^1$H NMR (400 MHz, DMSO) δ 7.99 (dd, J=5.8, 1.4 Hz, 1H), 7.38 (t, J=5.5 Hz, 1H), 6.09 (s, 11H), 4.81 (t, J=5.5 Hz, 1H), 4.10-4.01 (m, 4H), 3.62 (q, J=5.8 Hz, 2H), 3.29 (q, J=5.8 Hz, 2H).

(b) S-(2-((5-(1,3-dioxolan-2-yl)-6,7-difluorobenzo[d]isoxazol-3-yl)amino)ethyl) acetylthio (I-4-1)

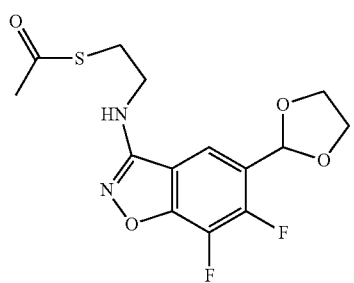 [SMILES: CC(=O)SCCNc1noc2c(F)c(F)c(C3OCCO3)cc12]

Triphenylphosphine (360 mg, 1.384 mmol) was dissolved in 20 ml dry tetrahydrofuran, and diisopropyl azodicarboxylate (0.28 ml, 1.384) was slowly added dropwise under argon protection in an ice bath and stirred for 30 min. I-3-1 (200 mg, 0.692 mmol) and thioacetic acid (0.08 ml, 1.038 mmol) were dissolved in 2 ml dry tetrahydrofuran, and then slowly added dropwise to the reaction solution, stirred for 30 min under ice bath. TLC was used to monitor the reaction completion. The reaction was quenched with water, and the mixture was extracted with ethyl acetate. The organic layers were combined, washed with water and saturated brine, dried over anhydrous sodium sulfate, concentrated under reduced pressure and purified by column chromatography [petroleum ether:ethyl acetate=2:1] to give 214 mg of pale yellow solid in a yield of 90%. $^1$H NMR (400 MHz, CDCl$_3$) δ 7.43 (dd, J=5.4, 1.5 Hz, 1H), 6.09 (s, 1H), 4.78 (t, J=5.6 Hz, 1H), 4.20-4.07 (m, 4H), 3.63 (dd, J=12.2, 6.0 Hz, 2H), 3.23 (t, J=6.3 Hz, 2H), 2.38 (s, 3H).

(c) 3-(5-(1,3-dioxolan-2-yl)-6,7-difluorobenzo[d]isoxazol-3-yl)tetrahydrothiazol-2-one (I-6-1)

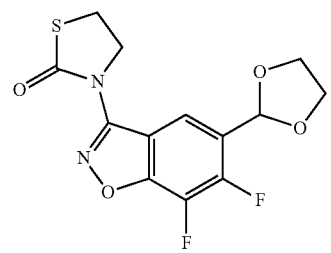 [SMILES: O=C1SCCN1c1noc2c(F)c(F)c(C3OCCO3)cc12]

I-4-1 (264 mg, 0.767 mmol) was added into a mixed solvent of 15 ml ethanol and 5 ml tetrahydrofuran and stirred to dissolve. Dithiothreitol (118 mg, 0.767 mmol) was added, and the reaction solution was lowered to 0° C. 0.8 ml of 1M aqueous sodium hydroxide solution was slowly added and stirred for 30 min. The reaction completion was monitored by TLC. Water was added and the mixture was extracted with ethyl acetate. The organic layers were combined, washed with water and saturated brine, dried over anhydrous sodium sulfate, concentrated under reduced pressure to obtain white solid. 15 ml of N,N-dimethylformamide was added and stirred to dissolve. Carbonyldiimidazole (370 mg, 2.284 mmol) was added and then 4-dimethylaminopyridine (47 mg, 0.381 mmol) was added, and heated to 90° C. for 4 h. The reaction was monitored by TLC. After the reaction was completed, the mixture was cooled to room temperature, and extracted with water and ethyl acetate. The organic layers were combined, washed with water and saturated brine, dried over anhydrous sodium sulfate, concentrated under reduced pressure and purified by column chromatography [petroleum ether:ethyl acetate=5:1] to obtain 167 mg of white solid in a yield of 67% in two steps. $^1$H NMR (400 MHz, CDCl$_3$) δ 8.18 (dd, J=5.9, 1.7 Hz, 1H), 6.15 (s, 1H), 4.36 (t, J=7.2 Hz, 2H), 4.22-4.07 (m, 4H), 3.59 (t, J=7.2 Hz, 2H).

(d) 6,7-difluoro-3-(2-oxothiazolin-3-yl)benzo[d]isoxazole-5-carbaldehyde (I-7-1)

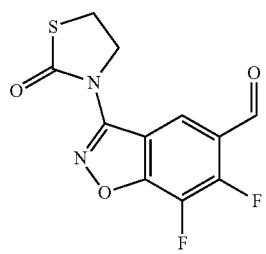 [SMILES: O=Cc1cc2c(N3CCSC3=O)noc2c(F)c1F]

I-6-1 (160 mg, 0.488 mmol) was added into 15 ml of 1,4-dioxane and stirred to dissolve. 4 ml of 6 M aqueous hydrochloric acid solution was slowly added and reacted at room temperature for 2 h. The reaction was monitored by TLC. After the reaction was completed, water was added and the mixture was extracted with ethyl acetate. The combined organic layers was washed with water, washed with saturated brine, dried over anhydrous sodium sulfate, concentrated under reduced pressure and purified by column chromatography [petroleum ether:ethyl acetate=5:1] to obtain 140 mg of white solid with a yield of 100%. $^1$H NMR (400 MHz, CDCl$_3$) δ 10.30 (s, 1H), 8.62 (dd, J=5.8, 1.8 Hz, 1H), 4.37 (t, J=7.2 Hz, 2H), 3.62 (t, J=7.2 Hz, 2H).

(e) 6-((2R,6R)-2,6-dimethylmorpholine)-7-fluoro-3-(2-oxothiazolin-3-yl)benzo[d]isoxazole-5-carbaldehyde (I-8-1)

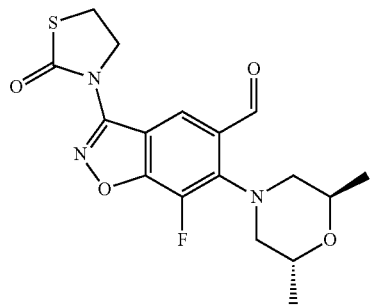 [SMILES: C[C@@H]1CN(c2c(C=O)cc3c(N4CCSC4=O)noc3c2F)C[C@@H](C)O1]

I-7-1 (140 mg, 0.493 mmol) was added into 20 ml of acetonitrile, stirred to dissolve, and 2R,6R-dimethylmorpholine (114 mg, 0.986 mmol) and N,N-diisopropylethylamine (0.16 ml, 0.986 mmol) were added successively. The mixture was raised to 85° C. and reacted for 8 h. The reaction was monitored by TLC. After the reaction was completed, the mixture was cooled to room temperature. Water was added and the mixture was extracted with ethyl acetate. The combined organic layers were washed with water and saturated brine, dried over anhydrous sodium sulfate, concentrated under reduced pressure and purified by column chromatography [petroleum ether:dichloromethane:ethyl acetate=5:5:1] to obtain 78 mg of white solid in a yield of 42%. $^1$H NMR (400 MHz, CDCl$_3$) δ 10.40 (d, J=3.2 Hz, 1H), 8.48 (d, J=3.8 Hz, 1H), 4.35 (t, J=7.2 Hz, 2H), 4.30-4.21 (m, 2H), 3.60 (t, J=7.1 Hz, 2H), 3.44 (d, J=11.8 Hz, 2H), 3.05 (dd, J=12.0, 5.5 Hz, 2H), 1.34 (d, J=6.4 Hz, 6H).

(f) (2R,4S,4aS)-11-fluoro-2,4-dimethyl-8-(2-oxothiazolin-3-yl)-1,2,4,4a-tetrahydro-2'H,6 H-spiro[isoxazole[4,5-g][1,4]oxazine[4,3-a]quinoline-5,5'-pyrimidine]-2',4',6'(1'H,3'H)-trione (Compound 1)

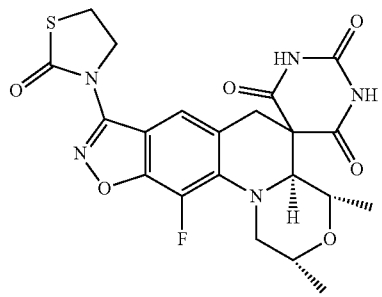

I-8-1 (78 mg, 0.206 mmol) was added into a mixed solvent of 4 ml acetic acid and 1 ml water and stirred to dissolve. Barbituric acid (35 mg, 0.267 mmol) was added and the mixture was warmed to 110° C. and reacted for 3 h. The reaction was monitored by TLC. After the reaction was completed, the mixture was cooled to room temperature. Water was added and the mixture was extracted with ethyl acetate. The combined organic layers were washed with water and saturated brine, dried over anhydrous sodium sulfate, concentrated under reduced pressure and prepared by reversed-phase column [methanol:water=30:70] to obtain 85 mg of white solid in a yield of 84%. m.p. 225-226° C.; $^1$H NMR (400 MHz, DMSO) δ 11.85 (s, 1H), 11.48 (s, 1H), 7.42 (s, 1H), 4.23 (t, J=6.6 Hz, 2H), 4.10 (d, J=13.7 Hz, 1H), 3.94 (d, J=8.9 Hz, 1H), 3.82-3.74 (m, 1H), 3.71-3.56 (m, 4H), 3.16-3.06 (m, 1H), 2.91 (d, J=13.6 Hz, 1H), 1.14 (d, J=5.8 Hz, 3H), 0.89 (d, J=6.1 Hz, 3H); $^{13}$C NMR (126 MHz, DMSO) δ 172.04, 171.38, 168.12, 154.04, 153.98, 149.96, 135.24, 133.78 (d, J=239.0 Hz), 122.84, 118.67, 107.34, 72.56, 72.14, 64.82, 56.73 (d, J=9.0 Hz), 53.39, 49.95, 38.98, 27.22, 18.64, 18.61; MS(ESI) m/z: [(M−1)$^-$, 488.1].

Example 2: (2R,4S,4aS)-11-fluoro-2,4-dimethyl-8-((S)-5-methyl-2-oxothiazolin-3-yl)-1,2, 4,4a-tetrahydro-2'H,6H-spiro[isoxazole[4,5-g][1,4]oxazine[4,3-a]quinoline-5,5'-pyrimidine]-2',4',6'(1'H,3'H)-trione (Compound 2)

(a) R-1-((5-(1,3-dioxolan-2-yl)-6,7-difluorobenzo[d]isoxazol-3-yl)amino)isopropanol (I-3-2)

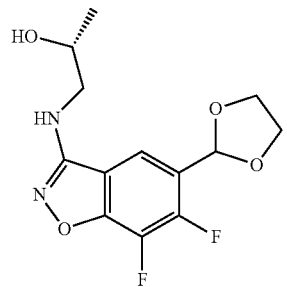 [SMILES: C[C@@H](O)CNc1noc2c(F)c(F)c(C3OCCO3)cc12]

According to the synthesis method of intermediate I-3-1, an intermediate A (700 mg, 2.833 mmol), N-chlorosuccinimide (454 mg, 3.400 mmol), (R)-1-amino-2-propanol (0.800 ml, 8.499 mmol) and cesium carbonate (3.692 g, 11.332 mmol) were used as raw materials and 644 mg of white solid was prepared in a yield of 76%. ¹H NMR (400 MHz, DMSO) δ 8.03 (d, J=4.7 Hz, 1H), 7.34 (t, J=5.8 Hz, 1H), 6.08 (s, 11H), 4.81 (d, J=4.8 Hz, 1H), 4.11-4.00 (m, 4H), 3.91 (dt, J=11.7, 5.9 Hz, 1H), 3.15 (t, J=5.8 Hz, 2H), 1.12 (d, J=6.2 Hz, 3H).

(b) (S)—S-(1-((5-(1,3-dioxolan-2-yl)-6,7-difluorobenzo[d]isoxazol-3-yl)amino)isopropanol) acetylthio (I-4-2)

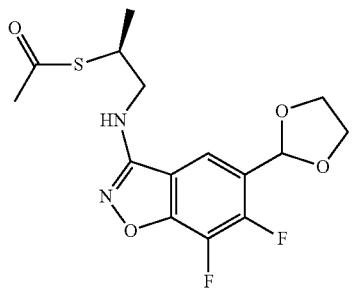 [SMILES: CC(=O)S[C@@H](C)CNc1noc2c(F)c(F)c(C3OCCO3)cc12]

According to the synthesis method of S-(2-((5-(1,3-dioxolan-2-yl)-6,7-difluorobenzo[d]isoxazol-3-yl)amino) ethyl)acetylthio (I-4-1), an intermediate I-3-2 (644 mg, 2.146 mmol), triphenylphosphine (1.69 g, 6.438 mmol), diisopropyl azodicarboxylate (1.27 ml, 6.438 mmol) and thioacetic acid (0.46 ml, 6.438 mmol) were used as raw materials and 700 mg of light yellow solid was prepared in a yield of 91%. ¹H NMR (400 MHz, CDCl₃) δ 7.44 (dd, J=5.3, 1.4 Hz, 1H), 6.11 (s, 1H), 4.84 (t, J=5.5 Hz, 1H), 4.23-4.10 (m, 4H), 3.94-3.87 (m, 1H), 3.68 (dt, J=13.4, 5.0 Hz, 1H), 3.57-3.49 (m, 1H), 2.38 (s, 3H), 1.44 (d, J=7.2 Hz, 3H).

(c) (S)-3-(5-(1,3-dioxolan-2-yl)-6,7-difluorobenzo[d]isoxazol-3-yl)-5-methylthiazol-2-one (I-6-2)

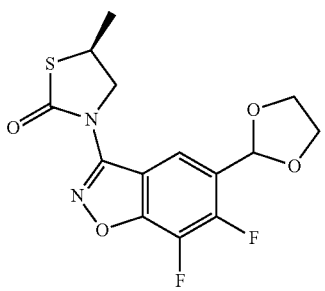 [SMILES: C[C@H]1CN(c2noc3c(F)c(F)c(C4OCCO4)cc23)C(=O)S1]

According to the synthesis method of 3-(5-(1,3-dioxolan-2-yl)-6,7-difluorobenzo[d]isoxazol-3-yl)tetrahydrothiazol-2-one (I-6-1), an intermediate I-4-2 (700 mg, 1.955 mmol), sodium hydroxide (86 mg, 2.151 mmol), dithiothreitol (301 mg, 1.955 mmol), N,N-carbonyldiimidazole (633 mg, 3.910 mmol), and 4-dimethylaminopyridine (238 mg, 1.955 mmol) were used as raw materials, and 600 mg of white solid was prepared in a yield of 90%. ¹H NMR (400 MHz, CDCl₃) δ 8.19 (dd, J=5.9, 1.8 Hz, 1H), 6.15 (s, 1H), 4.41 (dd, J=10.8, 6.8 Hz, 1H), 4.24-4.08 (m, 5H), 3.98 (dd, J=10.8, 6.8 Hz, 1H), 1.64 (d, J=6.7 Hz, 3H).

(d) (S)-6,7-difluoro-3-(5-methyl-2-oxothiazolin-3-yl)benzo[d]isoxazole-5-carbaldehyde (I-7-2)

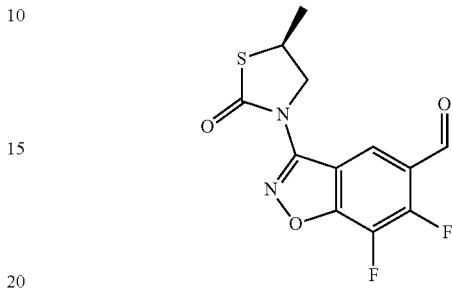

According to the synthesis method of 6,7-difluoro-3-(2-oxothiazolin-3-yl)benzo[d]isoxazole-5-carbaldehyde (I-7-1), an intermediate I-6-2 (600 mg, 1.754 mmol) and 6 M hydrochloric acid (10 ml) were used as raw materials, and 500 mg of white solid was prepared in a yield of 95%. ¹H NMR (400 MHz, CDCl₃) δ 10.30 (s, 1H), 8.63 (dd, J=5.8, 1.8 Hz, 1H), 4.42 (dd, J=10.8, 6.8 Hz, 1H), 4.17-4.08 (m, 1H), 3.98 (dd, J=10.8, 6.8 Hz, 1H), 1.65 (d, J=6.7 Hz, 3H).

(e) 6-((2R,6R)-2,6-dimethylmorpholine)-7-fluoro-3-((S)-5-methyl-2-oxothiazolin-3-yl)benzo[d]isoxazole-5-carbaldehyde (I-8-2)

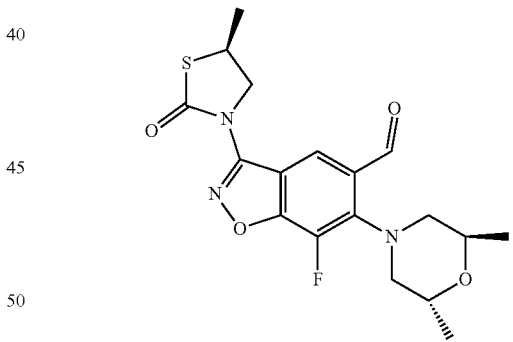

According to the synthesis method of 6-((2R,6R)-2,6-dimethylmorpholine)-7-fluoro-3-(2-oxothiazolin-3-yl) benzo[d]isoxazole-5-carbaldehyde (I-8-1), an intermediate I-7-2 (350 mg, 1.174 mmol), 2R,6R-dimethylmorpholine (0.362 ml, 2.936 mmol), and N,N-diisopropyl ethylamine (0.582 ml, 3.523 mmol) were used as raw materials and 180 mg of light yellow solid was prepared in a yield of 39%. ¹H NMR (400 MHz, CDCl₃) δ 10.40 (s, 1H), 8.50 (s, 1H), 4.41 (dd, J=10.6, 7.0 Hz, 1H), 4.30-4.21 (m, 2H), 4.16-4.06 (m, 1H), 3.96 (dd, J=10.7, 6.7 Hz, 1H), 3.44 (d, J=11.6 Hz, 2H), 3.05 (dd, J=11.9, 5.7 Hz, 2H), 1.64 (d, J=6.7 Hz, 3H), 1.34 (d, J=6.4 Hz, 6H).

(f) (2R,4S,4aS)-11-fluoro-2,4-dimethyl-8-((S)-5-methyl-2-oxothiazolin-3-yl)-1,2,4,4a-tetrahydro-2'H,6H-spiro[isoxazole[4,5-g][1,4]oxazine[4,3-a]quinoline-5,5'-pyrimidine]-2',4',6'(1'H,3'H)-trione (Compound 2)

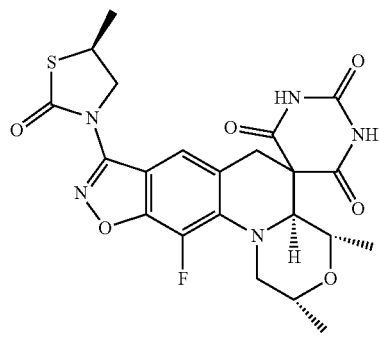

According to the synthesis method of compound 1, an intermediate I-8-2 (175 mg, 0.445 mmol) and barbituric acid (60.2 mg, 0.470 mmol) were used as raw materials to prepare 200 mg of white solid in a yield of 91%. $^1$H NMR (400 MHz, DMSO) δ 11.83 (s, 1H), 11.47 (s, 1H), 7.42 (s, 1H), 4.35 (dd, J=10.6, 6.9 Hz, 1H), 4.25-4.15 (m, 1H), 4.10 (d, J=12.9 Hz, 1H), 3.97-3.86 (m, 2H), 3.83-3.74 (m, 1H), 3.71-3.60 (m, 2H), 3.16-3.06 (m, 11H), 2.91 (d, J=14.3 Hz, 11H), 1.50 (d, J=6.6 Hz, 3H), 1.15 (d, J=6.3 Hz, 3H), 0.89 (d, J=6.3 Hz, 3H); $^{13}$C NMR (126 MHz, DMSO) δ 171.50, 171.39, 168.13, 154.02 (d, J=6.7 Hz), 153.94, 149.96, 135.28, 133.79 (d, J=238.9 Hz), 122.87, 118.65, 107.36, 72.57, 72.14, 64.84, 56.74 (d, J=9.5 Hz), 56.64, 53.39, 38.98, 38.92, 20.58, 18.64, 18.61; MS (EI) m/z: [M$^+$, 503].

Example 3: (2R,4S,4aS)-11-fluoro-2,4-dimethyl-8-((R)-5-methyl-2-oxothiazolin-3-yl)-1, 2,4,4a-tetrahydro-2'H,6H-spiro[isoxazole[4,5-g][1,4]oxazine[4,3-a]quinoline-5,5'-pyrimidine]-2',4',6'(1'H,3'H)-trione (Compound 3)

(a) S-1-((5-(1,3-dioxolan-2-yl)-6,7-difluorobenzo[d]isoxazol-3-yl)amino)isopropanol (I-3-3)

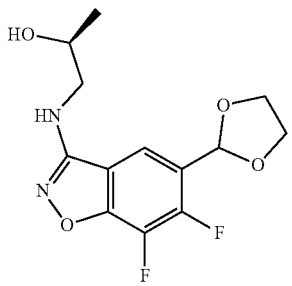 [SMILES: C[C@H](O)CNc1noc2c(F)c(F)c(C3OCCO3)cc12]

According to the synthesis method of intermediate I-3-1, an intermediate A (700 mg, 2.833 mmol), N-chlorosuccinimide (454 mg, 3.400 mmol), (S)-1-amino-2-propanol (0.800 ml, 8.499 mmol) and cesium carbonate (3.692 g, 11.332 mmol) were used as raw materials and 688 mg of white solid was prepared in a yield of 81%. $^1$H NMR (400 MHz, DMSO) δ 8.03 (d, J=4.7 Hz, 1H), 7.34 (t, J=5.8 Hz, 11H), 6.08 (s, 11H), 4.81 (d, J=4.8 Hz, 1H), 4.11-4.00 (m, 4H), 3.91 (dt, J=11.7, 5.9 Hz, 11H), 3.15 (t, J=5.8 Hz, 2H), 1.12 (d, J=6.2 Hz, 31H).

(b) (R)—S-(1-((5-(1,3-dioxolan-2-yl)-6,7-difluorobenzo[d]isoxazol-3-yl)amino)isopropanol) acetylthio (I-4-3)

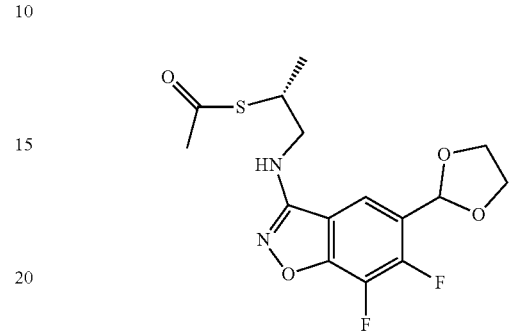

According to the synthesis method of S-(2-((5-(1,3-dioxolan-2-yl)-6,7-difluorobenzo[d]isoxazol-3-yl)amino)ethyl)acetylthio (I-4-1), an intermediate I-3-3 (820 mg, 2.733 mmol), triphenylphosphine (2.15 g, 8.198 mmol), diisopropyl azodicarboxylate (1.60 ml, 8.198 mmol) and thioacetic acid (0.39 ml, 5.466 mmol) were used as raw materials and 800 mg of light yellow solid was prepared in a yield of 82%. $^1$H NMR (400 MHz, CDCl$_3$) δ 7.44 (dd, J=5.3, 1.4 Hz, 1H), 6.11 (s, 11H), 4.84 (t, J=5.5 Hz, 11H), 4.23-4.10 (m, 4H), 3.94-3.87 (m, 11H), 3.68 (dt, J=13.4, 5.0 Hz, 1H), 3.57-3.49 (m, 1H), 2.38 (s, 3H), 1.44 (d, J=7.2 Hz, 3H).

(c) (R)-3-(5-(1,3-dioxolan-2-yl)-6,7-difluorobenzo[d]isoxazol-3-yl)-5-methylthiazol-2-one (I-6-3)

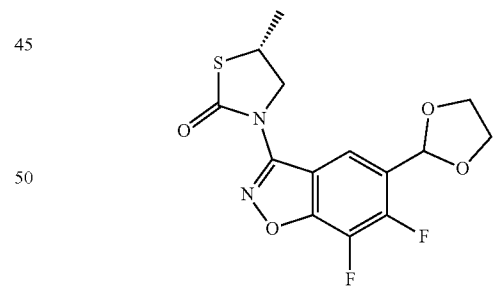

According to the synthesis method of 3-(5-(1,3-dioxolan-2-yl)-6,7-difluorobenzo[d]isoxazol-3-yl) tetrahydrothiazol-2-one (I-6-1), an intermediate I-4-3 (847 mg, 2.366 mmol), sodium hydroxide (142 mg, 3.549 mmol), dithiothreitol (365 mg, 2.366 mmol), N,N-carbonyl diimidazole (766 mg, 4.732 mmol), and 4-dimethylaminopyridine (289 mg, 2.366 mmol) were used as raw materials and 735 mg of white solid was prepared in a yield of 91%. $^1$H NMR (400 MHz, CDCl$_3$) δ 8.19 (dd, J=5.9, 1.8 Hz, 11H), 6.15 (s, 1H), 4.41 (dd, J=10.8, 6.8 Hz, 11H), 4.24-4.08 (m, 51H), 3.98 (dd, J=10.8, 6.8 Hz, 1H), 1.64 (d, J=6.7 Hz, 3H).

(d) (R)-6,7-difluoro-3-(5-methyl-2-oxothiazolin-3-yl)benzo[d]isoxazole-5-carbaldehyde (I-7-3)

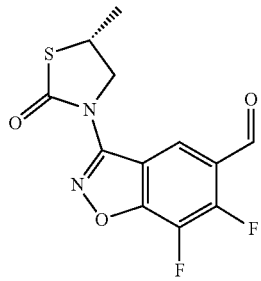 [SMILES: C[C@@H]1CN(c2noc3c(F)c(F)c(C=O)cc23)C(=O)S1]

According to the synthesis method of 6,7-difluoro-3-(2-oxothiazolin-3-yl)benzo[d]isoxazole-5-carbaldehyde (I-7-1), an intermediate I-6-3 (700 mg, 2.046 mmol) and 6M hydrochloric acid (15 ml) were used as raw materials to prepare 600 mg of white solid in a yield of 98%. $^1$H NMR (400 MHz, CDCl$_3$) δ 10.30 (s, 1H), 8.63 (dd, J=5.8, 1.8 Hz, 1H), 4.42 (dd, J=10.8, 6.8 Hz, 1H), 4.17-4.08 (m, 1H), 3.98 (dd, J=10.8, 6.8 Hz, 1H), 1.65 (d, J=6.7 Hz, 3H).

(e) 6-((2R,6R)-2,6-dimethylmorpholine)-7-fluoro-3-((R)-5-methyl-2-oxothiazolin-3-yl)benzo[d]isoxazole-5-carbaldehyde (I-8-3)

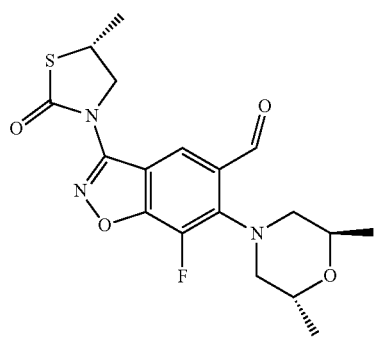 [SMILES: C[C@@H]1CN(c2c(C=O)cc3c(N4C[C@@H](C)SC4=O)noc3c2F)C[C@@H](C)O1]

According to the synthesis method of 6-((2R,6R)-2,6-dimethylmorpholine)-7-fluoro-3-(2-oxothiazolin-3-yl)benzo[d]isoxazole-5-carbaldehyde (I-8-1), an intermediate I-7-3 (100 mg, 0.336 mmol), 2R,6R-dimethylmorpholine (0.104 ml, 0.839 mmol), and N,N-diisopropyl ethylamine (0.179 ml, 1.007 mmol) were used as raw materials and 72 mg of light yellow solid was prepared in a yield of 55%. $^1$H NMR (400 MHz, CDCl$_3$) δ 10.40 (s, 1H), 8.49 (s, 1H), 4.41 (dd, J=10.8, 6.9 Hz, 1H), 4.30-4.21 (m, 2H), 4.16-4.06 (m, 1H), 3.96 (dd, J=10.9, 6.7 Hz, 1H), 3.44 (d, J=11.9 Hz, 2H), 3.05 (dd, J=12.0, 5.5 Hz, 2H), 1.64 (d, J=6.7 Hz, 3H), 1.34 (d, J=6.4 Hz, 6H).

(f) (2R,4S,4aS)-11-fluoro-2,4-dimethyl-8-((R)-5-methyl-2-oxothiazolin-3-yl)-1,2,4,4a-tetrahydro-2'H,6H-spiro[isoxazole[4,5-g][1,4]oxazine[4,3-a]quinoline-5,5'-pyrimidine]-2',4',6'(1'H,3'H)-trione (Compound 3)

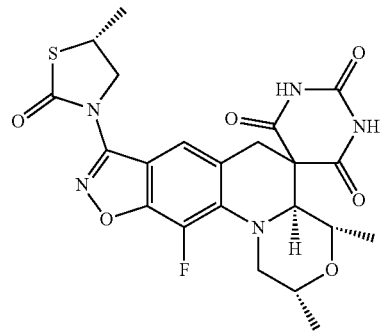

According to the synthesis method of compound 1, an intermediate I-8-3 (63 mg, 0.160 mmol) and barbituric acid (23 mg, 0.176 mmol) were used as raw materials to prepare 67 mg of white solid in a yield of 83%. $^1$H NMR (400 MHz, DMSO) δ 11.83 (s, 1H), 11.48 (s, 1H), 7.43 (s, 1H), 4.36 (dd, J=10.6, 7.0 Hz, 1H), 4.20-4.06 (m, 2H), 3.97-3.86 (m, 2H), 3.84-3.74 (m, 1H), 3.72-3.61 (m, 2H), 3.16-3.06 (m, 1H), 2.91 (d, J=14.2 Hz, 1H), 1.50 (d, J=6.6 Hz, 3H), 1.14 (d, J=6.3 Hz, 3H), 0.89 (d, J=6.3 Hz, 3H); $^{13}$C NMR (126 MHz, DMSO) δ 171.48, 171.39, 168.15, 154.04, 153.94, 149.95, 135.26, 133.75 (d, J=238.9 Hz), 122.83, 118.62, 107.33, 72.59, 72.14, 64.81, 56.75 (d, J=8.9 Hz), 56.52, 53.30, 38.96, 38.67, 21.42, 18.65, 18.61; MS (EI) m/z: [M$^+$, 503].

Example 4: (2R,4S,4aS)-11-fluoro-2,4-dimethyl-8-((R)-4-methyl-2-oxothiazolin-3-yl)-1, 2,4,4a-tetrahydro-2'H,6H-spiro[isoxazole[4,5-g][1,4]oxazine[4,3-a]quinoline-5,5'-pyrimidine]-2',4',6'(1'H,3'H)-trione (Compound 4)

(a) (R)-2-((5-(1,3-dioxolan-2-yl)-6,7-difluorobenzo[d]isoxazol-3-yl)amino)propanol (I-3-4)

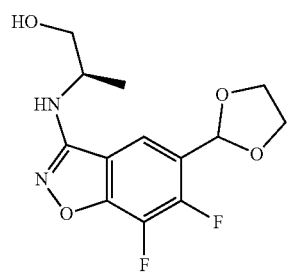 [SMILES: C[C@H](CO)Nc1noc2c(F)c(F)c(C3OCCO3)cc12]

According to the synthesis method of intermediate I-3-1, an intermediate A (700 mg, 2.833 mmol), N-chlorosuccinimide (454 mg, 3.400 mmol), (R)-2-amino-1-propanol (0.800 ml, 8.499 mmol) and cesium carbonate (3.692 g, 11.332 mmol) were used as raw materials to prepare 578 mg of white solid in a yield of 68%. $^1$H NMR (400 MHz, DMSO) δ 8.01 (d, J=4.8 Hz, 1H), 7.13 (d, J=7.3 Hz, 1H), 6.09 (s, 1H), 4.81 (t, J=5.6 Hz, 1H), 4.11-4.01 (m, 4H), 3.62

(dt, J=12.5, 6.4 Hz, 1H), 3.54 (dt, J=10.6, 5.2 Hz, 1H), 3.47-3.39 (m, 1H), 1.21 (d, J=6.5 Hz, 3H).

(b) (R)—S-(2-((5-(1,3-dioxolan-2-yl)-6,7-difluorobenzo[d]isoxazol-3-yl)amino)propyl)acetylthio (I-4-4)

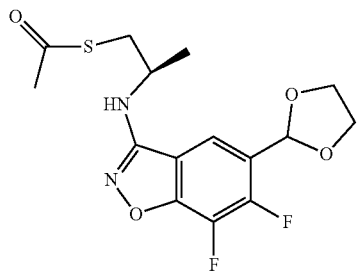 [SMILES: CC(=O)SC[C@@H](C)Nc1noc2c(F)c(F)c(C3OCCO3)cc12]

According to the synthesis method of S-(2-((5-(1,3-dioxolan-2-yl)-6,7-difluorobenzo[d]isoxazol-3-yl)amino) ethyl)acetylthio (I-4-1), an intermediate I-3-4 (560 mg, 1.866 mmol), triphenylphosphine (1.468 g, 5.598 mmol), diisopropyl azodicarboxylate (1.10 ml, 5.598 mmol) and thioacetic acid (0.398 ml, 5.598 mmol) were used as raw materials to prepare 600 mg of light yellow solid in a yield of 90%. $^1$H NMR (400 MHz, CDCl$_3$) δ 7.42 (dd, J=5.4, 1.5 Hz, 1H), 6.11 (s, 1H), 4.69 (d, J=7.0 Hz, 1H), 4.23-4.10 (m, 4H), 4.10-4.02 (m, 1H), 3.25 (qd, J=14.2, 5.8 Hz, 2H), 2.39 (s, 3H), 1.40 (d, J=6.5 Hz, 3H).

(c) (R)-3-(5-(1,3-dioxolan-2-yl)-6,7-difluorobenzo[d]isoxazol-3-yl)-4-methylthiazolin-2-one (I-6-4)

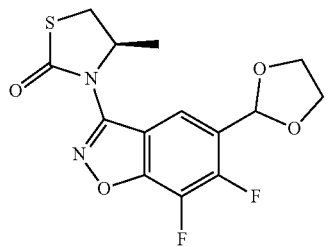 [SMILES: C[C@@H]1CSC(=O)N1c1noc2c(F)c(F)c(C3OCCO3)cc12]

According to the synthesis method of 3-(5-(1,3-dioxolan-2-yl)-6,7-difluorobenzo[d]isoxazol-3-yl)tetrahydrothiazol-2-one (I-6-1), an intermediate I-4-4 (710 mg, 1.983 mmol), sodium hydroxide (119 mg, 2.975 mmol), dithiothreitol (306 mg, 1.983 mmol), N,N-carbonyl diimidazole (642 mg, 3.966 mmol), and 4-dimethylaminopyridine (242 mg, 1.983 mmol) were used as raw materials to prepare 481 mg of white solid in a yield of 71%. $^1$H NMR (400 MHz, CDCl$_3$) δ 8.09 (dd, J=5.9, 1.8 Hz, 1H), 6.15 (s, 1H), 4.89-4.81 (m, 1H), 4.22-4.07 (m, 4H), 3.82 (dd, J=11.0, 7.2 Hz, 1H), 3.15 (dd, J=11.0, 3.6 Hz, 1H), 1.65 (d, J=6.2 Hz, 3H).

(d) (R)-6,7-difluoro-3-(4-methyl-2-oxothiazolin-3-yl)benzo[d]isoxazole-5-carbaldehyde (I-7-4)

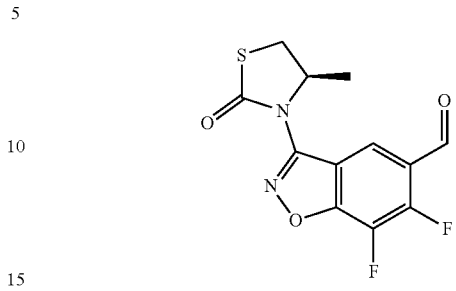

According to the synthesis method of 6,7-difluoro-3-(2-oxothiazolin-3-yl)benzo[d]isoxazole-5-carbaldehyde (I-7-1), an intermediate I-6-4 (475 mg, 1.389 mmol) and 6 M hydrochloric acid (15 ml) were used as raw materials to prepare 400 mg of white solid in a yield of 97%. $^1$H NMR (400 MHz, CDCl$_3$) δ 10.29 (s, 1H), 8.54 (dd, J=5.8, 1.8 Hz, 1H), 4.90-4.82 (m, 1H), 3.85 (dd, J=11.1, 7.2 Hz, 1H), 3.17 (dd, J=11.1, 3.3 Hz, 1H), 1.67 (d, J=6.2 Hz, 3H).

(e) 6-((2R,6R)-2,6-dimethylmorpholine)-7-fluoro-3-((R)-4-methyl-2-oxothiazolin-3-yl)benzo[d]isoxazole-5-carbaldehyde (I-8-4)

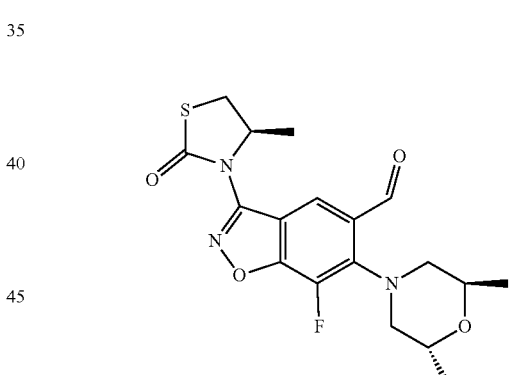

According to the synthesis method of 6-((2R,6R)-2,6-dimethylmorpholine)-7-fluoro-3-(2-oxothiazolin-3-yl) benzo[d]isoxazole-5-carbaldehyde (I-8-1), an intermediate I-7-4 (100 mg, 0.336 mmol), 2R,6R-dimethylmorpholine (0.104 ml, 0.839 mmol), and N,N-diisopropyl ethylamine (0.179 ml, 1.007 mmol) were used as raw materials to prepare 94 mg of light yellow solid in a yield of 71%. $^1$H NMR (400 MHz, CDCl$_3$) δ 10.41 (s, 1H), 8.40 (s, 1H), 4.88-4.80 (m, 1H), 4.29-4.21 (m, 2H), 3.83 (dd, J=11.1, 7.2 Hz, 1H), 3.43 (d, J=12.1 Hz, 2H), 3.16 (dd, J=11.0, 3.4 Hz, 1H), 3.05 (dd, J=11.9, 5.7 Hz, 2H), 1.65 (d, J=6.2 Hz, 3H), 1.34 (d, J=6.4 Hz, 6H).

(f) (2R,4S,4aS)-11-fluoro-2,4-dimethyl-8-((R)-4-methyl-2-oxothiazolin-3-yl)-1,2,4,4a-tetrahydro-2'H, 6H-spiro[isoxazole[4,5-g][1,4]oxazine[4,3-a]quinoline-5,5'-pyrimidine]-2',4',6'(1'H,3'H)-trione (Compound 4)

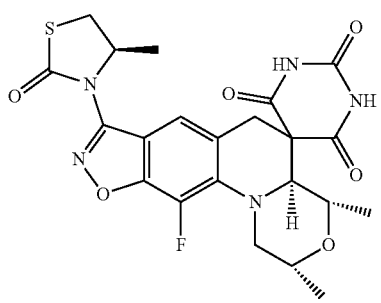

According to the synthesis method of compound 1, an intermediate I-8-4 (82 mg, 0.208 mmol) and barbituric acid (30 mg, 0.229 mmol) were used as raw materials to prepare 65 mg of white solid in a yield of 62%. $^1$H NMR (400 MHz, DMSO) δ 11.83 (s, 1H), 11.46 (s, 1H), 7.31 (s, 1H), 4.74-4.66 (m, 1H), 4.10 (d, J=12.6 Hz, 1H), 3.94 (d, J=8.8 Hz, 11H), 3.89 (dd, J=11.1, 7.1 Hz, 1H), 3.84-3.74 (m, 1H), 3.70-3.62 (m, 2H), 3.23 (dd, J=11.1, 2.9 Hz, 1H), 3.15-3.06 (m, 1H), 2.91 (d, J=13.8 Hz, 1H), 1.49 (d, J=6.3 Hz, 3H), 1.15 (d, J=6.3 Hz, 3H), 0.89 (d, J=6.3 Hz, 3H); $^{13}$C NMR (126 MHz, DMSO) δ 171.38, 171.23, 168.11, 153.74 (d, J=12.9 Hz), 153.43, 149.95, 135.31, 133.84 (d, J=239.3 Hz), 123.10, 118.09, 108.03, 72.57, 72.15, 64.82, 57.88, 56.75 (d, J=9.3 Hz), 53.35, 38.91, 34.43, 18.64, 18.61, 18.27. MS (EI) m/z: [M$^+$, 503].

Example 5: (2R,4S,4aS)-11-fluoro-2,4-dimethyl-8-((S)-4-methyl-2-oxothiazolin-3-yl)-1,2, 4,4a-tetrahydro-2'H,6H-spiro[isoxazole[4,5-g][1,4]oxazine[4, 3-a]quinoline-5,5'-pyrimidine]-2',4',6'(1'H,3'H)-trione (Compound 5)

(a) (S)-2-((5-(1,3-dioxolan-2-yl)-6,7-difluorobenzo[d]isoxazol-3-yl)amino)propanol (I-3-5)

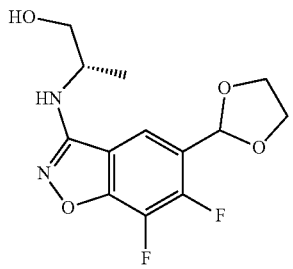 [SMILES: C[C@@H](CO)Nc1noc2c(F)c(F)c(C3OCCO3)cc12]

According to the synthesis method of intermediate I-3-1, an intermediate A (700 mg, 2.833 mmol), N-chlorosuccinimide (454 mg, 3.400 mmol), (S)-2-amino-1-propanol (0.800 ml, 8.499 mmol) and cesium carbonate (3.692 g, 11.332 mmol) were used as raw materials to prepare 600 mg of white solid in a yield of 71%. $^1$H NMR (400 MHz, DMSO) δ 8.01 (d, J=4.8 Hz, 1H), 7.13 (d, J=7.3 Hz, 1H), 6.09 (s, 1H), 4.81 (t, J=5.6 Hz, 1H), 4.11-4.01 (m, 4H), 3.62 (dt, J=12.5, 6.4 Hz, 1H), 3.54 (dt, J=10.6, 5.2 Hz, 1H), 3.47-3.39 (m, 1H), 1.21 (d, J=6.5 Hz, 3H).

(b) (S)—S-(2-((5-(1,3-dioxolan-2-yl)-6,7-difluorobenzo[d]isoxazol-3-yl)amino)propyl)acetylthio (I-4-5)

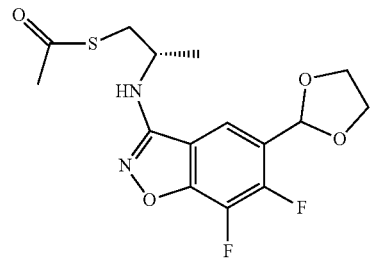 [SMILES: CC(=O)SC[C@H](C)Nc1noc2c(F)c(F)c(C3OCCO3)cc12]

According to the synthesis method of S-(2-((5-(1,3-dioxolan-2-yl)-6,7-difluorobenzo[d]isoxazol-3-yl)amino) ethyl)acetylthio (I-4-1), an intermediate I-3-5 (305 mg, 1.016 mmol), triphenylphosphine (533 mg, 2.033 mmol), diisopropyl azodicarboxylate (0.345 ml, 2.033 mmol) and thioacetic acid (0.145 ml, 2.033 mmol) were used as raw materials to prepare 268 mg of light yellow solid in a yield of 74%. $^1$H NMR (400 MHz, CDCl$_3$) 57.42 (dd, J=5.4, 1.5 Hz, 1H), 6.11 (s, 1H), 4.69 (d, J=7.0 Hz, 1H), 4.23-4.10 (m, 4H), 4.10-4.02 (m, 1H), 3.25 (qd, J=14.2, 5.8 Hz, 2H), 2.39 (s, 3H), 1.40 (d, J=6.5 Hz, 3H).

(c) (S)-3-(5-(1,3-dioxolan-2-yl)-6,7-difluorobenzo[d]isoxazol-3-yl)-4-methylthiazolin-2-one (I-6-5)

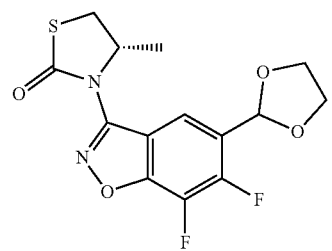 [SMILES: C[C@H]1CSC(=O)N1c1noc2c(F)c(F)c(C3OCCO3)cc12]

According to the synthesis method of 3-(5-(1,3-dioxolan-2-yl)-6,7-difluorobenzo[d]isoxazol-3-yl)tetrahydrothiazol-2-one (I-6-1), an intermediate I-4-5 (210 mg, 0.586 mmol), sodium hydroxide (35 mg, 0.879 mmol), dithiothreitol (90 mg, 0.586 mmol), N,N-carbonyl diimidazole (190 mg, 1.172 mmol), and 4-dimethylaminopyridine (71 mg, 0.586 mmol) were used as raw materials to prepare 130 mg of white solid in a yield of 65%. $^1$H NMR (400 MHz, CDCl$_3$) δ 8.09 (dd, J=5.9, 1.8 Hz, 1H), 6.15 (s, 1H), 4.89-4.81 (m, 1H), 4.22-4.07 (m, 4H), 3.82 (dd, J=11.0, 7.2 Hz, 1H), 3.15 (dd, J=11.0, 3.6 Hz, 11H), 1.65 (d, J=6.2 Hz, 3H).

(d) (S)-6,7-difluoro-3-(4-methyl-2-oxothiazolin-3-yl)benzo[d]isoxazole-5-carbaldehyde (I-7-5)

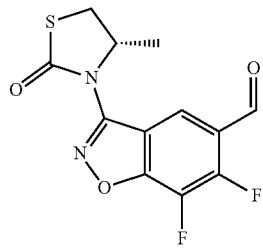 [SMILES: C[C@H]1CSC(=O)N1c1noc2c(F)c(F)c(C=O)cc12]

According to the synthesis method of 6,7-difluoro-3-(2-oxothiazolin-3-yl)benzo[d]isoxazole-5-carbaldehyde (I-7-1), an intermediate I-6-5 (332 mg, 0.970 mmol) and 6M hydrochloric acid (15 ml) were used as raw materials to prepare 276 mg of white solid in a yield of 95%. $^1$H NMR (400 MHz, CDCl$_3$) δ 10.29 (s, 1H), 8.54 (dd, J=5.8, 1.8 Hz, 1H), 4.90-4.82 (m, 1H), 3.85 (dd, J=11.1, 7.2 Hz, 1H), 3.17 (dd, J=11.1, 3.3 Hz, 1H), 1.67 (d, J=6.2 Hz, 3H).

(e) 6-((2R,6R)-2,6-dimethylmorpholine)-7-fluoro-3-((S)-4-methyl-2-oxothiazolin-3-yl)benzo[d]isoxazole-5-carbaldehyde (I-8-5)

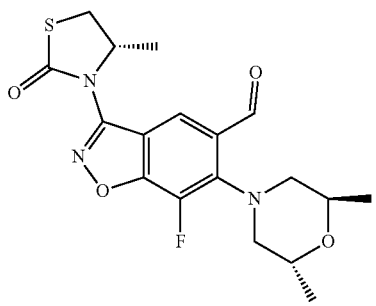 [SMILES: C[C@@H]1CN(c2c(C=O)cc3c(N4C(=O)SC[C@@H]4C)noc3c2F)C[C@@H](C)O1]

According to the synthesis method of 6-((2R,6R)-2,6-dimethylmorpholine)-7-fluoro-3-(2-oxothiazolin-3-yl)benzo[d]isoxazole-5-carbaldehyde (I-8-1), an intermediate I-7-5 (100 mg, 0.336 mmol), 2R,6R-dimethylmorpholine (0.104 ml, 0.839 mmol), and N,N-diisopropyl ethylamine (0.179 ml, 1.007 mmol) were used as raw materials to prepare 115 mg of light yellow solid in a yield of 87%. $^1$H NMR (400 MHz, CDCl$_3$) δ 10.40 (s, 1H), 8.39 (s, 1H), 4.88-4.80 (m, 1H), 4.29-4.21 (m, 2H), 3.83 (dd, J=11.0, 7.2 Hz, 1H), 3.43 (d, J=11.8 Hz, 2H), 3.16 (dd, J=11.0, 3.5 Hz, 1H), 3.05 (dd, J=12.0, 5.9 Hz, 2H), 1.65 (d, J=6.2 Hz, 3H), 1.34 (d, J=6.4 Hz, 6H).

(f) (2R,4S,4aS)-11-fluoro-2,4-dimethyl-8-((S)-4-methyl-2-oxothiazolin-3-yl)-1,2,4,4a-tetrahydro-2'H,6H-spiro[isoxazole[4,5-g][1,4]oxazine[4,3-a]quinoline-5,5'-pyrimidine]-2',4',6'(1'H,3'H)-trione (Compound 5)

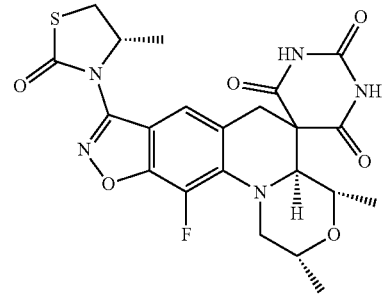

According to the synthesis method of compound 1, an intermediate I-8-5 (97 mg, 0.248 mmol) and barbituric acid (35 mg, 0.271 mmol) were used as raw materials to prepare 80 mg of white solid in a yield of 64%. $^1$H NMR (400 MHz, DMSO) δ 11.83 (s, 1H), 11.52 (s, 1H), 7.33 (s, 1H), 4.76-4.66 (m, 1H), 4.10 (d, J=13.0 Hz, 1H), 3.94 (d, J=8.8 Hz, 1H), 3.86 (dd, J=11.1, 7.2 Hz, 1H), 3.82-3.74 (m, 1H), 3.71-3.59 (m, 2H), 3.25 (dd, J=11.2, 3.9 Hz, 1H), 3.16-3.06 (m, 1H), 2.91 (d, J=14.4 Hz, 1H), 1.46 (d, J=6.2 Hz, 3H), 1.15 (d, J=6.3 Hz, 3H), 0.89 (d, J=6.3 Hz, 3H); $^{13}$C NMR (126 MHz, DMSO) δ 171.44, 171.38, 168.19, 153.79 (d, J=12.8 Hz), 153.34, 149.93, 135.25, 133.75 (d, J=239.3 Hz), 123.09, 118.11, 108.07, 72.59, 72.15, 64.84, 57.53, 56.74 (d, J=9.8 Hz), 53.33, 38.95, 34.21, 18.64, 18.60, 18.40; MS (EI) m/z: [M$^+$, 503].

Example 6: (2R,4S,4aS)-11-fluoro-8-((R)-5-(fluoromethyl)-2-oxothiazolin-3-yl)-2,4-dimethyl-1,2,4,4a-tetrahydro-2'H,6H-spiro[isoxazole[4,5-g][1,4]oxazine[4,3-a]quinoline-5,5'-pyrimidine]-2',4',6'(1'H,3'H)-trione (Compound 6)

(a) (S)-3-((5-(1,3-dioxolan-2-yl)-6,7-difluorobenzo[d]isoxazol-3-yl)amino)-1,2-propanediol (I-3-6)

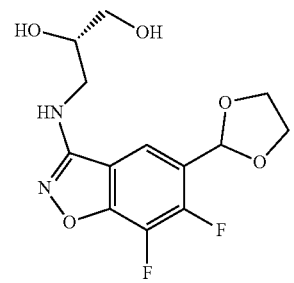 [SMILES: OC[C@@H](O)CNc1noc2c(F)c(F)c(C3OCCO3)cc12]

According to the synthesis method of intermediate I-3-1, an intermediate A (2.500 g, 10.119 mmol), N-chlorosuccinimide (1.620 g, 12.143 mmol), (S)-3-amino-1,2-propanediol (2.030 g, 22.263 mmol) and cesium carbonate (16.000 g, 50.600 mmol) were used as raw materials to prepare 2.460 g of white solid in a yield of 77%. $^1$H NMR (400 MHz, DMSO) δ 8.04 (d, J=5.7 Hz, 11H), 7.30 (t, J=5.7 Hz, 11H), 6.09 (s, 11H), 4.86 (d, J=5.1 Hz, 1H), 4.61 (t, J=5.8 Hz, 11H), 4.12-4.00 (m, 4H), 3.81-3.72 (m, 1H), 3.44-3.35 (m, 3H), 3.17-3.09 (m, 1H).

(b) (S)-1-((5-(1,3-dioxolan-2-yl)-6,7-difluorobenzo[d]isoxazol-3-yl)amino)-3-((tert-butyl dimethylsilyl)oxy)isopropanol (I-4-6)

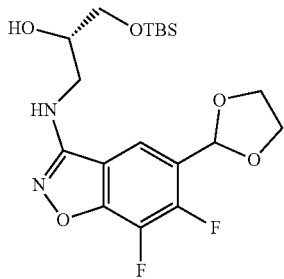 [SMILES: CC(C)(C)[Si](C)(C)OC[C@@H](O)CNc1noc2c(F)c(F)c(C3OCCO3)cc12]

Compound I-3-6 (2.65 g, 8.379 mmol) was added into 20 ml of N,N-dimethylformamide at room temperature and stirred to dissolve. Tert-butyldimethylsilyl chloride (1.515 g, 10.055 mmol) and imidazole (2.28 g, 33.516 mmol) were slowly added successively under a condition ofice bath. The mixture were warmed to room temperature and stirred for 2 h. The reaction completion was monitored by TLC. Water was added and the mixture was extracted with ethyl acetate. The combined organic layers were washed with water and saturated brine, dried over anhydrous sodium sulfate, concentrated under reduced pressure and purified by column chromatography [petroleum ether:ethyl acetate, 2:1] to 3.41 g of colorless oil in a yield of 95%. $^1$H NMR (400 MHz, CDCl$_3$) δ 7.49 (d, J=5.1 Hz, 1H), 6.12 (s, 1H), 4.87 (s, 1H), 4.22-4.08 (m, 4H), 4.02 (s, 1H), 3.80 (dd, J=10.0, 3.9 Hz, 1H), 3.70-3.58 (m, 2H), 3.45-3.37 (m, 1H), 2.75 (s, 1H), 0.95 (s, 9H), 0.13 (s, 6H).

(c) (R)—S-(1-((5-(1,3-dioxolan-2-yl)-6,7-difluorobenzo[d]isoxazol-3-yl)amino)-3-((tert-butyldimethylsilyl)oxy)isopropyl) acetylthio (I-5-6)

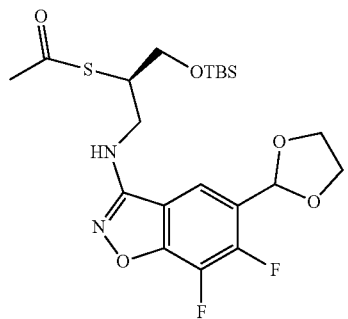 [SMILES: CC(=O)S[C@H](CNc1noc2c(F)c(F)c(C3OCCO3)cc12)CO[Si](C)(C)C(C)(C)C]

According to the synthesis method of S-(2-((5-(1,3-dioxolan-2-yl)-6,7-difluorobenzo[d]isoxazol-3-yl)amino)ethyl)acetylthio (I-4-1), an intermediate I-4-6 (3.14 g, 7.294 mmol), triphenylphosphine (6.696 g, 25.529 mmol), diisopropyl azodicarboxylate (5.162 ml, 25.529 mmol) and thioacetic acid (1.82 ml, 25.529 mmol) were used as raw materials to prepare 3.30 g of light yellow solid in a yield of 92%. $^1$H NMR (400 MHz, CDCl$_3$) δ 7.44 (d, J=5.3 Hz, 1H), 6.11 (s, 1H), 5.17 (t, J=5.1 Hz, 1H), 4.22-4.07 (m, 4H), 4.05-3.94 (m, 2H), 3.89-3.77 (m, 2H), 3.74-3.67 (m, 1H), 2.38 (s, 3H), 0.95 (s, 9H), 0.13 (d, J=2.1 Hz, 6H).

(d) (R)-3-(5-(1,3-dioxolan-2-yl)-6,7-difluorobenzo[d]isoxazol-3-yl)-5-(((tert-butyldimethylsilyl)oxy)methyl)thiazol-2-one (I-7-6)

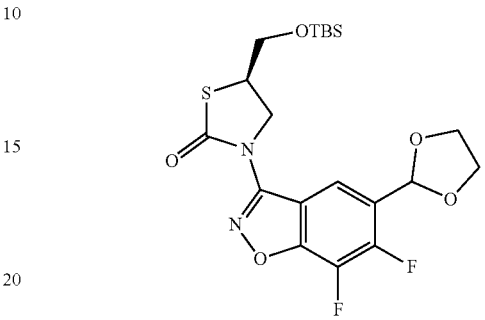

According to the synthesis method of 3-(5-(1,3-dioxolan-2-yl)-6,7-difluorobenzo[d]isoxazol-3-yl)tetrahydrothiazol-2-one (I-6-1), an intermediate I-5-6 (3.30 g, 6.754 mmol), sodium hydroxide (405 mg, 10.131 mmol), dithiothreitol (1.042 g, 6.754 mmol), N,N-carbonyl diimidazole (2.188 g, 13.508 mmol), and 4-dimethylaminopyridine (825 mg, 6.754 mmol) were used as raw materials to prepare 2.00 g of colorless oil in a yield of 63%. $^1$H NMR (400 MHz, CDCl$_3$) δ 8.20 (d, J=5.9 Hz, 1H), 6.15 (s, 1H), 4.37 (dd, J=11.2, 7.2 Hz, 1H), 4.27 (dd, J=11.2, 3.8 Hz, 1H), 4.23-4.06 (m, 5H), 4.04-3.95 (m, 1H), 3.88 (d, J=7.2 Hz, 2H), 0.90 (s, 9H), 0.09 (s, 6H).

(e) (R)-3-(5-(1,3-dioxolan-2-yl)-6,7-difluorobenzo[d]isoxazol-3-yl)-5-(hydroxymethyl)thiazol-2-one (I-8-6)

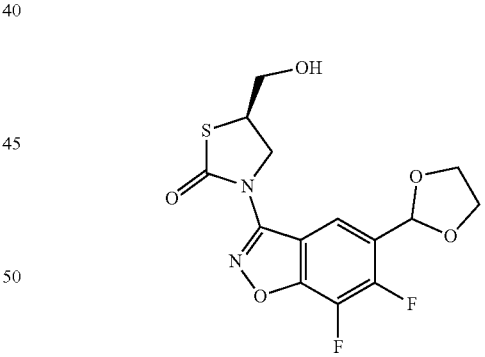

Compound I-7-6 (1.90 g, 4.020 mmol) was added into 15 ml of tetrahydrofuran at room temperature and stirred to dissolve. 1 M tetrabutylammonium fluoride solution (in tetrahydrofuran) (4.42 ml, 4.423 mmol) was slowly added dropwise in an ice bath and reacted for 10 min. The reaction completion was monitored by TLC. Water was added and the mixture was extracted with ethyl acetate. The combined organic layers were washed with water and saturated brine, dried over anhydrous sodium sulfate, concentrated under reduced pressure and purified by column chromatography [petroleum ether:ethyl acetate. 3:2] to obtain 1.123 g of colorless oil in a yield of 78%. $^1$H NMR (400 MHz, CDCl$_3$) δ 8.19 (dd, J=5.9, 1.8 Hz, 1H), 6.15 (s, 1H), 4.42 (dd, J=11.3, 7.3 Hz, 1H), 4.29 (dd, J=11.3, 3.9 Hz, 1H), 4.22-4.05 (m, 5H), 3.95 (t, J=5.6 Hz, 2H), 2.09 (t, J=5.7 Hz, 1H).

(f) (R)-3-(5-(1,3-dioxolan-2-yl)-6,7-difluorobenzo[d]isoxazol-3-yl)-5-(fluoromethyl)thiazol-2-one (I-9-6)

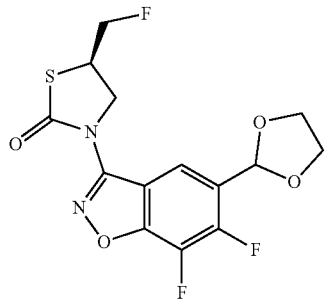 [SMILES: O=C1S[C@@H](CF)CN1c1noc2c(F)c(F)c(C3OCCO3)cc12]

Compound I-8-6 (250 mg, 0.698 mmol) was added into 10 ml of tetrahydrofuran at room temperature and stirred to dissolve. Diethylamino sulfur trifluoride (0.41 ml, 2.793 mmol) was slowly added dropwise in an ice bath. The mixture was warmed to 35° C. and reacted for 1 h. The reaction completion was monitored by TLC. Water was added and the mixture was extracted with ethyl acetate. The combined organic layers were washed with water and saturated brine, dried over anhydrous sodium sulfate, concentrated under reduced pressure and purified by column chromatography [petroleum ether:ethyl acetate 3:1] to obtain 185 mg of colorless oil in a yield of 74%. $^1$H NMR (400 MHz, CDCl$_3$) δ 8.17 (dd, J=5.9, 1.8 Hz, 1H), 6.15 (s, 1H), 4.71-4.68 (m, 1H), 4.60-4.56 (m, 1H), 4.46 (dd, J=11.5, 7.2 Hz, 1H), 4.34 (dd, J=11.5, 3.1 Hz, 1H), 4.22-4.07 (m, 5H).

(g) (R)-6,7-difluoro-3-(5-(fluoromethyl)-2-oxothiazol-3-yl)benzo[d]isoxazole-5-carbaldehyde (I-10-6)

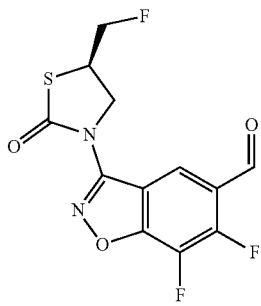 [SMILES: O=Cc1cc2c(N3C[C@H](CF)SC3=O)noc2c(F)c1F]

According to the synthesis method of 6,7-difluoro-3-(2-oxothiazolin-3-yl)benzo[d]isoxazole-5-carbaldehyde (I-7-1), an intermediate I-9-6 (180 mg, 0.500 mmol) and 6M hydrochloric acid (15 ml) were used as raw materials to prepare 150 mg of colorless oil in a yield of 95%. $^1$H NMR (400 MHz, CDCl$_3$) δ 10.31 (s, 1H), 8.61 (dd, J=5.8, 1.6 Hz, 1H), 4.75-4.66 (m, 1H), 4.63-4.55 (m, 1H), 4.47 (dd, J=11.6, 7.2 Hz, 1H), 4.36 (dd, J=11.6, 3.2 Hz, 1H), 4.27-4.15 (m, 1H).

(h) 6-((2R,6R)-2,6-dimethylmorpholine)-7-fluoro-3-((R)-5-(fluoromethyl)-2-oxothiazol-3-yl)benzo[d]isoxazole-5-carbaldehyde (I-11-6)

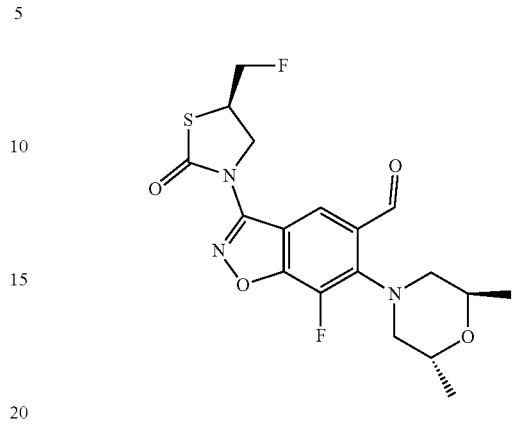

According to the synthesis method of 6-((2R,6R)-2,6-dimethylmorpholine)-7-fluoro-3-(2-oxothiazolin-3-yl)benzo[d]isoxazole-5-carbaldehyde (I-8-1), an intermediate I-10-6 (160 mg, 0.506 mmol), 2R,6R-dimethylmorpholine (0.134 ml, 1.013 mmol), and N,N-diisopropyl ethylamine (0.173 ml, 1.007 mmol) were used as raw materials to prepare 122 mg of light yellow solid in a yield of 59%. $^1$H NMR (400 MHz, CDCl$_3$) δ 10.40 (s, 1H), 8.47 (s, 1H), 4.70 (dd, J=6.7, 3.6 Hz, 1H), 4.58 (dd, J=6.8, 4.1 Hz, 1H), 4.45 (dd, J=11.6, 7.1 Hz, 11H), 4.34 (dd, J=11.5, 2.8 Hz, 1H), 4.29-4.23 (m, 2H), 4.21-4.13 (m, 1H), 3.44 (d, J=11.8 Hz, 2H), 3.05 (dd, J=11.8, 5.7 Hz, 2H), 1.34 (d, J=6.4 Hz, 6H).

(i) (2R,4S,4aS)-11-fluoro-8-((R)-5-(fluoromethyl)-2-oxothiazolin-3-yl)-2,4-dimethyl-1,2,4,4a-tetrahydro-2'H,6H-spiro[isoxazole[4,5-g][1,4]oxazine[4,3-a]quinoline-5,5'-pyrimidine]-2',4',6'(1'H,3'H)-trione (Compound 6)

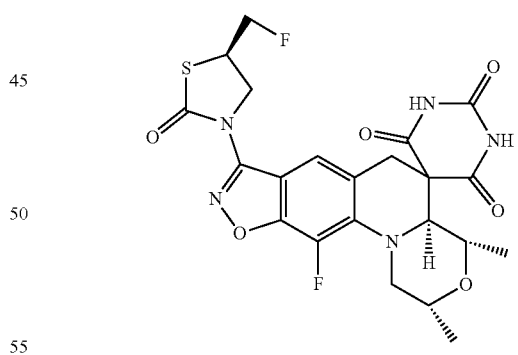

According to the synthesis method of compound 1, an intermediate I-11-6 (110 mg, 0.268 mmol) and barbituric acid (41 mg, 0.321 mmol) were used as raw materials to prepare 90 mg of white solid in a yield of 65%. $^1$H NMR (400 MHz, DMSO) δ 11.83 (s, 1H), 11.49 (s, 1H), 7.46 (s, 1H), 4.78 (d, J=5.6 Hz, 1H), 4.66 (d, J=4.0 Hz, 1H), 4.43-4.35 (m, 2H), 4.16-4.08 (m, 2H), 3.94 (d, J=8.8 Hz, 1H), 3.83-3.75 (m, 1H), 3.70-3.62 (m, 2H), 3.15-3.07 (m, 1H), 2.91 (d, J=13.9 Hz, 1H), 1.15 (d, J=6.2 Hz, 3H), 0.89 (d, J=6.4 Hz, 3H); $^{13}$C NMR (126 MHz, DMSO) δ 171.39, 170.44, 168.15, 154.08 (d, J=12.7 Hz), 153.80, 149.96, 135.28, 133.69 (d, J=239.0 Hz), 122.91, 118.77, 107.17, 84.17 (d, J=171.1 Hz), 72.58, 72.13, 64.85, 56.73 (d, J=10.0 Hz), 53.33, 50.77 (d, J=5.9 Hz), 41.86 (d, J=20.6 Hz), 38.97, 18.64, 18.61; MS(ESI) m/z: [(M−1)⁻, 520.0].

Example 7: (2R,4S,4aS)-11-fluoro-8-((R)-5-(hydroxymethyl)-2-oxothiazolin-3-yl)-2,4-di methyl-1, 2,4,4a-tetrahydro-2'H,6H-spiro[isoxazole[4,5-g][1,4]oxazine[4,3-a]quinoline-5,5'-pyrimidine]-2',4',6'(1'H, 3'H)-trione (Compound 7)

(a) (R)-6,7-difluoro-3-(5-(hydroxymethyl)-2-oxothiazol-3-yl)benzo[d]isoxazole-5-carbaldehyde (I-3-7)

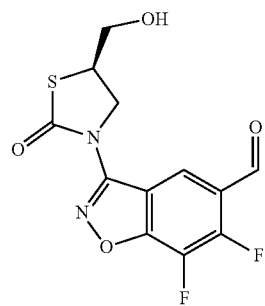 [SMILES: O=Cc1cc2c(N3C[C@H](CO)SC3=O)noc2c(F)c1F]

According to the synthesis method of 6,7-difluoro-3-(2-oxothiazolin-3-yl)benzo[d]isoxazole-5-carbaldehyde (I-7-1), an intermediate (R)-3-(5-(1,3-dioxolan-2-yl)-6,7-difluorobenzo[d]isoxazol-3-yl)-5-(((tert-butyldimethylsilyl)oxy)methyl)thiazol-2-one (I-7-6) (350 mg, 0.740 mmol) and 6M hydrochloric acid (10 ml) were used as raw materials to prepare 173 mg of white solid in a yield of 74%. ¹H NMR (400 MHz, CDCl₃) δ 10.30 (s, 1H), 8.63 (d, J=5.5 Hz, 1H), 4.42 (dd, J=11.4, 7.6 Hz, 1H), 4.31 (dd, J=11.3, 3.8 Hz, 1H), 4.13-4.05 (m, 1H), 3.99-3.93 (s, 2H), 2.24 (br, 1H).

(b) 6-((2R,6R)-2,6-dimethylmorpholine)-7-fluoro-3-((R)-5-(hydroxymethyl)-2-oxothiazol-3-yl)benzo[d]isoxazole-5-carbaldehyde (I-4-7)

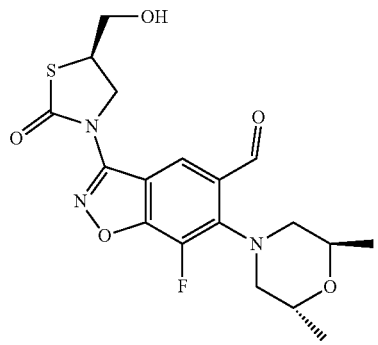 [SMILES: C[C@@H]1CN(c2c(C=O)cc3c(N4C[C@H](CO)SC4=O)noc3c2F)C[C@@H](C)O1]

According to the synthesis method of 6-((2R,6R)-2,6-dimethylmorpholine)-7-fluoro-3-(2-oxothiazolin-3-yl)benzo[d]isoxazole-5-carbaldehyde (I-8-1), an intermediate I-3-7 (317 mg, 1.009 mmol), 2R,6R-dimethylmorpholine (0.372 ml, 3.026 mmol), and N,N-diisopropyl ethylamine (0.500 ml, 3.026 mmol) were used as raw materials to prepare 227 mg of light yellow solid in a yield of 55%. ¹H NMR (400 MHz, DMSO) δ 10.31 (s, 1H), 8.36 (s, 1H), 5.42 (br, 1H), 4.35 (dd, J=11.9, 8.7 Hz, 1H), 4.18-4.09 (m, 4H), 3.76-3.64 (m, 2H), 3.39 (d, J=7.7 Hz, 2H), 3.01 (dd, J=11.7, 5.4 Hz, 2H), 1.22 (d, J=6.4 Hz, 6H).

(c) (2R,4S,4aS)-11-fluoro-8-((R)-5-(hydroxymethyl)-2-oxothiazolin-3-yl)-2,4-dimethyl-1, 2,4,4a-tetrahydro-2'H,6H-spiro[isoxazole[4,5-g][1,4]oxazine[4,3-a]quinoline-5,5'-pyrimidine]-2',4',6'(1'H, 3'H)-trione (Compound 7)

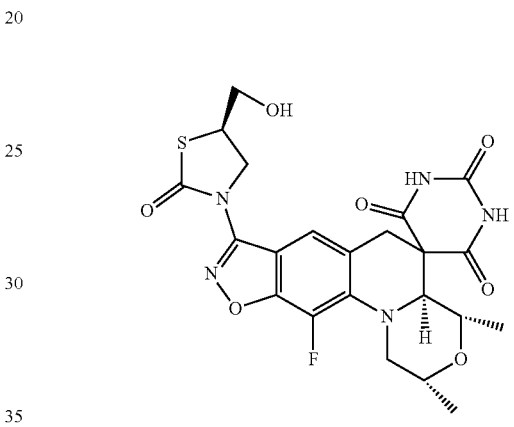

An intermediate I-4-7 (104 mg, 0.254 mmol) and barbituric acid (36 mg, 0.279 mmol) were added into a mixed solvent of 3 ml ethanol and 1 ml of 6M hydrochloric acid at room temperature and stirred to dissolve. The mixture was warmed to 100° C. and reacted for 4 h. The reaction completion was monitored by TLC. The mixture was cooled to room temperature, water was added and the mixture was extracted with ethyl acetate. The combined organic layers were washed with water and saturated brine, dried over anhydrous sodium sulfate, concentrated under reduced pressure and prepared by reversed-phase column [acetonitrile:water=50:50] to obtain 95 mg of white solid in a yield of 72%. ¹H NMR (400 MHz, DMSO) δ 11.83 (s, 1H), 11.49 (s, 1H), 7.44 (s, 1H), 5.43 (t, J=5.4 Hz, 1H), 4.28 (dd, J=9.5, 6.2 Hz, 1H), 4.16-4.05 (m, 3H), 3.93 (d, J=8.8 Hz, 1H), 3.83-3.74 (m, 1H), 3.73-3.58 (m, 4H), 3.16-3.06 (m, 1H), 2.91 (d, J=14.3 Hz, 1H), 1.14 (d, J=6.1 Hz, 3H), 0.89 (d, J=6.3 Hz, 3H); ¹³C NMR (126 MHz, DMSO) δ 171.39, 171.27, 168.15, 154.07, 153.95, 149.97, 135.24, 133.74 (d, J=238.9 Hz), 122.83, 118.75, 107.30, 72.57, 72.13, 64.84, 63.45, 56.73 (d, J=8.9 Hz), 53.36, 51.40, 45.07, 38.99, 18.64, 18.61; MS (EI) m/z: [M⁺, 519].

Example 8: (2R,4S,4aS)-11-fluoro-8-((R)-5-(methoxymethyl)-2-oxothiazolin-3-yl)-2,4-di methyl-1,2,4,4a-tetrahydro-2'H,6H-spiro[isoxazole [4,5-g][1,4]oxazine[4,3-a]quinoline-5,5'-pyrimidine]-2',4',6'(1'H,3'H)-trione (Compound 8)

(a) (R)-6,7-difluoro-3-(5-(methoxymethyl)-2-oxothiazol-3-yl)benzo[d]isoxazole-5-carbaldehyde (I-3-8)

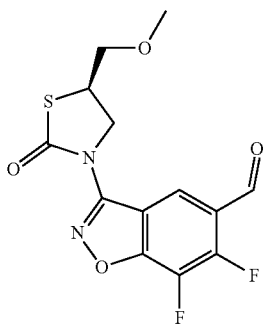 [SMILES: COC[C@H]1CN(c2noc3c(F)c(F)c(C=O)cc23)C(=O)S1]

An intermediate (R)-6,7-difluoro-3-(5-(hydroxymethyl)-2-oxothiazol-3-yl)benzo[d]isoxazole-5-carbaldehyde (I-3-7) (100 mg, 0.318 mmol) was added into 10 ml dichloromethane at room temperature. 2,6-di-tert-butylpyridine (0.536 ml, 2.387 mmol) and trimethyloxonium tetrafluoroborate (235 mg, 1.591 mmol) were added successively and stirred for 4 h. The reaction completion was monitored by TLC. Water was added and the mixture was extracted with dichloromethane. The combined organic layers were washed with water and saturated brine, dried over anhydrous sodium sulfate, concentrated under reduced pressure and purified by column chromatography [petroleum ether:ethyl acetate] to give 103 mg of white solid in a yield of 95%. $^1$H NMR (400 MHz, CDCl$_3$) δ 10.30 (s, 1H), 8.63 (dd, J=5.8, 1.8 Hz, 1H), 4.39 (dd, J=11.3, 7.4 Hz, 1H), 4.25 (dd, J=11.3, 4.4 Hz, 1H), 4.12 (tdd, J=7.4, 6.1, 4.4 Hz, 1H), 3.69 (ddd, J=15.8, 9.7, 6.8 Hz, 2H), 3.44 (s, 3H).

(b) 6-((2R,6R)-2,6-dimethylmorpholine)-7-fluoro-3-((R)-5-(methoxymethyl)-2-oxothiazol-3-yl)benzo[d]isoxazole-5-carbaldehyde (I-4-8)

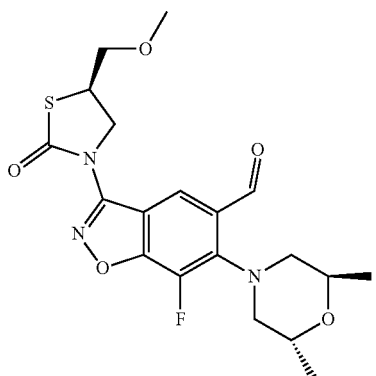 [SMILES: COC[C@H]1CN(c2noc3c(F)c(N4C[C@@H](C)O[C@H](C)C4)c(C=O)cc23)C(=O)S1]

According to the synthesis method of 6-((2R,6R)-2,6-dimethylmorpholine)-7-fluoro-3-(2-oxothiazolin-3-yl)benzo[d]isoxazole-5-carbaldehyde (I-8-1), an intermediate I-3-8 (98 mg, 0.299 mmol), 2R,6R-dimethylmorpholine (0.092 ml, 0.746 mmol), and N,N-diisopropylethylamine (0.148 ml, 0.896 mmol) were used as raw materials to prepare 65 mg of light yellow solid in a yield of 52%. $^1$H NMR (400 MHz, CDCl$_3$) δ 10.40 (s, 1H), 8.50 (d, J=1.1 Hz, 1H), 4.37 (dd, J=11.2, 7.3 Hz, 1H), 4.29-4.21 (m, 3H), 4.12-4.06 (m, 1H), 3.68 (ddd, J=15.8, 9.7, 6.9 Hz, 2H), 3.47-3.41 (m, 5H), 3.04 (dd, J=12.0, 5.7 Hz, 2H), 1.34 (d, J=6.5 Hz, 6H).

(c) (2R,4S,4aS)-11-fluoro-8-((R)-5-(methoxymethyl)-2-oxothiazolin-3-yl)-2,4-dimethyl-1, 2,4,4a-tetrahydro-2'H,6H-spiro[isoxazole[4,5-g][1,4] oxazine[4,3-a]quinoline-5,5'-pyrimidine]-2',4',6'(1'H, 3'H)-trione (Compound 8)

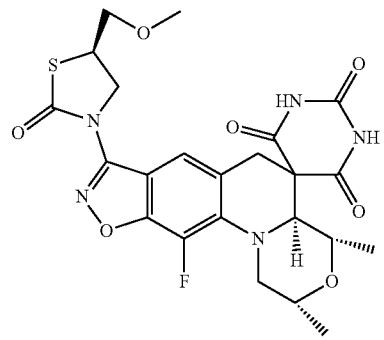

According to the synthesis method of compound 1, an intermediate I-4-8 (63 mg, 0.149 mmol) and barbituric acid (23 mg, 0.179 mmol) were used as raw materials to prepare 61 mg of white solid in a yield of 71%. $^1$H NMR (400 MHz, DMSO) δ 11.81 (s, 1H), 11.49 (s, 1H), 7.44 (s, 1H), 4.34-4.26 (m, 2H), 4.10 (d, J=12.6 Hz, 1H), 4.07-3.99 (m, 1H), 3.94 (d, J=8.8 Hz, 1H), 3.83-3.74 (m, 1H), 3.74-3.56 (m, 4H), 3.13 (s, 3H), 3.15-3.06 (m, 1H), 2.91 (d, J=14.0 Hz, 1H), 1.14 (d, J=6.2 Hz, 3H), 0.89 (d, J=6.4 Hz, 3H); $^{13}$C NMR (126 MHz, DMSO) δ 171.40, 170.99, 168.15, 154.04 (d, J=12.9 Hz), 153.89, 149.99, 135.27, 133.74 (d, J=239.0 Hz), 122.87, 118.72, 107.24, 73.87, 72.57, 72.13, 64.84, 58.90, 56.73 (d, J=9.0 Hz), 53.36, 51.45, 42.26, 38.98, 18.64, 18.61; MS (EI) m/z: [M$^+$, 533].

Example 9: (2R,4S,4aS)-11-fluoro-2,4-dimethyl-8-((R)-2-oxo-5-((trifluoromethoxy)methyl)thiazol-3-yl)-1,2,4,4a-tetrahydro-2'H,6H-spiro[isoxazole[4,5-g][1,4]oxazine[4,3-a]quinoline-5,5'-pyrimidine]-2',4',6'(1'H,3'H)-trione (Compound 9)

(a) (R)-3-(5-(1,3-dioxolan-2-yl)-6,7-difluorobenzo[d]isoxazol-3-yl)-5-((trifluoromethoxy) methyl)thiazol-2-one (I-3-9)

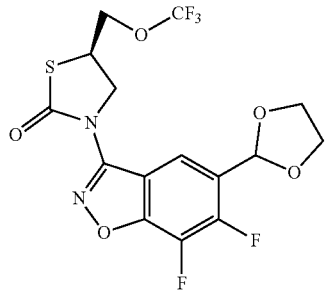 [SMILES: O=C1S[C@@H](COC(F)(F)F)CN1c1noc2c(F)c(F)c(C3OCCO3)cc12]

An intermediate (R)-3-(5-(1,3-dioxolan-2-yl)-6,7-difluorobenzo[d]isoxazol-3-yl)-5-(hydroxy methyl)thiazol-2-one (I-8-6) (449 mg, 1.253 mmol), silver trifluoromethanesulfonate (644 mg, 2.506 mmol), selective fluorine reagent (666 mg, 1.886 mmol), and potassium fluoride (218 mg, 3.759 mmol) were added successively into a reaction flask at room temperature. Under the protection of argon, 10 ml of ethyl acetate, 2-fluoropyridine (243 mg, 2.506 mmol) and trifluoromethyltrimethylsilane (356 mg, 2.506 mmol) were added and mixture was stirred at room temperature for 12 h. After the completion of reaction was monitored by TLC, the mixture was filtrated and concentrated under reduced pressure to obtain 60 mg of colorless oil in a yield of 12%. 11H NMR (400 MHz, CDCl$_3$) δ 8.17 (dd, J=5.8, 1.8 Hz, 11H), 6.15 (s, 11H), 4.48 (dd, J=11.7, 7.0 Hz, 1H), 4.33-4.07 (m, 8H).

(b) (R)-6,7-difluoro-3-(2-oxo-5-((trifluoromethoxy)methyl)thiazol-3-yl)benzo[d]isoxazole-5-carbaldehyde (I-4-9)

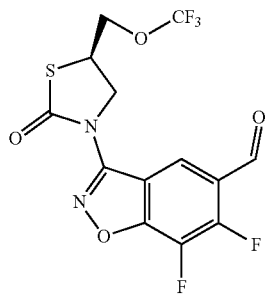 [SMILES: O=Cc1cc2c(N3C[C@H](COC(F)(F)F)SC3=O)noc2c(F)c1F]

According to the synthesis method of 6,7-difluoro-3-(2-oxothiazolin-3-yl)benzo[d]isoxazole-5-carbaldehyde (I-7-1), an intermediate I-3-9 (60 mg, 0.140 mmol) and 6M hydrochloric acid (3 ml) were used as raw materials to prepare 49 mg of colorless oil in a yield of 99%. $^1$H NMR (400 MHz, CDCl$_3$) δ 10.32 (s, 1H), 8.60 (dd, J=5.8, 1.8 Hz, 1H), 4.48 (dd, J=11.7, 6.6 Hz, 1H), 4.32 (dd, J=11.6, 2.9 Hz, 1H), 4.28-4.16 (m, 3H).

(c) 6-((2R,6R)-2,6-dimethylmorpholine)-7-fluoro-3-((R)-2-oxo-5-((trifluoromethoxy)methyl)thiazol-3-yl)benzo[d]isoxazole-5-carbaldehyde (I-5-9)

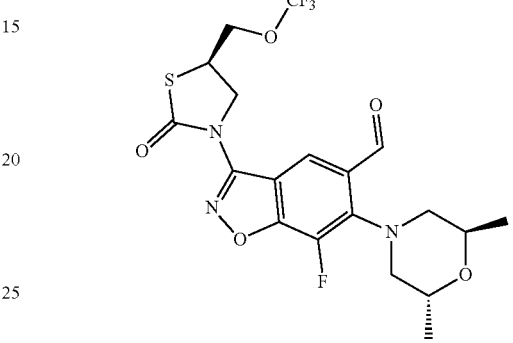

According to the synthesis method of 6-((2R,6R)-2,6-dimethylmorpholine)-7-fluoro-3-(2-oxothiazolin-3-yl)benzo[d]isoxazole-5-carbaldehyde (I-8-1), an intermediate I-4-9 (56 mg, 0.146 mmol), 2R,6R-dimethylmorpholine (0.054 ml, 0.439 mmol), and N,N-diisopropyl ethylamine (0.073 ml, 0.439 mmol) were used as raw materials to prepare 64 mg of light yellow solid in a yield of 91%. $^1$H NMR (400 MHz, CDCl$_3$) δ 10.40 (s, 1H), 8.46 (s, 1H), 4.46 (dd, J=11.7, 6.8 Hz, 1H), 4.33-4.14 (m, 6H), 3.45 (d, J=11.6 Hz, 2H), 3.06 (dd, J=12.0, 5.4 Hz, 2H), 1.34 (d, J=6.4 Hz, 6H).

(d) (2R,4S,4aS)-11-fluoro-2,4-dimethyl-8-((R)-2-oxo-5-((trifluoromethoxy)methyl)thiazol-3-yl)-1,2,4,4a-tetrahydro-2'H,6H-spiro[isoxazole[4,5-g][1,4]oxazine[4,3-a]quinoline-5,5'-pyrimidine]-2',4',6'(1'H,3'H)-trione (Compound 9)

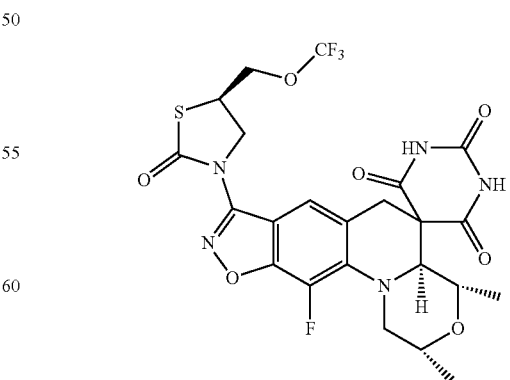

According to the synthesis method of compound 1, an intermediate I-5-9 (62 mg, 0.130 mmol) and barbituric acid (19 mg, 0.144 mmol) were used as raw materials to prepare 38 mg of white solid in a yield of 50%. $^1$H NMR (400 MHz, DMSO) δ 11.83 (s, 1H), 11.49 (s, 1H), 7.46 (s, 1H), 4.54-4.47 (m, 1H), 4.46-4.37 (m, 3H), 4.16-4.07 (m, 2H), 3.94 (d, J=8.7 Hz, 1H), 3.83-3.75 (m, 1H), 3.71-3.61 (m, 2H), 3.17-3.05 (m, 11H), 2.91 (d, J=14.2 Hz, 11H), 1.15 (d, J=6.1 Hz, 3H), 0.89 (d, J=6.3 Hz, 3H); $^{13}$C NMR (151 MHz, DMSO) δ 171.40, 170.22, 168.16, 154.07 (d, J=12.8 Hz), 153.78, 149.98, 135.29, 133.69 (d, J=239.0 Hz), 122.91, 121.58 (q, J=254.5 Hz), 118.80, 107.14, 72.58, 72.14, 69.42, 64.85, 56.73 (d, J=9.3 Hz), 53.33, 50.96, 40.94, 38.93, 18.65, 18.62; MS(EI) m/z: [M$^+$, 587].

Example 10: (2R,4S,4aS)-8-((R)-5-(azidomethyl)-2-oxothiazol-3-yl)-11-fluoro-2,4-dimethyl-1,2,4,4a-tetrahydro-2'H,6H-spiro[isoxazole[4,5-g][1,4]oxazine[4,3-a]quinoline-5,5'-pyrimidine]-2',4',6'(1'H,3'H)-trione (Compound 10)

(a) ((R)-3-(6-((2R,6R)-2,6-dimethylmorpholine)-7-fluoro-5-formylbenzo[d]isoxazol-3-yl)-2-oxothiazol-5-yl)methylmethanesulfonate (I-3-10)

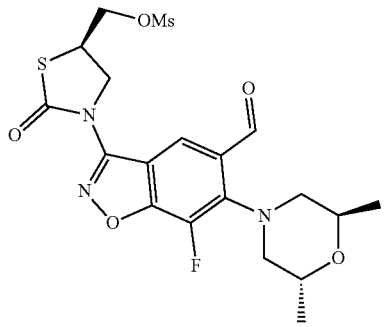 [SMILES: C[C@@H]1CN(c2c(C=O)cc3c(N4C[C@H](COS(C)(=O)=O)SC4=O)noc3c2F)C[C@@H](C)O1]

An intermediate 6-((2R,6R)-2,6-dimethylmorpholine)-7-fluoro-3-((R)-5-(hydroxymethyl)-2-oxothiazol-3-yl)benzo[d]isoxazole-5-carbaldehyde (I-4-7) (124 mg, 0.303 mmol) was dissolved in 8 ml of dichloromethane in an ice bath, N,N-diisopropylethylamine (98 mg, 0.757 mmol) was added. Under the protection of argon, methanesulfonyl chloride (0.035 ml, 0.454 mmol) was slowly added dropwise. After 10 min, TLC detection showed that the reaction was completed. The reaction was quenched with water and the mixture was extracted with ethyl acetate, washed with water and saturated brine, dried over anhydrous sodium sulfate, concentrated under reduced pressure and purified by column chromatography [dichloromethane:ethyl acetate=6:1] to give 128 mg of yellow solid in a yield of 88%. $^1$H NMR (400 MHz, CDCl$_3$) δ 10.40 (s, 1H), 8.44 (d, J=1.1 Hz, 1H), 4.53-4.42 (m, 3H), 4.33 (dd, J=11.7, 2.9 Hz, 1H), 4.30-4.20 (m, 3H), 3.48-3.40 (m, 2H), 3.12 (s, 3H), 3.06 (dd, J=12.0, 4.5 Hz, 2H), 1.34 (d, J=6.5 Hz, 6H).

(b) 3-((R)-5-(azidomethyl)-2-oxothiazol-3-yl)-6-((2R,6R)-2,6-dimethylmorpholine)-7-fluorobenzo[d]isoxazole-5-carbaldehyde (I-4-10)

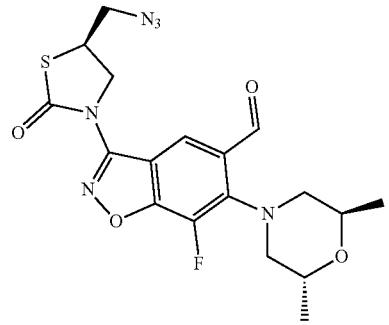 [SMILES: C[C@@H]1CN(c2c(C=O)cc3c(N4C[C@H](CN=[N+]=[N-])SC4=O)noc3c2F)C[C@@H](C)O1]

An intermediate I-3-10 (195 mg, 0.400 mmol) were added into 15 ml N,N-dimethylformamide at room temperature. Sodium azide (29 mg, 0.440 mmol) was added, the mixture was warmed to 70° C. and reacted for 10 h. After the completion of reaction was monitored by TLC, the mixture was cooled to room temperature. Water was added and the mixture was extracted with ethyl acetate. The mixture was washed with water and saturated brine, dried over anhydrous sodium sulfate, concentrated under reduced pressure and purified by column chromatography [petroleum ether:ethyl acetate=4:1] to give 156 mg of white solid in a yield of 90%. $^1$H NMR (400 MHz, CDCl$_3$) δ 10.40 (s, 1H), 8.47 (d, J=1.1 Hz, 1H), 4.42 (dd, J=11.5, 7.3 Hz, 1H), 4.30-4.18 (m, 3H), 4.08-4.01 (m, 1H), 3.82-3.71 (m, 2H), 3.44 (d, J=12.0 Hz, 2H), 3.05 (dd, J=12.1, 4.8 Hz, 2H), 1.34 (d, J=6.5 Hz, 6H).

(c) (2R,4S,4aS)-8-((R)-5-(azidomethyl)-2-oxothiazol-3-yl)-11-fluoro-2,4-dimethyl-1,2,4,4a-tetrahydro-2'H,6H-spiro[isoxazole[4,5-g][1,4]oxazine[4,3-a]quinoline-5,5'-pyrimidine]-2',4',6'(1'H,3'H)-trione (Compound 10)

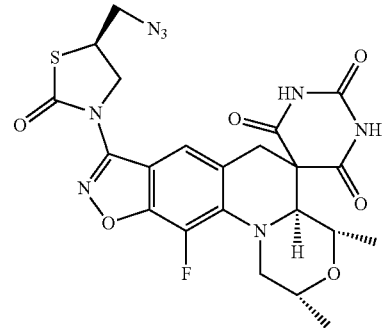

According to the synthesis method of compound 1, an intermediate I-4-10 (65 mg, 0.138 mmol) and barbituric acid (20 mg, 0.152 mmol) were used as raw materials to prepare 50 mg of white solid in a yield of 66%. $^1$H NMR (400 MHz, DMSO) δ 11.83 (s, 1H), 11.49 (s, 1H), 7.46 (s, 1H), 4.36 (dd, J=10.9, 7.5 Hz, 1H), 4.28 (dt, J=13.6, 5.1 Hz, 1H), 4.14-4.05 (m, 2H), 3.94 (d, J=8.8 Hz, 1H), 3.89-3.77 (m, 3H), 3.69-3.62 (m, 2H), 3.16-3.06 (m, 1H), 2.91 (d, J=13.9 Hz, 1H), 1.15 (d, J=6.2 Hz, 3H), 0.89 (d, J=6.4 Hz, 3H); $^{13}$C NMR (151 MHz, DMSO) δ 170.94, 170.04, 167.71, 153.61 (d, J=12.9 Hz), 153.37, 149.53, 134.82, 133.25 (d, J=239.0 Hz), 122.43, 118.32, 106.74, 72.13, 71.69, 64.33 (d, J=16.7 Hz), 56.27 (d, J=9.3 Hz), 53.72, 52.89, 51.68, 42.04, 38.50, 18.20, 18.16; MS(EI) m/z: [M+, 544].

Example 11: (2R,4S,4aS)-8-((S)-4-ethyl-2-oxothiazol-3-yl)-11-fluoro-2,4-dimethyl-1,2,4, 4a-tetrahydro-2'H,6H-spiro[isoxazole[4,5-g][1,4]oxazine[4,3-a]quinoline-5,5'-pyrimidine]-2',4',6'(1'H,3'H)-trione (Compound 11)

(b) (S)-2-((5-(1,3-dioxolan-2-yl)-6,7-difluorobenzo[d]isoxazol-3-yl)amino)butanol (I-3-11)

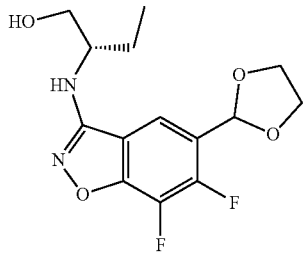 [SMILES: CC[C@@H](CO)Nc1noc2c(F)c(F)c(C3OCCO3)cc12]

According to the synthesis method of intermediate I-3-1, an intermediate A (700 mg, 2.833 mmol), N-chlorosuccinimide (454 mg, 3.400 mmol), (S)-2-amino-1-butanol (0.800 ml, 8.499 mmol) and cesium carbonate (3.692 g, 11.332 mmol) were used as raw materials to prepare 650 mg of white solid in a yield of 73%. ¹H NMR (400 MHz, CDCl₃) δ 7.50 (d, J=5.2 Hz, 1H), 6.11 (s, 1H), 4.55 (d, J=7.1 Hz, 1H), 4.21-4.07 (m, 4H), 3.92 (dd, J=12.7, 5.2 Hz, 1H), 3.82-3.72 (m, 2H), 2.18 (s, 1H), 1.80-1.71 (m, 2H), 1.04 (t, J=7.4 Hz, 3H).

(c) (S)—S-(2-((5-(1,3-dioxolan-2-yl)-6,7-difluorobenzo[d]isoxazol-3-yl)amino)butyl)acetylthio (I-4-11)

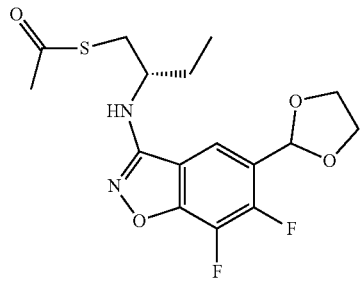 [SMILES: CC[C@@H](CSC(C)=O)Nc1noc2c(F)c(F)c(C3OCCO3)cc12]

According to the synthesis method of S-(2-((5-(1,3-dioxolan-2-yl)-6,7-difluorobenzo[d]isoxazol-3-yl)amino)ethyl)acetylthio (I-4-1), an intermediate I-3-11 (530 mg, 1.687 mmol), triphenylphosphine (1.33 g, 5.064 mmol), diisopropyl azodicarboxylate (1.000 ml, 5.064 mmol) and thioacetic acid (0.360 ml, 5.064 mmol) were used as raw materials to prepare 550 mg of light yellow solid in a yield of 88%. ¹H NMR (400 MHz, CDCl₃) δ 7.44 (d, J=5.2 Hz, 1H), 6.11 (s, 1H), 4.67 (d, J=7.7 Hz, 1H), 4.23-4.08 (m, 4H), 3.87 (dd, J=13.3, 6.7 Hz, 1H), 3.25 (d, J=5.4 Hz, 2H), 2.35 (s, 3H), 1.77 (dq, J=9.4, 7.0 Hz, 2H), 1.03 (t, J=7.4 Hz, 3H).

(d) (S)-3-(5-(1,3-dioxolan-2-yl)-6,7-difluorobenzo[d]isoxazol-3-yl)-4-ethylthiazol-2-one (I-6-11)

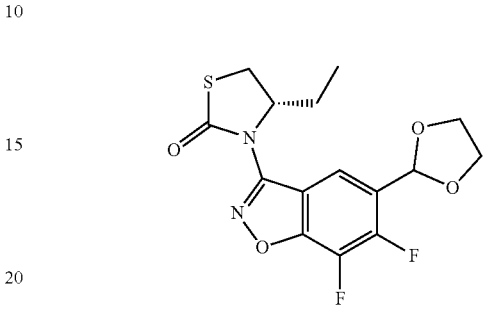

According to the synthesis method of 3-(5-(1,3-dioxolan-2-yl)-6,7-difluorobenzo[d]isoxazol-3-yl)tetrahydrothiazol-2-one (I-6-1), an intermediate I-4-11 (550 mg, 1.478 mmol), sodium hydroxide (89 mg, 2.217 mmol), dithiothreitol (228 mg, 1.478 mmol), N,N-carbonyl diimidazole (478 mg, 2.956 mmol), and 4-dimethylaminopyridine (180 mg, 1.478 mmol) were used as raw materials to prepare 256 mg of white solid in a yield of 49%. ¹H NMR (400 MHz, CDCl₃) δ 8.09 (d, J=5.6 Hz, 1H), 6.15 (s, 1H), 4.70-4.63 (m, 1H), 4.22-4.06 (m, 4H), 3.76 (dd, J=11.2, 7.6 Hz, 11H), 3.28 (dd, J=11.2, 3.7 Hz, 11H), 2.12-1.97 (m, 2H), 1.03 (t, J=7.4 Hz, 3H).

(e) (S)-3-(4-ethyl-2-oxothiazol-3-yl)-6,7-difluorobenzo[d]isoxazole-5-carbaldehyde (I-7-11)

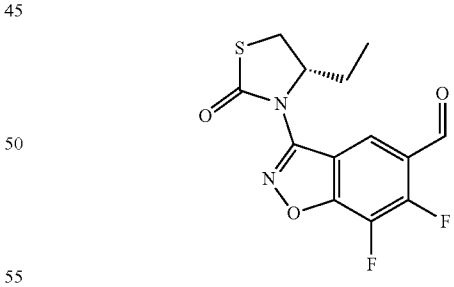

According to the synthesis method of 6,7-difluoro-3-(2-oxothiazolin-3-yl)benzo[d]isoxazole-5-carbaldehyde (I-7-1), an intermediate I-6-11 (256 mg, 0.719 mmol) and 6 M hydrochloric acid (8 ml) were used as raw materials to prepare 206 mg of white solid in a yield of 92%. ¹H NMR (400 MHz, CDCl₃) δ 10.30 (s, 1H), 8.54 (d, J=5.7 Hz, 1H), 4.71-4.63 (m, 1H), 3.78 (dd, J=11.2, 7.5 Hz, 1H), 3.31 (dd, J=11.3, 3.3 Hz, 1H), 2.17-1.96 (m, 2H), 1.05 (t, J=7.5 Hz, 3H).

(f) 6-((2R,6R)-2,6-dimethylmorpholine)-3-((S)-4-ethyl-2-oxothiazol-3-yl)-7-fluorobenzo[d]isoxazole-5-carbaldehyde (I-8-11)

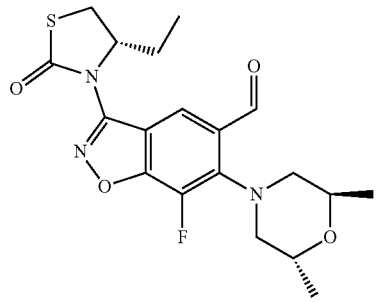 [SMILES: CC[C@H]1CSC(=O)N1c1noc2c(F)c(N3C[C@@H](C)O[C@H](C)C3)c(C=O)cc12]

According to the synthesis method of 6-((2R,6R)-2,6-dimethylmorpholine)-7-fluoro-3-(2-oxothiazolin-3-yl)benzo[d]isoxazole-5-carbaldehyde (I-8-1), an intermediate I-7-11 (220 mg, 0.705 mmol), 2R,6R-dimethylmorpholine (0.190 ml, 1.410 mmol), and N,N-diisopropyl ethylamine (0.360 ml, 2.115 mmol) were used as raw materials to prepare 230 mg of light yellow solid in a yield of 80%. $^1$H NMR (400 MHz, CDCl$_3$) δ 10.41 (s, 1H), 8.40 (s, 1H), 4.69-4.63 (m, 1H), 4.29-4.22 (m, 2H), 3.76 (dd, J=10.9, 7.5 Hz, 11H), 3.43 (d, J=11.8 Hz, 2H), 3.29 (dd, J=11.2, 3.7 Hz, 1H), 3.05 (dd, J=11.8, 5.6 Hz, 2H), 2.12-1.95 (m, 2H), 1.34 (d, J=6.4 Hz, 6H), 1.04 (t, J=7.5 Hz, 3H).

(g) (2R,4S,4aS)-8-((S)-4-ethyl-2-oxothiazol-3-yl)-11-fluoro-2,4-dimethyl-1,2,4,4a-tetrahydro-2'H,6H-spiro[isoxazole[4,5-g][1,4]oxazine[4,3-a]quinoline-5,5'-pyrimidine]-2',4',6'(1'H,3'H)-trione (Compound 11)

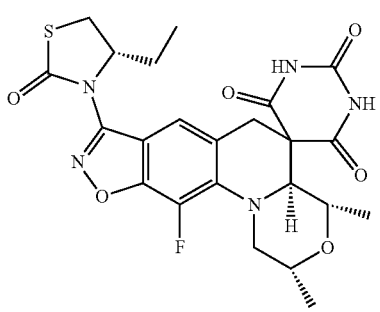

According to the synthesis method of compound 1, an intermediate I-8-11 (170 mg, 0.418 mmol) and barbituric acid (59 mg, 0.459 mmol) were used as raw materials to prepare 135 mg of white solid in a yield of 62%. $^1$H NMR (400 MHz, DMSO) δ 11.84 (s, 1H), 11.51 (s, 1H), 7.33 (s, 11H), 4.56 (ddd, J=11.6, 7.6, 3.7 Hz, 11H), 4.10 (d, J=12.6 Hz, 1H), 3.94 (d, J=8.8 Hz, 1H), 3.87-3.74 (m, 2H), 3.70-3.59 (m, 2H), 3.38 (dd, J=11.4, 3.9 Hz, 1H), 3.15-3.06 (m, 1H), 2.91 (d, J=13.9 Hz, 1H), 1.91-1.76 (m, 2H), 1.15 (d, J=6.2 Hz, 3H), 0.96-0.84 (m, 6H); $^{13}$C NMR (126 MHz, DMSO) δ 171.62, 171.39, 168.18, 153.82 (d, J=12.9 Hz), 153.43, 149.90, 135.28, 133.76 (d, J=239.5 Hz), 123.19, 117.98, 108.10, 72.59, 72.16, 64.84, 62.17, 56.79, 53.33, 38.91, 31.07, 24.51, 18.64, 18.60, 9.41; MS (ESI) m/z: [(M+H)$^+$, 518.2].

Example 12: (2R,4S,4aS)-8-((R)-4-ethyl-2-oxothiazol-3-yl)-11-fluoro-2,4-dimethyl-1,2,4, 4a-tetrahydro-2'H,6H-spiro[isoxazole[4,5-g][1,4]oxazine[4,3-a]quinoline-5,5'-pyrimidine]-2',4',6'(1'H,3'H)-trione (Compound 12)

(a) (R)-2-((5-(1,3-dioxolan-2-yl)-6,7-difluorobenzo[d]isoxazol-3-yl)amino)butanol (I-3-12)

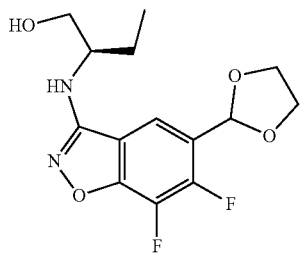 [SMILES: CC[C@H](CO)Nc1noc2c(F)c(F)c(C3OCCO3)cc12]

According to the synthesis method of intermediate I-3-1, an intermediate A (500 mg, 2.024 mmol), N-chlorosuccinimide (324 mg, 2.429 mmol), (R)-2-amino-1-butanol (0.620 ml, 6.612 mmol) and cesium carbonate (2.640 g, 8.096 mmol) were used as raw materials to prepare 514 mg of white solid in a yield of 88%. $^1$H NMR (400 MHz, CDCl$_3$) δ 7.50 (d, J=5.2 Hz, 1H), 6.11 (s, 1H), 4.55 (d, J=7.1 Hz, 1H), 4.21-4.07 (m, 4H), 3.92 (dd, J=12.7, 5.2 Hz, 1H), 3.82-3.72 (m, 2H), 2.18 (s, 1H), 1.80-1.71 (m, 2H), 1.04 (t, J=7.4 Hz, 3H).

(b) (R)—S-(2-((5-(1,3-dioxolan-2-yl)-6,7-difluorobenzo[d]isoxazol-3-yl)amino)butyl)acetyl thio (I-4-12)

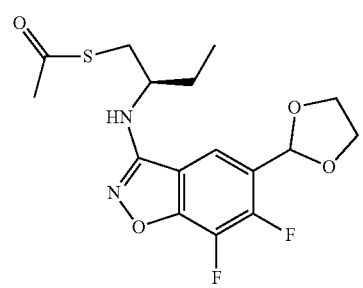 [SMILES: CC[C@H](CSC(C)=O)Nc1noc2c(F)c(F)c(C3OCCO3)cc12]

According to the synthesis method of S-(2-((5-(1,3-dioxolan-2-yl)-6,7-difluorobenzo[d]isoxazol-3-yl)amino)ethyl)acetylthio (I-4-1), an intermediate I-3-12 (491 mg, 1.563 mmol), triphenylphosphine (1.230 g, 4.680 mmol), diisopropyl azodicarboxylate (0.900 ml, 4.680 mmol) and thioacetic acid (0.330 ml, 4.680 mmol) were used as raw materials to prepare 480 mg of light yellow solid in a yield of 83%. $^1$H NMR (400 MHz, CDCl$_3$) δ 7.44 (d, J=5.2 Hz, 1H), 6.11 (s, 1H), 4.67 (d, J=7.7 Hz, 1H), 4.23-4.08 (m, 4H), 3.87 (dd, J=13.3, 6.7 Hz, 1H), 3.25 (d, J=5.4 Hz, 2H), 2.35 (s, 3H), 1.77 (dq, J=9.4, 7.0 Hz, 2H), 1.03 (t, J=7.4 Hz, 3H).

(c) (R)-3-(5-(1,3-dioxolan-2-yl)-6,7-difluorobenzo[d]isoxazol-3-yl)-4-ethylthiazol-2-one (I-6-12)

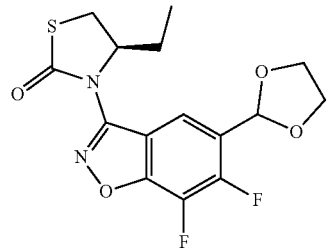 [SMILES: CC[C@@H]1CSC(=O)N1c1noc2c(F)c(F)c(C3OCCO3)cc12]

According to the synthesis method of 3-(5-(1,3-dioxolan-2-yl)-6,7-difluorobenzo[d]isoxazol-3-yl)tetrahydrothiazol-2-one (I-6-1), an intermediate I-4-12 (500 mg, 1.344 mmol), sodium hydroxide (81 mg, 2.016 mmol), dithiothreitol (208 mg, 1.344 mmol), N,N-carbonyl diimidazole (435 mg, 2.688 mmol), and 4-dimethylaminopyridine (164 mg, 1.344 mmol) were used as raw materials to prepare 300 mg of white solid in a yield of 63%. $^1$H NMR (400 MHz, CDCl$_3$) δ 8.09 (d, J=5.6 Hz, 1H), 6.15 (s, 1H), 4.70-4.63 (m, 1H), 4.22-4.06 (m, 4H), 3.76 (dd, J=11.2, 7.6 Hz, 1H), 3.28 (dd, J=11.2, 3.7 Hz, 1H), 2.12-1.97 (m, 2H), 1.03 (t, J=7.4 Hz, 3H).

(d) (R)-3-(4-ethyl-2-oxothiazol-3-yl)-6,7-difluorobenzo[d]isoxazole-5-carbaldehyde (I-7-12)

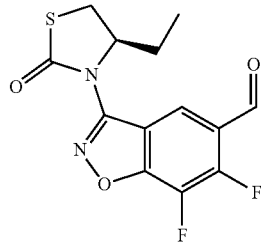 [SMILES: CC[C@@H]1CSC(=O)N1c1noc2c(F)c(F)c(C=O)cc12]

According to the synthesis method of 6,7-difluoro-3-(2-oxothiazolin-3-yl)benzo[d]isoxazole-5-carbaldehyde (I-7-1), an intermediate I-6-12 (270 mg, 0.758 mmol) and 6M hydrochloric acid (6 ml) were used as raw materials to prepare 210 mg of white solid in a yield of 89%. $^1$H NMR (400 MHz, CDCl$_3$) δ 10.30 (s, 1H), 8.54 (d, J=5.7 Hz, 1H), 4.71-4.63 (m, 1H), 3.78 (dd, J=11.2, 7.5 Hz, 1H), 3.31 (dd, J=11.3, 3.3 Hz, 1H), 2.17-1.96 (m, 2H), 1.05 (t, J=7.5 Hz, 3H).

(e) 6-((2R,6R)-2,6-dimethylmorpholine)-3-((R)-4-ethyl-2-oxothiazol-3-yl)-7-fluorobenzo[d]isoxazole-5-carbaldehyde (I-8-12)

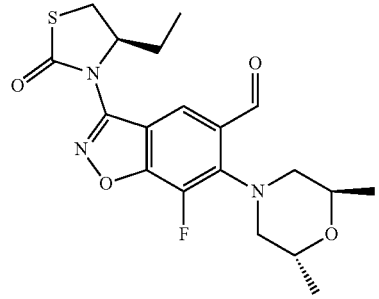 [SMILES: CC[C@@H]1CSC(=O)N1c1noc2c(F)c(N3C[C@@H](C)O[C@H](C)C3)c(C=O)cc12]

According to the synthesis method of 6-((2R,6R)-2,6-dimethylmorpholine)-7-fluoro-3-(2-oxothiazolin-3-yl)benzo[d]isoxazole-5-carbaldehyde (I-8-1), an intermediate I-7-12 (220 mg, 0.705 mmol), 2R,6R-dimethylmorpholine (0.190 ml, 1.410 mmol), N,N-diisopropylethylamine (0.360 ml, 2.115 mmol) were used as raw materials to prepare 190 mg of light yellow solid in a yield of 66%. $^1$H NMR (400 MHz, CDCl$_3$) δ 10.40 (s, 1H), 8.39 (s, 1H), 4.70-4.62 (m, 1H), 4.31-4.19 (m, 2H), 3.76 (dd, J=11.1, 7.5 Hz, 1H), 3.43 (d, J=11.9 Hz, 2H), 3.29 (dd, J=11.2, 3.5 Hz, 1H), 3.04 (dd, J=11.7, 5.6 Hz, 2H), 2.10-1.97 (m, 2H), 1.34 (d, J=6.4 Hz, 6H), 1.03 (t, J=7.4 Hz, 3H).

(f) (2R,4S,4aS)-8-((R)-4-ethyl-2-oxothiazol-3-yl)-11-fluoro-2,4-dimethyl-1,2,4,4a-tetrahydro-2'H,6H-spiro[isoxazole[4,5-g][1,4]oxazine[4,3-a]quinoline-5,5'-pyrimidine]-2',4',6'(1'H,3'H)-trione (Compound 11)

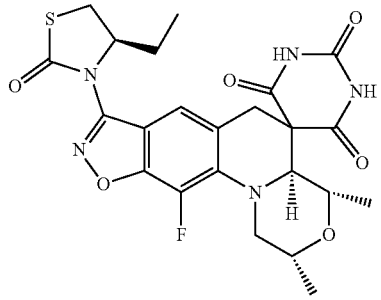

According to the synthesis method of compound 1, an intermediate I-8-12 (140 mg, 0.342 mmol) and barbituric acid (52 mg, 0.409 mmol) were used as raw materials to prepare 105 mg of white solid in a yield of 59%. $^1$H NMR (400 MHz, DMSO) δ 11.83 (s, 1H), 11.48 (s, 1H), 7.31 (s, 1H), 4.53 (ddd, J=11.2, 7.7, 3.2 Hz, 1H), 4.09 (d, J=12.6 Hz, 1H), 3.94 (d, J=8.8 Hz, 1H), 3.87-3.75 (m, 2H), 3.71-3.62 (m, 2H), 3.37 (dd, J=10.9, 2.6 Hz, 1H), 3.14-3.05 (m, 1H), 2.91 (d, J=14.0 Hz, 1H), 1.95-1.79 (m, 2H), 1.14 (d, J=6.2 Hz, 3H), 0.93 (t, J=7.5 Hz, 3H), 0.89 (d, J=6.4 Hz, 3H); $^{13}$C NMR (151 MHz, DMSO) δ 171.02, 170.93, 167.68, 153.32 (d, J=12.8 Hz), 153.03, 149.51, 134.85, 133.36 (d, J=239.4 Hz), 122.70, 117.57, 107.61, 72.13, 71.70, 64.36, 62.20, 56.29 (d, J=9.3 Hz), 52.88, 38.46, 30.71, 23.85, 18.20, 18.15, 9.11; MS(ESI) m/z: [(M−1)$^-$, 516.1].

Example 13: (2R,4S,4aS)-11-fluoro-2,4-dimethyl-8-((S)-2-oxo-5-phenylthiazol-3-yl)-1,2, 4,4a-tetrahydro-2'H,6H-spiro[isoxazole[4,5-g][1,4]oxazine[4,3-a]quinoline-5,5'-pyrimidine]-2',4',6'(1'H,3'H)-trione (Compound 13)

(a) (R)-2-((5-(1,3-dioxolan-2-yl)-6,7-difluorobenzo[d]isoxazol-3-yl)amino)-1-phenylethanol (I-3-13)

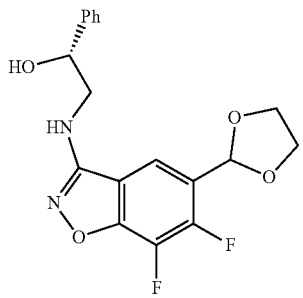 [SMILES: O[C@@H](CNc1noc2c(F)c(F)c(C3OCCO3)cc12)c1ccccc1]

According to the synthesis method of intermediate I-3-1, an intermediate A (500 mg, 2.024 mmol), N-chlorosuccinimide (324 mg, 2.429 mmol), (R)-2-amino-1-phenylethanol (833 mg, 6.072 mmol) and cesium carbonate (2.64 g, 8.096 mmol) were used as raw materials to prepare 505 mg of white solid in a yield of 69%. $^1$H NMR (400 MHz, DMSO) δ 8.04 (d, J=5.6 Hz, 1H), 7.55 (t, J=5.6 Hz, 1H), 7.41 (d, J=7.1 Hz, 2H), 7.36 (t, J=7.4 Hz, 2H), 7.27 (t, J=7.1 Hz, 1H), 6.09 (s, 1H), 5.59 (d, J=4.5 Hz, 1H), 4.95-4.88 (m, 1H), 4.12-4.01 (m, 4H), 3.44-3.33 (m, 2H).

(b) (S)—S-(2-((5-(1,3-dioxolan-2-yl)-6,7-difluorobenzo[d]isoxazol-3-yl)amino)-1-phenylethyl) acetylthio (I-4-13)

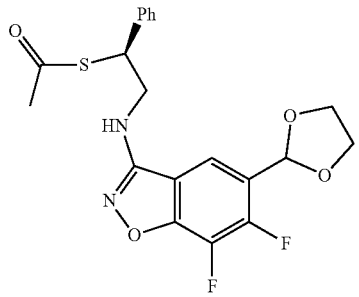 [SMILES: CC(=O)S[C@H](CNc1noc2c(F)c(F)c(C3OCCO3)cc12)c1ccccc1]

According to the synthesis method of S-(2-((5-(1,3-dioxolan-2-yl)-6,7-difluorobenzo[d]isoxazol-3-yl)amino) ethyl) acetylthio (I-4-1), an intermediate I-3-13 (382 mg, 1.055 mmol), triphenylphosphine (829 mg, 3.165 mmol), diisopropyl azodicarboxylate (0.622 ml, 3.165 mmol) and thioacetic acid (0.255 ml, 3.165 mmol) were used as raw materials to prepare 350 mg of light yellow solid in a yield of 79%. $^1$H NMR (400 MHz, CDCl$_3$) δ 7.43-7.31 (m, 6H), 6.10 (s, 1H), 5.00-4.96 (m, 1H), 4.71 (t, J=6.1 Hz, 1H), 4.21-4.07 (m, 4H), 3.97-3.91 (m, 2H), 2.38 (s, 3H).

(c) (S)-3-(5-(1,3-dioxolan-2-yl)-6,7-difluorobenzo[d]isoxazol-3-yl)-5-phenylthiazol-2-one (I-6-13)

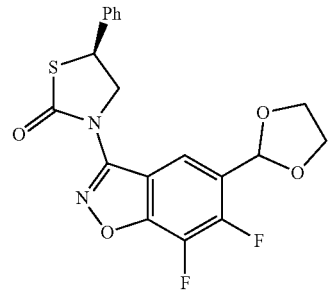 [SMILES: O=C1S[C@@H](c2ccccc2)CN1c1noc2c(F)c(F)c(C3OCCO3)cc12]

According to the synthesis method of 3-(5-(1,3-dioxolan-2-yl)-6,7-difluorobenzo[d]isoxazol-3-yl)tetrahydrothiazol-2-one (I-6-1), an intermediate I-4-13 (350 mg, 0.833 mmol), sodium hydroxide (50 mg, 1.250 mmol), dithiothreitol (64 mg, 0.416 mmol), N,N-carbonyl diimidazole (269 mg, 1.666 mmol), and 4-dimethylaminopyridine (102 mg, 0.833 mmol) were used as raw materials to prepare 167 mg of white solid in a yield of 50%. $^1$H NMR (400 MHz, CDCl$_3$) δ 8.23 (d, J=5.8 Hz, 1H), 7.52 (d, J=6.8 Hz, 2H), 7.47-7.38 (m, 3H), 6.17 (s, 1H), 5.20 (t, J=7.9 Hz, 1H), 4.61 (dd, J=11.2, 7.4 Hz, 1H), 4.43-4.36 (m, 1H), 4.24-4.09 (m, 4H).

(d) (S)-6,7-difluoro-3-(2-oxo-5-phenylthiazol-3-yl)benzo[d]isoxazole-5-carbaldehyde (I-7-13)

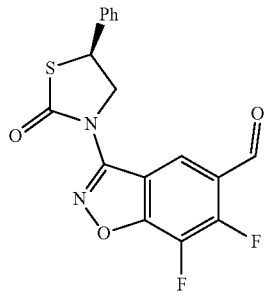 [SMILES: O=Cc1cc2c(N3C[C@H](c4ccccc4)SC3=O)noc2c(F)c1F]

According to the synthesis method of 6,7-difluoro-3-(2-oxothiazolin-3-yl)benzo[d]isoxazole-5-carbaldehyde (I-7-1), an intermediate I-6-13 (160 mg, 0.396 mmol) and 6 M hydrochloric acid (5 ml) were used as raw materials to prepare 129 mg of white solid in a yield of 90%. $^1$H NMR (400 MHz, CDCl$_3$) δ 10.33 (s, 1H), 8.67 (d, J=5.8 Hz, 1H), 7.53 (d, J 7.2 Hz, 2H), 7.48-7.41 (m, 3H), 5.22 (t, J=7.8 Hz, 1H), 4.63 (dd, J=11.1, 7.3 Hz, 1H), 4.38 (dd, J=11.1, 8.5 Hz, 1H).

(e) 6-((2R,6R)-2,6-dimethylmorpholine)-7-fluoro-3-((S)-2-oxo-5-phenylthiazol-3-yl)benzo[d]isoxazole-5-carbaldehyde (I-8-13)

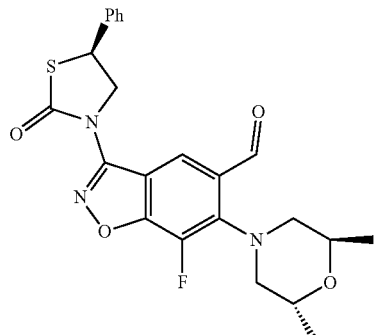

According to the synthesis method of 6-((2R,6R)-2,6-dimethylmorpholine)-7-fluoro-3-(2-oxothiazolin-3-yl)benzo[d]isoxazole-5-carbaldehyde (I-8-1), an intermediate I-7-13 (120 mg, 0.333 mmol), 2R,6R-dimethylmorpholine (0.090 ml, 0.666 mmol), and N,N-diisopropyl ethylamine (0.170 ml, 0.999 mmol) were used as raw materials to prepare 102 mg of light yellow solid in a yield of 67%. $^1$H NMR (400 MHz, CDCl$_3$) δ 10.42 (s, 1H), 8.53 (s, 1H), 7.52 (d, J=7.7 Hz, 2H), 7.47-7.40 (m, 3H), 5.20 (t, J=7.8 Hz, 1H), 4.61 (dd, J=11.1, 7.4 Hz, 1H), 4.36 (dd, J=11.2, 8.3 Hz, 1H), 4.29-4.23 (m, 2H), 3.44 (d, J=12.0 Hz, 2H), 3.06 (dd, J=11.7, 5.5 Hz, 2H), 1.34 (d, J=6.5 Hz, 6H).

(f) (2R,4S,4aS)-11-fluoro-2,4-dimethyl-8-((S)-2-oxo-5-phenylthiazol-3-yl)-1,2,4,4a-tetrahydro-2'H,6H-spiro[isoxazole[4,5-g][1,4]oxazine[4,3-a]quinoline-5,5'-pyrimidine]-2',4',6'(1'H, 3'H)-trione (Compound 13)

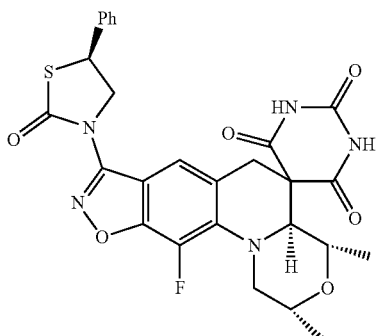

According to the synthesis method of compound 1, an intermediate I-8-13 (100 mg, 0.220 mmol) and barbituric acid (34 mg, 0.264 mmol) were used as raw materials to prepare 80 mg of white solid in a yield of 64%. $^1$H NMR (400 MHz, DMSO) δ 11.85 (s, 1H), 11.48 (s, 1H), 7.59-7.55 (m, 2H), 7.47 (s, 1H), 7.45-7.35 (m, 3H), 5.45 (t, J=7.7 Hz, 1H), 4.59 (dd, J=10.8, 7.4 Hz, 1H), 4.34 (dd, J=10.8, 8.1 Hz, 1H), 4.10 (d, J=12.6 Hz, 1H), 3.95 (d, J=8.8 Hz, 1H), 3.84-3.75 (m, 1H), 3.72-3.63 (m, 2H), 3.16-3.08 (m, 1H), 2.93 (d, J=14.0 Hz, 1H), 1.15 (d, J=6.2 Hz, 3H), 0.90 (d, J=6.4 Hz, 3H); $^{13}$C NMR (151 MHz, DMSO) δ 170.94, 170.37, 167.69, 153.59 (d, J=12.8 Hz), 153.35, 149.54, 137.93, 134.92, 133.36 (d, J=239.1 Hz), 129.03 (2), 128.53, 127.70 (2), 122.56, 118.10, 106.89, 72.12, 71.70, 64.39, 56.28 (d, J=8.9 Hz), 55.93, 52.96, 46.22, 38.52, 18.20, 18.17; MS(ESI) m/z: [(M−1)$^-$, 564.1].

Example 14: (2R,4S,4aS)-11-fluoro-2,4-dimethyl-8-((S)-2-oxo-4-phenylthiazol-3-yl)-1,2, 4,4a-tetrahydro-2'H,6H-spiro[isoxazole[4,5-g][1,4]oxazine[4,3-a]quinoline-5,5'-pyrimidine]-2',4',6'(1'H,3'H)-trione (Compound 14)

(a) (S)-2-((5-(1,3-dioxolan-2-yl)-6,7-difluorobenzo[d]isoxazol-3-yl)amino)-2-phenylethanol (I-3-14)

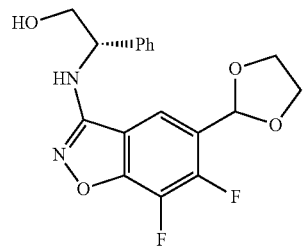 [SMILES: OC[C@@H](Nc1noc2c(F)c(F)c(C3OCCO3)cc12)c1ccccc1]

According to the synthesis method of intermediate I-3-1, an intermediate A (500 mg, 2.024 mmol), N-chlorosuccinimide (324 mg, 2.429 mmol), (R)-2-amino-phenylethanol (833 mg, 6.072 mmol) and cesium carbonate (2.64 g, 8.096 mmol) were used as raw materials to prepare 531 mg of white solid in a yield of 71%. $^1$H NMR (400 MHz, CDCl$_3$) δ 7.56 (d, J=5.1 Hz, 1H), 7.44-7.31 (m, 5H), 6.12 (s, 1H), 5.25 (d, J=6.0 Hz, 1H), 4.94 (dd, J=10.2, 5.8 Hz, 1H), 4.20-4.07 (m, 5H), 3.97 (dd, J=11.3, 5.8 Hz, 1H).

(b) (S)—S-(2-((5-(1,3-dioxolan-2-yl)-6,7-difluorobenzo[d]isoxazol-3-yl)amino)-2-phenylethyl) acetylthio (I-4-14)

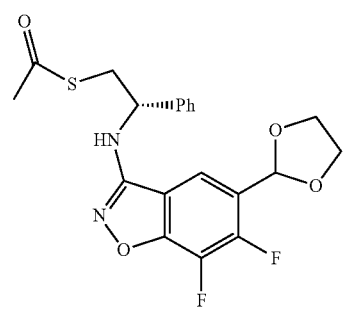 [SMILES: CC(=O)SC[C@@H](Nc1noc2c(F)c(F)c(C3OCCO3)cc12)c1ccccc1]

According to the synthesis method of S-(2-((5-(1,3-dioxolan-2-yl)-6,7-difluorobenzo[d]isoxazol-3-yl)amino)ethyl)acetylthio (I-4-1), an intermediate I-3-14 (300 mg, 0.828 mmol), triphenylphosphine (651 mg, 2.485 mmol), diisopropyl azodicarboxylate (0.490 ml, 2.485 mmol) and thioacetic acid (0.180 ml, 2.485 mmol) were used as raw materials to prepare 300 mg of light yellow solid in a yield of 86%. $^1$H NMR (400 MHz, CDCl$_3$) δ 7.46 (dd, J=12.8, 6.3 Hz, 3H), 7.38 (t, J=7.3 Hz, 2H), 7.32 (d, J=7.1 Hz, 1H), 6.12

(s, 1H), 5.51 (d, J=6.1 Hz, 1H), 4.97-4.92 (m, 1H), 4.24-4.08 (m, 4H), 3.55 (dd, J=14.5, 9.6 Hz, 1H), 3.27 (dd, J=14.4, 4.1 Hz, 1H), 2.40 (s, 3H).

(c) (S)-3-(5-(1,3-dioxolan-2-yl)-6,7-difluorobenzo[d]isoxazol-3-yl)-4-phenylthiazol-2-one (I-6-14)

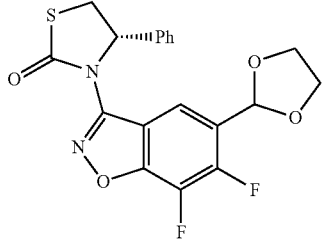 [SMILES: O=C1SC[C@H](c2ccccc2)N1c1noc2c(F)c(F)c(C3OCCO3)cc12]

According to the synthesis method of 3-(5-(1,3-dioxolan-2-yl)-6,7-difluorobenzo[d]isoxazol-3-yl)tetrahydrothiazol-2-one (I-6-1), an intermediate I-4-14 (300 mg, 0.714 mmol), sodium hydroxide (57 mg, 1.428 mmol), dithiothreitol (110 mg, 0.714 mmol), N,N-carbonyldiimidazole (231 mg, 4.428 mmol), and 4-dimethylaminopyridine (88 mg, 0.714 mmol) were used as raw materials to prepare 193 mg of white solid in a yield of 67%. $^1$H NMR (400 MHz, CDCl$_3$) δ 8.12 (d, J=5.4 Hz, 1H), 7.43-7.33 (m, 5H), 6.15 (s, 1H), 5.83-5.77 (m, 11H), 4.24-4.11 (m, 4H), 4.02 (dd, J=11.1, 8.0 Hz, 11H), 3.45 (dd, J=11.2, 5.4 Hz, 11H).

(d) (S)-6,7-difluoro-3-(2-oxo-4-phenylthiazol-3-yl)benzo[d]isoxazole-5-carbaldehyde (I-7-14

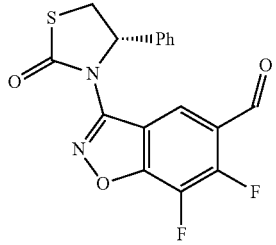 [SMILES: O=Cc1cc2c(N3C(=O)SC[C@@H]3c3ccccc3)noc2c(F)c1F]

According to the synthesis method of 6,7-difluoro-3-(2-oxothiazolin-3-yl)benzo[d]isoxazole-5-carbaldehyde (I-7-1), an intermediate I-6-14 (170 mg, 0.421 mmol) and 6M hydrochloric acid (5 ml) were used as raw materials to prepare 132 mg of white solid in a yield of 87%. $^1$H NMR (400 MHz, CDCl$_3$) δ 10.32 (s, 1H), 8.55 (d, J=5.8 Hz, 1H), 7.43-7.34 (m, 5H), 5.79 (dd, J=7.8, 5.3 Hz, 11H), 4.05 (dd, J=11.2, 8.0 Hz, 11H), 3.47 (dd, J=11.3, 5.3 Hz, 11H).

(e) 6-((2R,6R)-2,6-dimethylmorpholine)-7-fluoro-3-((S)-2-oxo-4-phenylthiazol-3-yl)benzo[d]isoxazole-5-carbaldehyde (I-8-14)

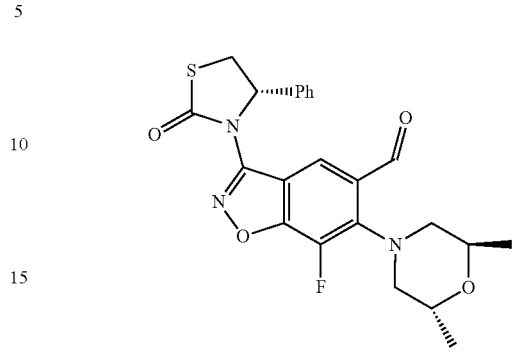

According to the synthesis method of 6-((2R,6R)-2,6-dimethylmorpholine)-7-fluoro-3-(2-oxothiazolin-3-yl)benzo[d]isoxazole-5-carbaldehyde (I-8-1), an intermediate I-7-14 (130 mg, 0.361 mmol), 2R,6R-dimethylmorpholine (0.096 ml, 0.722 mmol), and N,N-diisopropyl ethylamine (0.185 ml, 1.083 mmol) were used as raw materials to prepare 115 mg of light yellow solid in a yield of 70%. $^1$H NMR (400 MHz, CDCl$_3$) δ 10.42 (s, 1H), 8.42 (s, 1H), 7.44-7.34 (m, 5H), 5.81-5.77 (m, 1H), 4.27-4.20 (m, 2H), 4.02 (dd, J=10.5, 7.5 Hz, 1H), 3.45 (dd, J=11.1, 5.4 Hz, 1H), 3.39 (d, J=11.8 Hz, 2H), 3.02 (dd, J=11.5, 6.2 Hz, 2H), 1.32 (d, J=6.3 Hz, 6H).

(f) (2R,4S,4aS)-11-fluoro-2,4-dimethyl-8-((S)-2-oxo-4-phenylthiazol-3-yl)-1,2,4,4a-tetrahydro-2'H,6H-spiro[isoxazole[4,5-g][1,4]oxazine[4,3-a]quinoline-5,5'-pyrimidine]-2',4',6'(1'H, 3'H)-trione (Compound 14)

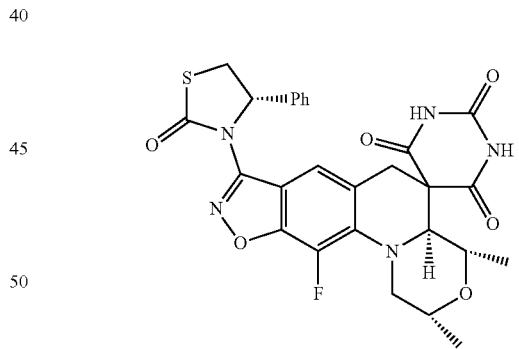

According to the synthesis method of compound 1, an intermediate I-8-14 (100 mg, 0.220 mmol) and barbituric acid (34 mg, 0.264 mmol) were used as raw materials to prepare 84 mg of white solid in a yield of 67%. $^1$H NMR (400 MHz, DMSO) δ 11.86 (s, 1H), 11.55 (s, 1H), 7.44 (s, 1H), 7.40-7.29 (m, 5H), 5.80 (dd, J=7.7, 4.3 Hz, 1H), 4.16 (dd, J=11.3, 7.7 Hz, 1H), 4.07 (d, J=12.6 Hz, 1H), 3.93 (d, J=8.8 Hz, 1H), 3.80-3.70 (m, 1H), 3.69-3.61 (m, 2H), 3.39 (dd, J=11.4, 4.4 Hz, 1H), 3.13-3.05 (m, 1H), 2.93 (d, J=14.0 Hz, 1H), 1.12 (d, J=6.2 Hz, 3H), 0.89 (d, J=6.3 Hz, 3H); $^{13}$C NMR (151 MHz, DMSO) δ 172.21, 171.37, 168.11, 153.68 (d, J=13.7 Hz), 153.25, 149.90, 139.36, 135.19, 133.61 (d, J=239.4 Hz), 129.15 (2), 128.61, 126.39, 123.12, 118.05, 107.86, 72.54, 72.10, 64.81, 63.71, 56.68 (d, J=8.7 Hz), 53.28, 38.90, 35.94, 18.59, 18.53; MS(ESI) m/z: [(M−1)⁻, 564.1].

Example 15: (2R,4S,4aS)-8-((S)-4-benzyl-2-oxothiazol-3-yl)-11-fluoro-2,4-dimethyl-1,2, 4,4a-tetrahydro-2'H,6H-spiro[isoxazole[4,5-g][1,4]oxazine[4,3-a]quinoline-5,5'-pyrimidine]-2',4',6'(1'H,3'H)-trione (Compound 15)

(a) (S)-2-((5-(1,3-dioxolan-2-yl)-6,7-difluorobenzo[d]isoxazol-3-yl)amino)-3-phenylpropanol (I-3-15)

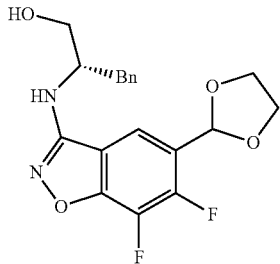 [SMILES: OC[C@H](Cc1ccccc1)Nc1noc2c(F)c(F)c(C3OCCO3)cc12]

According to the synthesis method of intermediate I-3-1, an intermediate A (500 mg, 2.024 mmol), N-chlorosuccinimide (324 mg, 2.429 mmol), L-phenylalaninol (765 mg, 5.060 mmol) and cesium carbonate (2.64 g, 8.096 mmol) were used as raw materials to prepare 544 mg of white solid in a yield of 71%. ¹H NMR (400 MHz, CDCl₃) δ 7.44 (d, J=5.2 Hz, 1H), 7.36-7.24 (m, 5H), 6.11 (s, 1H), 4.67 (d, J=7.7 Hz, 1H), 4.21-4.06 (m, 5H), 3.90 (dd, J=11.1, 3.6 Hz, 1H), 3.74 (dd, J=11.1, 4.6 Hz, 1H), 3.16 (dd, J=13.7, 6.0 Hz, 1H), 3.02 (dd, J=13.8, 7.7 Hz, 1H).

(b) (S)—S-(2-((5-(1,3-dioxolan-2-yl)-6,7-difluorobenzo[d]isoxazol-3-yl)amino)-3-phenylpropyl)acetylthio (I-4-15)

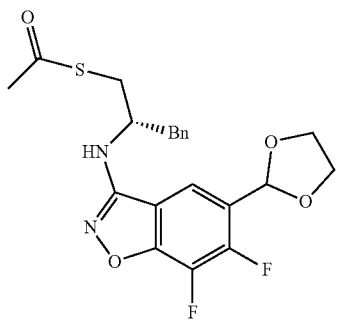 [SMILES: CC(=O)SC[C@H](Cc1ccccc1)Nc1noc2c(F)c(F)c(C3OCCO3)cc12]

According to the synthesis method of S-(2-((5-(1,3-dioxolan-2-yl)-6,7-difluorobenzo[d]isoxazol-3-yl)amino)ethyl)acetylthio (I-4-1), an intermediate I-3-15 (520 mg, 1.383 mmol), triphenylphosphine (906 mg, 3.456 mmol), diisopropyl azodicarboxylate (0.680 ml, 3.456 mmol) and thioacetic acid (0.300 ml, 4.149 mmol) were used as raw materials to prepare 500 mg of light yellow solid in a yield of 83%. ¹H NMR (400 MHz, CDCl₃) δ 7.39 (d, J=5.3 Hz, 1H), 7.36-7.30 (m, 2H), 7.27 (t, J=6.1 Hz, 3H), 6.11 (s, 1H), 4.92 (d, J=7.1 Hz, 1H), 4.22-4.10 (m, 5H), 3.28 (dd, J=13.9, 5.4 Hz, 1H), 3.19 (d, J=6.0 Hz, 2H), 2.93 (dd, J=13.9, 7.5 Hz, 1H), 2.37 (s, 3H).

(c) (S)-3-(5-(1,3-dioxolan-2-yl)-6,7-difluorobenzo[d]isoxazol-3-yl)-4-benzylthiazol-2-one (I-6-15)

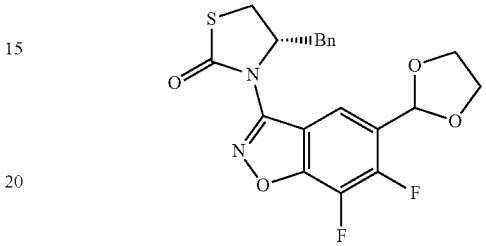

According to the synthesis method of 3-(5-(1,3-dioxolan-2-yl)-6,7-difluorobenzo[d]isoxazol-3-yl)tetrahydrothiazol-2-one (I-6-1), an intermediate I-4-15 (500 mg, 1.152 mmol), sodium hydroxide (92 mg, 2.304 mmol), dithiothreitol (89 mg, 0.575 mmol), N,N-carbonyldiimidazole (373 mg, 2.304 mmol), and 4-dimethylaminopyridine (141 mg, 1.152 mmol) were used as raw materials to prepare 450 mg of white solid in a yield of 93%. ¹H NMR (400 MHz, CDCl₃) δ 8.18 (d, J=5.9 Hz, 1H), 7.40-7.30 (m, 5H), 6.16 (s, 1H), 4.92 (t, J=8.2 Hz, 1H), 4.23-4.08 (m, 4H), 3.64-3.55 (m, 2H), 3.23 (d, J=11.2 Hz, 1H), 3.14-3.07 (m, 1H).

(d) (S)-3-(4-benzyl-2-oxothiazol-3-yl)-6,7-difluorobenzo[d]isoxazole-5-carbaldehyde (I-7-15)

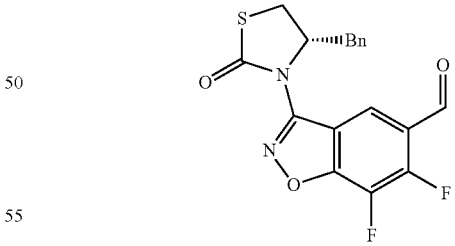

According to the synthesis method of 6,7-difluoro-3-(2-oxothiazolin-3-yl)benzo[d]isoxazole-5-carbaldehyde (I-7-1), an intermediate I-6-15 (300 mg, 0.718 mmol) and 6 M hydrochloric acid (8 ml) were used as raw materials to prepare 250 mg of white solid in a yield of 93%. ¹H NMR (400 MHz, CDCl₃) δ 10.31 (s, 1H), 8.63 (d, J=5.8 Hz, 1H), 7.40-7.30 (m, 5H), 4.95-4.90 (m, 1H), 3.65-3.55 (m, 2H), 3.25 (d, J=11.4 Hz, 1H), 3.11 (dd, J=13.3, 10.3 Hz, 1H).

(e) 3-((S)-4-benzyl-2-oxothiazol-3-yl)-6-((2R,6R)-2,6-dimethylmorpholine)-7-fluorobenzo[d]isoxazole-5-carbaldehyde (I-8-15)

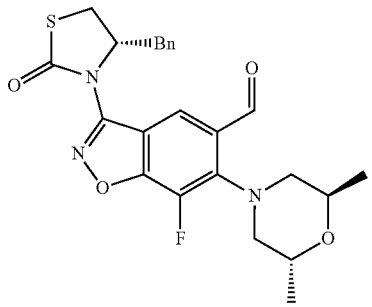 [SMILES: C[C@@H]1CN(c2c(C=O)cc3c(N4C(=O)SC[C@@H]4Cc4ccccc4)noc3c2F)C[C@@H](C)O1]

According to the synthesis method of 6-((2R,6R)-2,6-dimethylmorpholine)-7-fluoro-3-(2-oxothiazolin-3-yl)benzo[d]isoxazole-5-carbaldehyde (I-8-1), an intermediate I-7-15 (200 mg, 0.535 mmol), 2R,6R-dimethylmorpholine (0.178 ml, 1.337 mmol), and N,N-diisopropyl ethylamine (0.285 ml, 1.605 mmol) were used as raw materials to prepare 177 mg of light yellow solid in a yield of 71%. $^1$H NMR (400 MHz, CDCl$_3$) δ 10.41 (s, 1H), 8.50 (s, 1H), 7.40-7.30 (m, 5H), 4.91 (t, J=8.8 Hz, 1H), 4.26 (s, 2H), 3.64-3.54 (m, 2H), 3.45 (d, J=11.5 Hz, 2H), 3.23 (d, J=11.5 Hz, 1H), 3.13-3.03 (m, 3H), 1.35 (d, J=6.4 Hz, 6H).

(f) (2R,4S,4aS)-8-((S)-4-benzyl-2-oxothiazol-3-yl)-11-fluoro-2,4-dimethyl-1,2,4,4a-tetrahydro-2'H,6H-spiro[isoxazole[4,5-g][1,4]oxazine[4,3-a]quinoline-5,5'-pyrimidine]-2',4',6'(1'H, 3'H)-trione (Compound 15)

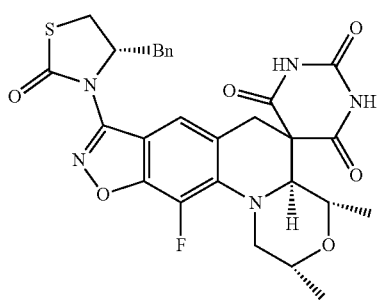

According to the synthesis method of compound 1, an intermediate I-8-15 (166 mg, 0.354 mmol) and barbituric acid (54 mg, 0.425 mmol) were used as raw materials to prepare 121 mg of white solid in a yield of 59%. $^1$H NMR (400 MHz, DMSO) δ 11.85 (s, 1H), 11.54 (s, 1H), 7.39 (s, 1H), 7.35-7.30 (m, 2H), 7.29-7.23 (m, 3H), 4.89-4.81 (m, 1H), 4.11 (d, J=12.5 Hz, 1H), 3.95 (d, J=8.8 Hz, 1H), 3.84-3.77 (m, 1H), 3.75-3.62 (m, 3H), 3.29-3.22 (m, 2H), 3.14-3.03 (m, 2H), 2.91 (d, J=14.0 Hz, 1H), 1.15 (d, J=6.2 Hz, 3H), 0.91 (d, J=6.3 Hz, 3H); $^{13}$C NMR (151 MHz, DMSO) δ 171.36 (2), 168.12, 153.89 (dd, J=13.0, 5.0 Hz), 153.39, 149.93, 136.72, 135.19, 133.69 (d, J=239.3 Hz), 129.84 (2), 129.05 (2), 127.32, 122.97, 118.38, 107.83, 72.56, 72.11, 64.82, 62.04, 56.71 (d, J=9.2 Hz), 53.31, 38.94, 36.95, 31.04, 18.60, 18.56; MS(ESI) m/z: [(M−1)$^-$, 578.1].

Example 16: (2R,4S,4aS)-8-((R)-5-ethyl-2-oxothiazol-3-yl)-11-fluoro-2,4-dimethyl-1,2,4,4a-tetrahydro-2'H,6H-spiro[isoxazole[4,5-g][1,4]oxazine[4,3-a]quinoline-5,5'-pyrimidine]-2',4',6'(1'H,3'H)-trione (Compound 16)

(a) (S)-1-((5-(1,3-dioxolan-2-yl)-6,7-difluorobenzo[d]isoxazol-3-yl)amino)sec-butanol (I-3-16)

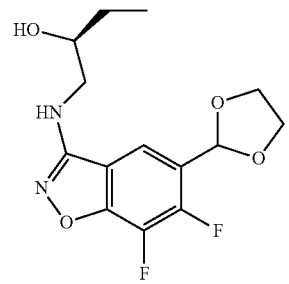 [SMILES: CC[C@H](O)CNc1noc2c(F)c(F)c(C3OCCO3)cc12]

According to the synthesis method of intermediate I-3-1, an intermediate A (600 mg, 2.429 mmol), N-chlorosuccinimide (389 mg, 2.914 mmol), (S)-1-amino-2-butanol (476 mg, 5.344 mmol) and cesium carbonate (3.957 g, 12.145 mmol) were used as raw materials to prepare 403 mg of white solid in a yield of 53%. $^1$H NMR (400 MHz, CDCl$_3$) δ 7.49 (dd, J=5.4, 1.3 Hz, 1H), 6.11 (s, 1H), 4.84 (s, 1H), 4.20-4.08 (m, 4H), 3.95-3.87 (m, 1H), 3.61 (ddd, J=13.4, 7.0, 3.1 Hz, 1H), 3.29 (ddd, J=13.2, 8.3, 4.6 Hz, 1H), 1.65-1.56 (m, 2H), 1.04 (t, J=7.5 Hz, 3H).

(b) (R)—S-(1-((5-(1,3-dioxolan-2-yl)-6,7-difluorobenzo[d]isoxazol-3-yl)amino)2-butyl)acetylthio (I-4-16)

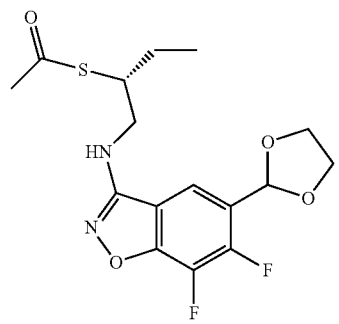 [SMILES: CC[C@H](CNc1noc2c(F)c(F)c(C3OCCO3)cc12)SC(C)=O]

According to the synthesis method of intermediate I-4-1, an intermediate I-3-16 (385 mg, 1.226 mmol), triphenylphosphine (964 mg, 3.677 mmol), diisopropyl azodicarboxylate (0.722 ml, 3.677 mmol) and thioacetic acid (0.262 ml, 3.677 mmol) were used as raw materials to prepare 400 mg of white solid in a yield of 88%. $^1$H NMR (400 MHz, CDCl$_3$) δ 7.44 (d, J=5.2 Hz, 1H), 6.11 (s, 1H), 4.86 (t, J=5.4 Hz, 1H), 4.21-4.11 (m, 4H), 3.78-3.69 (m, 2H), 3.59-3.51 (m, 1H), 2.40 (s, 3H), 1.88-1.80 (m, 1H), 1.75-1.66 (m, 1H), 1.07 (t, J=7.4 Hz, 3H).

(c) (R)-3-(5-(dioxolan-2-yl)-6,7-difluorobenzo[d]isoxazol-3-yl)-5-ethylthiazol-2-one (I-6-16)

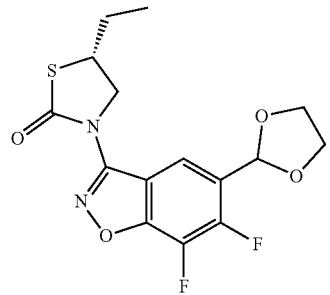 [SMILES: CC[C@@H]1CN(c2noc3c(F)c(F)c(C4OCCO4)cc23)C(=O)S1]

According to the synthesis method of intermediate I-6-1, an intermediate I-4-16 (400 mg, 1.075 mmol), sodium hydroxide (86 mg, 2.150 mmol), dithiothreitol (166 mg, 1.075 mmol), N,N-carbonyldiimidazole (349 mg, 2.150 mmol), and 4-dimethylaminopyridine (131 mg, 1.075 mmol) were used as raw materials to prepare 214 mg of white solid in a yield of 56%. $^1$H NMR (400 MHz, CDCl$_3$) δ 8.20 (d, J=5.7 Hz, 1H), 6.15 (s, 1H), 4.41 (dd, J=10.8, 7.1 Hz, 1H), 4.23-4.08 (m, 4H), 4.04 (dd, J=10.9, 6.5 Hz, 1H), 3.97-3.89 (m, 1H), 2.02-1.88 (m, 2H), 1.12 (t, J=7.4 Hz, 3H).

(d) (R)-3-(5-ethyl-2-oxothiazol-3-yl)-6,7-difluorobenzo[d]isoxazole-5-carbaldehyde (I-7-16)

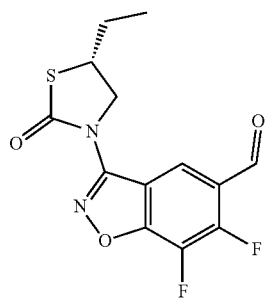 [SMILES: CC[C@@H]1CN(c2noc3c(F)c(F)c(C=O)cc23)C(=O)S1]

According to the synthesis method of intermediate I-7-1, an intermediate I-6-16 (200 mg, 0.562 mmol) and 6M hydrochloric acid (5 ml) were used as raw materials to prepare 170 mg of white solid in a yield of 97%. $^1$H NMR (400 MHz, CDCl$_3$) δ 10.30 (s, 1H), 8.64 (dd, J=5.8, 1.8 Hz, 1H), 4.41 (dd, J=10.9, 7.0 Hz, 1H), 4.04 (dd, J=10.9, 6.5 Hz, 1H), 4.00-3.92 (m, 1H), 2.02-1.91 (m, 2H), 1.13 (t, J=7.4 Hz, 3H).

(e) 6-((2R,6R)-2,6-dimethylmorpholine)-3-((R)-5-ethyl-2-oxothiazol-3-yl)-7-fluorobenzo[d]isoxazole-5-carbaldehyde (I-8-16)

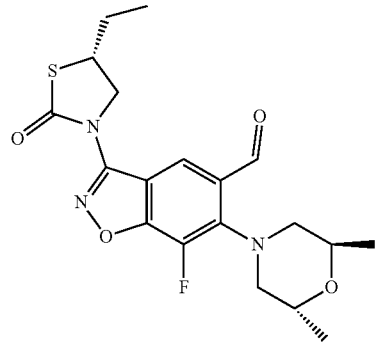 [SMILES: CC[C@@H]1CN(c2noc3c(F)c(N4C[C@@H](C)O[C@H](C)C4)c(C=O)cc23)C(=O)S1]

According to the synthesis method of intermediate I-8-1, an intermediate I-7-16 (170 mg, 0.545 mmol), 2R,6R-dimethylmorpholine (0.182 ml, 1.362 mmol), N,N-diisopropylethylamine (0.280 ml, 1.635 mmol) were used as raw materials to prepare 154 mg of yellowish white solid in a yield of 69%. $^1$H NMR (400 MHz, CDCl$_3$) δ 10.40 (s, 1H), 8.50 (d, J=1.1 Hz, 1H), 4.40 (dd, J=10.9, 7.0 Hz, 1H), 4.29-4.21 (m, 2H), 4.02 (dd, J=10.9, 6.5 Hz, 1H), 3.98-3.90 (m, 1H), 3.43 (d, J=11.9 Hz, 2H), 3.05 (dd, J=11.9, 4.7 Hz, 2H), 2.00-1.88 (m, 2H), 1.34 (d, J=6.5 Hz, 6H), 1.12 (t, J=7.4 Hz, 3H).

(f) (2R,4S,4aS)-8-((R)-5-ethyl-2-oxothiazol-3-yl)-11-fluoro-2,4-dimethyl-1,2,4,4a-tetrahydro-2'H,6H-spiro[isoxazole[4,5-g][1,4]oxazine[4,3-a]quinoline-5,5'-pyrimidine]-2',4',6'(1'H,3'H)-trione (Compound 16)

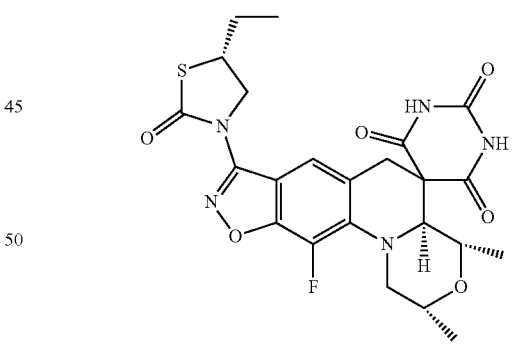

According to the synthesis method of compound 1, an intermediate I-8-16 (150 mg, 0.368 mmol) and barbituric acid (57 mg, 0.442 mmol) were used as raw materials to prepare 130 mg of white solid in a yield of 68%. $^1$H NMR (400 MHz, DMSO) δ 11.73 (s, 2H), 7.41 (s, 1H), 4.35 (dd, J=10.4, 6.7 Hz, 1H), 4.08 (d, J=12.7 Hz, 1H), 4.04-3.99 (m, 1H), 3.98-3.90 (m, 2H), 3.86-3.73 (m, 1H), 3.70-3.61 (m, 2H), 3.15-3.00 (m, 1H), 2.89 (d, J=14.3 Hz, 1H), 1.89-1.84 (m, 1H), 1.82-1.71 (m, 1H), 1.13 (d, J=6.2 Hz, 3H), 0.97 (t, J=7.3 Hz, 3H), 0.88 (d, J=6.3 Hz, 3H); $^{13}$C NMR (126 MHz, DMSO) δ 171.39, 171.21, 168.15, 154.05, 153.95, 149.94, 135.25, 133.75 (d, J=239.0 Hz), 122.81, 118.59, 107.33, 72.60, 72.13, 64.82, 56.75 (d, J=9.2 Hz), 54.64, 53.31, 45.30, 38.98, 28.49, 18.64, 18.60, 11.82; MS (ESI) m/z: [(M−1)⁻, 516.1].

Example 17: N—(((S)-3-((2R,4S,4aS)-11-fluoro-2,4-dimethyl-2',4',6'-trioxo-1,1',2,3',4,4a, 4',6'-octahydro-2'H,6H-spiro[isoxazole[4,5-g][1,4]oxazine[4,3-a]quinoline-5,5'-pyrimidine]-8-yl)-2-oxothiazol-5-yl)methyl)acetamide (Compound 17)

(a) (2R,4S,4aS)-8-((S)-5-(aminomethyl)-2-oxothiazol-3-yl)-11-fluoro-2,4-dimethyl-1,2,4, 4a-tetrahydro-2'H,6H-spiro[isoxazole[4,5-g][1,4]oxazine[4,3-a]quinoline-5,5'-pyrimidine]-2',4',6'(1'H,3'¹H)-trione (I-3-17)

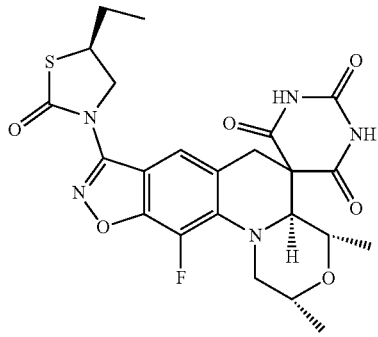

(2R,4S,4aS)-8-((R)-5-(azidomethyl)-2-oxothiazol-3-yl)-11-fluoro-2,4-dimethyl-1,2,4,4a-tetrahydro-2'H,6H-spiro[isoxazole[4,5-g][1,4]oxazine[4,3-a]quinoline-5,5'-pyrimidine]-2',4',6'(1'H,3'H)-trione (Compound 10) (50 mg, 0.092) was added into a mixed solvent of 5 ml of tetrahydrofuran and 1 ml of water at room temperature. Triphenylphosphine (29 mg, 0.110 mmol) was added and the mixture was stirred at room temperature for 12 h. After the completion of reaction was monitored by TLC, water was added and the mixture was extracted with ethyl acetate. The combined organic layers were washed with water and saturated brine, dried over anhydrous sodium sulfate, concentrated under reduced pressure and purified by column chromatography [dichloromethane:methanol=10:1] to obtain 35 mg of white solid in a yield of 74%. ¹H NMR (400 MHz, DMSO) δ 7.43 (s, 1H), 4.29 (dd, J=10.4, 7.0 Hz, 1H), 4.15-4.02 (m, 3H), 3.94 (d, J=8.8 Hz, 1H), 3.83-3.74 (s, 1H), 3.71-3.59 (m, 2H), 3.15-3.07 (m, 1H), 3.01 (dd, J=13.0, 6.3 Hz, 1H), 2.95-2.84 (m, 2H), 1.14 (d, J=6.2 Hz, 3H), 0.89 (d, J=6.4 Hz, 3H).

(b) N—(((S)-3-((2R,4S,4aS)-11-fluoro-2,4-dimethyl-2',4',6'-trioxo-1,1',2,3',4,4a,4',6'-octahydro-2'H,6H-spiro[isoxazole[4,5-g][1,4]oxazine[4,3-a]quinoline-5,5'-pyrimidine]-8-yl)-2-oxothiazol-5-yl)methyl)acetamide (Compound 17)

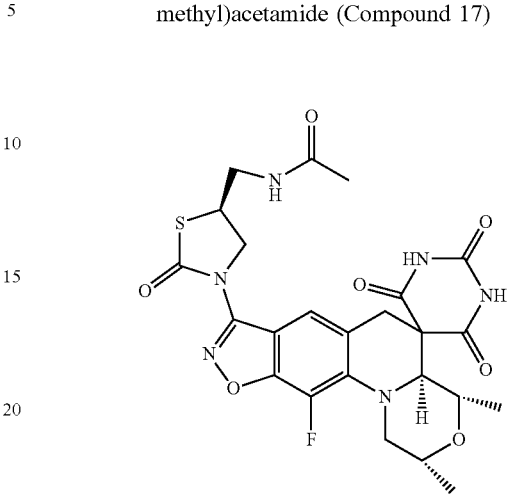

An intermediate I-3-17 (35 mg, 0.067 mmol) was added into 5 ml of tetrahydrofuran at room temperature and stirred to dissolve. N,N-diisopropylethylamine (0.018 ml, 0.101 mmol) and acetic anhydride (0.007 ml, 0.074 mmol) were added successively. After 1 h, TLC detection showed that the reaction was completed. Water was added and the mixture was extracted with ethyl acetate. The combined organic layers were washed with water and saturated brine, dried over anhydrous sodium sulfate, concentrated under reduced pressure and purified by column chromatography [dichloromethane:methanol=10:1] to obtain 30 mg of yellow solid in a yield of 80%. ¹H NMR (400 MHz, DMSO) δ 11.82 (s, 1H), 11.50 (s, 1H), 8.30 (t, J=5.8 Hz, 1H), 7.43 (s, 1H), 4.30 (dd, J=10.7, 7.1 Hz, 1H), 4.16-4.03 (m, 3H), 3.94 (d, J=8.8 Hz, 1H), 3.83-3.75 (m, 1H), 3.71-3.59 (m, 2H), 3.44 (t, J=6.5 Hz, 2H), 3.15-3.05 (m, 1H), 2.91 (d, J=14.2 Hz, 1H), 1.82 (s, 3H), 1.15 (d, J=6.2 Hz, 3H), 0.89 (d, J=6.4 Hz, 3H); ¹³C NMR (151 MHz, DMSO) δ 171.40, 171.00, 170.34, 168.16, 153.99 (d, J=13.0 Hz), 153.92, 149.98, 135.24, 133.72 (d, J=239.1 Hz), 122.86, 118.70, 107.32, 72.59, 72.14, 64.84, 56.73 (d, J=8.9 Hz), 53.34, 52.57, 43.06, 42.42, 38.97, 22.94, 18.65, 18.62; MS(EI) m/z: [M⁺, 560].

Example 18: (2R,4S,4aS)-2,4-dimethyl-8-((S)-5-methyl-2-oxothiazol-3-yl)-2',4',6'-trioxo-1,1',2,3',4, 4a,4',6'-octahydro-2'H,6H-spiro[isoxazole[4,5-g][1, 4]oxazine[4,3-a]quinoline-5,5'-pyrimidine]-11-nitrile (Compound 18)

(a) 2,6-difluoro-3-cyanobenzaldehyde (I-1-18)

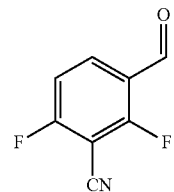 [SMILES: N#Cc1c(F)ccc(C=O)c1F]

A 2M solution of lithium diisopropylamino in tetrahydrofuran (14 ml, 28.04 mmol) was added into 20 ml of dry tetrahydrofuran at room temperature. Under the protection of argon, the mixture was cooled to −80° C. A solution of 2,6-difluorobenzonitrile (3.00 g, 21.57 mmol) in tetrahydrofuran was slowly added. After 5 min, N,N-dimethylformamide (5.00 ml, 64.71 mmol) was slowly added. After 5 min, TLC detection showed that the reaction was completed. The reaction was quenched with saturated ammonium chloride and the mixture was warmed to room temperature. Water was added and the mixture was extracted with ethyl acetate. The combined organic layers were washed with water and saturated brine, dried over anhydrous sodium sulfate, concentrated under reduced pressure and purified by column chromatography [petroleum ether:ethyl acetate=2:1] to obtain 1.72 g of colorless oil in a yield of 48%. $^1$H NMR (400 MHz, CDCl$_3$) δ 10.32 (d, J=0.6 Hz, 1H), 8.20 (ddd, J=8.9, 7.8, 6.2 Hz, 1H), 7.27-7.22 (m, 1H).

(b) 3-(1,3-dioxolan-2-yl)-2,6-difluorobenzonitrile (I-2-18)

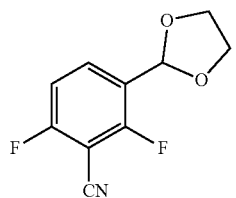 [SMILES: N#Cc1c(F)ccc(C2OCCO2)c1F]

An intermediate I-1-18 (2.00 g, 11.97 mmol) was added into 15 ml of toluene at room temperature and stirred to dissolve. Ethylene glycol (2.00 ml, 35.92 mmol) and p-toluenesulfonic acid monohydrate (227 mg, 1.197 mmol) were added. A water separator was equipped and the temperature was raised to 110° C. The mixture was reacted for 3 hours. After the completion of reaction was monitored by TLC, the mixture was cooled to room temperature, water was added and the mixture was extracted with ethyl acetate. The combined organic layers were washed with water and saturated brine, dried over anhydrous sodium sulfate, concentrated under reduced pressure and purified by column chromatography [petroleum ether:ethyl acetate=4:1] to obtain 1.92 g of colorless oil in a yield of 76%. $^1$H NMR (400 MHz, CDCl$_3$) δ 7.85-7.79 (m, 1H), 7.12-7.06 (m, 1H), 6.04 (s, 1H), 4.18-4.07 (m, 4H).

(c) 3-(1,3-dioxolan-2-yl)-2,6-difluoro-5-formylbenzonitrile (I-3-18)

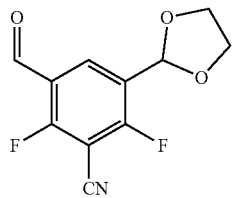 [SMILES: N#Cc1c(F)c(C=O)cc(C2OCCO2)c1F]

2 M solution of lithium diisopropylamino in tetrahydrofuran (7.7 ml, 15.41 mmol) was added into 15 ml of dry tetrahydrofuran at room temperature. Under the protection of argon, the temperature was lowered to −80° C., and a solution of intermediate I-2-18 (2.71 g, 12.84 mmol) in tetrahydrofuran was slowly added dropwise. After 30 min, N,N-dimethylformamide (2.97 ml, 38.52 mmol) was slowly added dropwise. After 30 min, TLC detection showed that the reaction was completed. The reaction was quenched with saturated ammonium chloride, and the mixture was warmed to room temperature. Water was added and the mixture was extracted with ethyl acetate. The combined organic layers were washed with water and saturated brine, dried over anhydrous sodium sulfate, concentrated under reduced pressure and purified by column chromatography [petroleum ether:ethyl acetate=5:1] to obtain 1.95 g of colorless oil in a yield of 64%. $^1$H NMR (400 MHz, CDCl$_3$) δ 10.31 (s, 1H), 8.36 (t, J=7.7 Hz, 1H), 6.07 (s, 1H), 4.21-4.06 (m, 4H).

(d) 3-(1,3-dioxolan-2-yl)-2,6-difluoro-5-((oxima)methyl)benzonitrile (I-4-18)

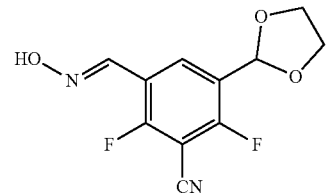 [SMILES: N#Cc1c(F)c(/C=N/O)cc(C2OCCO2)c1F]

In an ice bath, an intermediate I-3-18 (700 mg, 2.929 mmol) was added into 20 ml methanol and stirred to dissolve. Hydroxylamine hydrochloride (224 mg, 3.222 mmol) and pyridine (0.31 ml, 3.808 mmol) were added successively. The mixture was warmed to room temperature and stirred for 1 h, and then TLC detection showed that the reaction was completed. Water was added and the mixture was extracted with ethyl acetate. The combined organic layers were washed with water and saturated brine, dried over anhydrous sodium sulfate, concentrated under reduced pressure and purified by column chromatography [petroleum ether:ethyl acetate=2:1] to obtain 720 mg of white solid in a yield of 96%. $^1$H NMR (400 MHz, CDCl$_3$) δ 8.28 (s, 1H), 8.23 (t, J=7.8 Hz, 1H), 7.79 (s, 1H), 6.02 (s, 1H), 4.17-4.05 (m, 4H).

(e) (R)-3-cyano-5-(1,3-dioxolan-2-yl)-2,4-difluoro-N'-hydroxy-N-(2-hydroxypropyl)benz amidine (I-9-18)

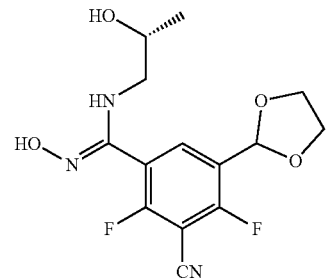 [SMILES: C[C@@H](O)CN/C(=N\O)c1cc(C2OCCO2)c(F)c(C#N)c1F]

An intermediate I-4-18 (800 mg, 3.149 mmol) was added into 20 ml of N,N-dimethylformamide at room temperature and stirred to dissolve. N-chlorosuccinimide (463 mg, 3.464 mmol) was added, and the mixture was warmed to 40° C. and reacted for 30 min. TLC detection showed that the reaction was completed. The reaction solution was cooled to 0° C., then (R)-(−)-1-amino-2-propanol (0.545 ml, 6.928 mmol) was slowly added dropwise. After 10 min, TLC detection showed that the reaction was completed. Water was added and the mixture was extracted with ethyl acetate. The combined organic layers were washed with water and saturated brine, dried over anhydrous sodium sulfate, concentrated under reduced pressure and purified by column chromatography [petroleum ether:ethyl acetate=1:3] to obtain 456 mg of light yellow powder in a yield of 44%. $^1$H NMR (400 MHz, CDCl$_3$) δ 7.89 (t, J=7.7 Hz, 1H), 6.05 (s, 1H), 5.77 (s, 1H), 4.18-4.05 (m, 4H), 3.82-3.75 (m, 1H), 2.97 (d, J=13.1 Hz, 1H), 2.87-2.80 (m, 1H), 1.11 (d, J=6.3 Hz, 3H).

(f) (R)-6-fluoro-5-formyl-3-((2-hydroxypropyl)amino)benzo[d]isoxazole-7-nitrile (I-11-18)

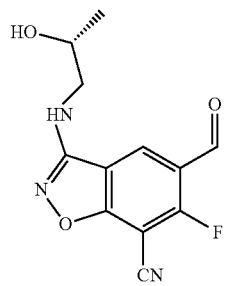 [SMILES: C[C@@H](O)CNc1noc2c(C#N)c(F)c(C=O)cc12]

An intermediate I-9-18 (443 mg, 1.354 mmol) was added into 30 ml of 1,4-dioxane at room temperature, and 6 M hydrochloric acid (8 ml) was added. The mixture was warmed to 35° C. and stirred for 2 h. After the completion of reaction was monitored by TLC, the reaction liquid was cooled to 0° C. and the saturated sodium bicarbonate aqueous solution was added to adjust the pH to 9. The mixture was stirred for 30 min and TLC detection showed that the reaction was completed. Water was added and the mixture was extracted with ethyl acetate. The combined organic layers were washed with water and saturated brine, dried over anhydrous sodium sulfate, concentrated under reduced pressure and purified by column chromatography [petroleum ether:ethyl acetate=1:3] to obtain 150 mg of pale yellow powder in a yield of 42%. $^1$H NMR (400 MHz, DMSO) δ 10.17 (s, 1H), 8.90 (d, J=6.7 Hz, 1H), 7.71 (t, J=5.7 Hz, 1H), 4.86 (d, J=4.8 Hz, 1H), 3.97-3.87 (m, 1H), 3.17 (td, J=6.0, 2.2 Hz, 2H), 1.13 (d, J=6.2 Hz, 3H).

(g) 6-((2R,6R)-2,6-dimethylmorpholine)-5-formyl-3-(((R)-2-hydroxypropyl)amino)benzo[d]isoxazole-7-nitrile (I-12-18)

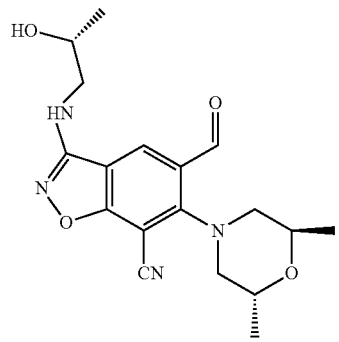 [SMILES: C[C@@H]1CN(c2c(C=O)cc3c(NC[C@@H](C)O)noc3c2C#N)C[C@@H](C)O1]

An intermediate I-11-18 (150 mg, 0.570 mmol) was added into 20 ml of acetonitrile at room temperature. 2R,6R-dimethylmorpholine (0.090 ml, 0.684 mmol) and N,N-diisopropylethylamine (0.200 ml, 1.140 mmol) were added. The mixture was warmed to 40° C. and stirred for 2 h. After the completion of reaction was monitored by TLC, the mixture was cooled to room temperature and directly subjected to column chromatography [petroleum ether:ethyl acetate=2:3] to obtain 162 mg of light yellow solid in a yield of 79%. $^1$H NMR (400 MHz, CDCl$_3$) δ 10.18 (s, 1H), 8.22 (s, 1H), 5.28-5.24 (m, 1H), 4.36-4.28 (m, 2H), 4.24-4.16 (m, 1H), 3.75 (dd, J=12.3, 3.0 Hz, 2H), 3.60-3.54 (m, 1H), 3.32-3.22 (m, 3H), 1.33 (d, J=6.4 Hz, 9H).

(h) S—((S)-1-((7-cyano-6-((2R,6R)-2,6-dimethyl-morpholine)-5-formylbenzo[d]isoxazol-3-yl)amino)prop-2-yl)acetylthio (I-13-18)

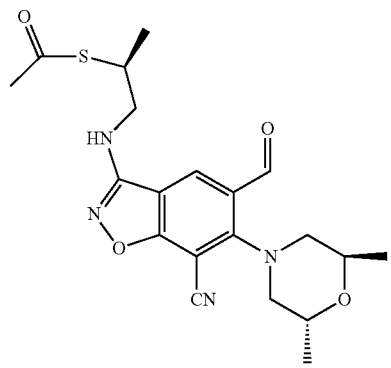 [SMILES: CC(=O)S[C@@H](C)CNc1noc2c(C#N)c(N3C[C@@H](C)O[C@H](C)C3)c(C=O)cc12]

According to the synthesis method of S-(2-((5-(1,3-dioxolan-2-yl)-6,7-difluorobenzo[d]isoxazol-3-yl)amino)ethyl)acetylthio (I-4-1), an intermediate I-12-18 (368 mg, 1.027 mmol), triphenylphosphine (808 mg, 3.082 mmol), diisopropyl azodicarboxylate (0.610 ml, 3.082 mmol) and thioacetic acid (0.220 ml, 3.082 mmol) were used as raw materials to prepare 150 mg of light yellow solid in a yield of 35%. $^1$H NMR (400 MHz, CDCl$_3$) δ 10.19 (s, 1H), 8.15 (s, 1H), 5.14 (t, J=5.3 Hz, 1H), 4.36-4.28 (m, 2H), 3.95-3.86 (m, 1H), 3.75 (dd, J=12.2, 2.7 Hz, 2H), 3.72-3.65 (m, 1H), 3.55-3.45 (m, 1H), 3.25 (dd, J=12.4, 5.8 Hz, 2H), 2.38 (s, 3H), 1.43 (d, J=7.2 Hz, 3H), 1.33 (d, J=6.4 Hz, 6H).

(i) 6-((2R,6R)-2,6-dimethylmorpholine)-5-formyl-3-((S)-5-methyl-2-oxothiazol-3-yl)benzo[d]isoxazole-7-nitrile (I-15-18)

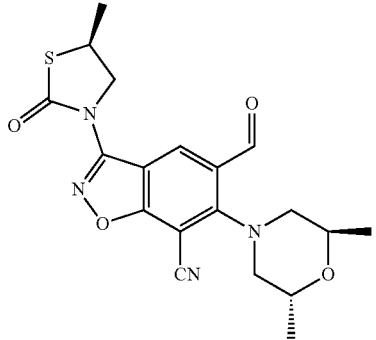 [SMILES: C[C@@H]1CN(c2c(C=O)cc3c(N4C[C@H](C)SC4=O)noc3c2C#N)C[C@@H](C)O1]

According to the synthesis method of 3-(5-(1,3-dioxolan-2-yl)-6,7-difluorobenzo[d]isoxazol-3-yl)tetrahydrothiazol-2-one (I-6-1), an intermediate I-13-18 (150 mg, 0.360 mmol), sodium hydroxide (29 mg, 0.720 mmol), dithiothreitol (28 mg, 0.180 mmol), N,N-carbonyl diimidazole (117 mg, 0.720 mmol), and 4-dimethylaminopyridine (44 mg, 0.360 mmol) were used as raw materials to prepare 52 mg of white solid in a yield of 62%. $^1$H NMR (400 MHz, CDCl$_3$) δ 10.06 (s, 1H), 8.86 (s, 1H), 4.42 (dd, J=10.9, 6.9 Hz, 1H), 4.38-4.32 (m, 2H), 4.15-4.09 (m, 1H), 3.96 (dd, J=10.8, 6.5 Hz, 1H), 3.79 (dd, J=12.9, 3.0 Hz, 2H), 3.22 (dd, J=12.6, 5.8 Hz, 2H), 1.65 (d, J=6.6 Hz, 3H), 1.32 (d, J=6.4 Hz, 6H).

(j) (2R,4S,4aS)-2,4-dimethyl-8-((S)-5-methyl-2-oxothiazol-3-yl)-2',4',6'-trioxo-1,1',2,3',4, 4a,4',6'-octahydro-2'H,6H-spiro[isoxazole[4,5-g][1,4]oxazine[4,3-a]quinoline-5,5'-pyrimidine]-11-nitrile (Compound 18)

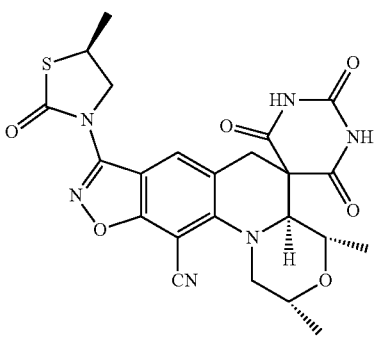

According to the synthesis method of compound 1, an intermediate I-15-18 (66 mg, 0.165 mmol) and barbituric acid (25 mg, 0.198 mmol) were used as raw materials to prepare 52 mg of light yellow solid in a yield of 62%. $^1$H NMR (400 MHz, DMSO) δ 11.82 (s, 1H), 11.62 (s, 1H), 7.77 (s, 1H), 4.56 (d, J=13.0 Hz, 1H), 4.35 (dd, J=10.6, 7.0 Hz, 1H), 4.20 (dt, J=13.5, 6.7 Hz, 1H), 4.05 (d, J=8.8 Hz, 1H), 3.94-3.80 (m, 2H), 3.77-3.71 (m, 1H), 3.66 (dq, J=12.6, 6.2 Hz, 1H), 3.27 (dd, J=14.6, 10.3 Hz, 1H), 2.86 (d, J=13.4 Hz, 1H), 1.50 (d, J=6.6 Hz, 3H), 1.19 (d, J=6.5 Hz, 3H), 0.93 (d, J=6.3 Hz, 3H); $^{13}$C NMR (151 MHz, DMSO) δ 171.28, 170.54, 167.69, 166.16, 153.64, 150.99, 149.47, 127.39, 121.17, 115.08, 104.49, 75.88, 72.40, 72.23, 65.45, 56.01, 55.96, 52.20, 38.52, 37.76, 20.18, 18.09, 17.71; MS(ESI) m/z: [(M−1)$^-$, 509.2].

Example 19: (2R,4S,4aS)-8-((S)-5-ethyl-2-oxothiazol-3-yl)-11-fluoro-2,4-dimethyl-1,2,4, 4a-tetrahydro-2'H,6H-spiro[isoxazole[4,5-g][1,4]oxazine[4,3-a]quinoline-5,5'-pyrimidine]-2', 4',6'(1'H,3'H)-trione (Compound 19)

(a) (R)-1-((5-(1,3-dioxolan-2-yl)-6,7-difluorobenzo[d]isoxazol-3-yl)amino)sec-butanol (I-3-19)

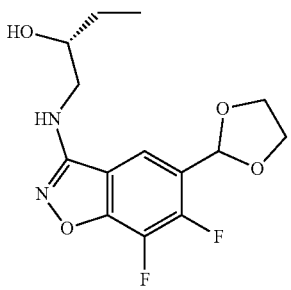 [SMILES: CC[C@@H](O)CNc1noc2c(F)c(F)c(C3OCCO3)cc12]

According to the synthesis method of intermediate I-3-1, an intermediate A (500 mg, 2.024 mmol), N-chlorosuccinimide (324 mg, 2.429 mmol), (R)-1-amino-2-butanol (540 mg, 6.072 mmol) and cesium carbonate (2.64 g, 8.096 mmol) were used as raw materials to prepare 292 mg of white solid in a yield of 46%. $^1$H NMR (400 MHz, CDCl$_3$) δ 7.49 (dd, J=5.4, 1.3 Hz, 1H), 6.11 (s, 1H), 4.85 (s, 1H), 4.20-4.08 (m, 4H), 3.95-3.87 (m, 1H), 3.61 (ddd, J=13.4, 7.0, 3.1 Hz, 1H), 3.29 (ddd, J=13.2, 8.3, 4.6 Hz, 1H), 1.65-1.56 (m, 2H), 1.04 (t, J=7.5 Hz, 3H).

(b) (S)—S-(1-((5-(1,3-dioxolan-2-yl)-6,7-difluorobenzo[d]isoxazol-3-yl)amino)2-butyl) acetylthio (I-4-19)

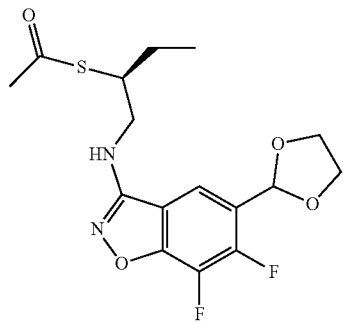 [SMILES: CC[C@@H](CNc1noc2c(F)c(F)c(C3OCCO3)cc12)SC(C)=O]

According to the synthesis method of S-(2-((5-(1,3-dioxolan-2-yl)-6,7-difluorobenzo[d]isoxazol-3-yl)amino)ethyl)acetylthio (I-4-1), an intermediate I-3-19 (280 mg, 0.891 mmol), triphenylphosphine (701 mg, 2.674 mmol), diisopropyl azodicarboxylate (0.530 ml, 2.674 mmol) and thioacetic acid (0.190 ml, 2.674 mmol) were used as raw materials to prepare 282 mg of white solid in a yield of 85%. $^1$H NMR (400 MHz, CDCl$_3$) δ 7.45 (d, J=4.2 Hz, 1H), 6.07

(s, 1H), 5.02 (t, J=5.2 Hz, 1H), 4.18-4.06 (m, 4H), 3.75-3.63 (m, 2H), 3.54-3.46 (m, 1H), 2.36 (s, 3H), 1.82-1.76 (m, 1H), 1.70-1.61 (m, 1H), 1.02 (t, J=7.4 Hz, 3H).

(c) (S)-3-(5-(dioxolan-2-yl)-6,7-difluorobenzo[d]isoxazol-3-yl)-5-ethylthiazol-2-one (I-6-19)

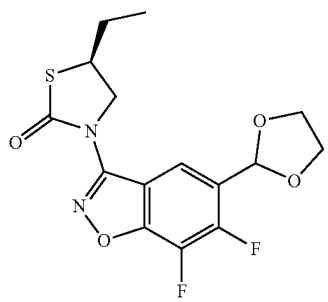 [SMILES: CC[C@H]1CN(c2noc3c(F)c(F)c(C4OCCO4)cc23)C(=O)S1]

According to the synthesis method of 3-(5-(1,3-dioxolan-2-yl)-6,7-difluorobenzo[d]isoxazol-3-yl)tetrahydrothiazol-2-one (I-6-1), an intermediate I-4-19 (330 mg, 0.891 mmol), sodium hydroxide (71 mg, 1.782 mmol), dithiothreitol (137 mg, 0.891 mmol), N,N-carbonyl diimidazole (289 mg, 1.782 mmol), and 4-dimethylaminopyridine (109 mg, 0.891 mmol) were used as raw materials to prepare 180 mg of white solid in a yield of 57%. $^1$H NMR (400 MHz, CDCl$_3$) δ 8.19 (dd, J=5.9, 1.8 Hz, 1H), 6.15 (s, 1H), 4.40 (dd, J=10.9, 7.1 Hz, 1H), 4.22-4.08 (m, 4H), 4.04 (dd, J=10.9, 6.5 Hz, 1H), 3.93 (dt, J=13.4, 6.5 Hz, 1H), 2.02-1.89 (m, 2H), 1.12 (t, J=7.4 Hz, 3H).

(d) (S)-3-(5-ethyl-2-oxothiazol-3-yl)-6,7-difluorobenzo[d]isoxazole-5-carbaldehyde (I-7-19)

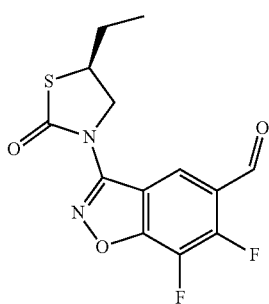 [SMILES: CC[C@H]1CN(c2noc3c(F)c(F)c(C=O)cc23)C(=O)S1]

According to the synthesis method of 6,7-difluoro-3-(2-oxothiazolin-3-yl)benzo[d]isoxazole-5-carbaldehyde (I-7-1), an intermediate I-6-19 (125 mg, 0.351 mmol) and 6 M hydrochloric acid (3 ml) were used as raw materials to prepare 100 mg of white solid in a yield of 91%. $^1$H NMR (400 MHz, CDCl$_3$) δ 10.30 (s, 1H), 8.63 (dd, J=5.8, 1.8 Hz, 1H), 4.41 (dd, J=10.9, 7.0 Hz, 1H), 4.04 (dd, J=10.9, 6.5 Hz, 1H), 3.96 (dt, J=13.3, 6.5 Hz, 1H), 2.03-1.89 (m, 2H), 1.13 (t, J=7.4 Hz, 3H).

(e) 6-((2R,6R)-2,6-dimethylmorpholine)-3-((S)-5-ethyl-2-oxothiazol-3-yl)-7-fluorobenzo[d]isoxazole-5-carbaldehyde (I-8-19)

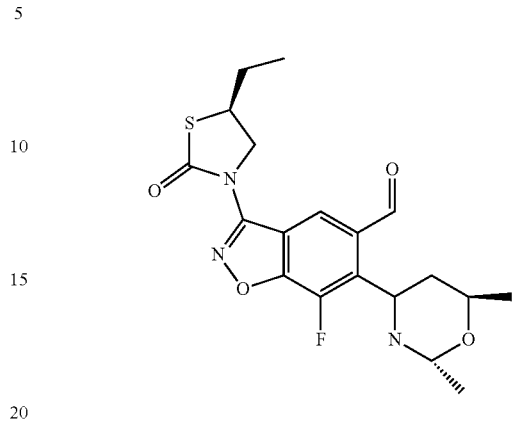

According to the synthesis method of 6-((2R,6R)-2,6-dimethylmorpholine)-7-fluoro-3-(2-oxothiazolin-3-yl)benzo[d]isoxazole-5-carbaldehyde (I-8-1), an intermediate I-7-19 (100 mg, 0.320 mmol), 2R,6R-dimethylmorpholine (0.110 ml, 0.800 mmol), and N,N-diisopropylethylamine (0.164 ml, 0.960 mmol) were used as raw materials to prepare 80 mg of yellowish white solid in a yield of 61%. $^1$H NMR (400 MHz, CDCl$_3$) δ 10.40 (s, 1H), 8.50 (d, J=1.1 Hz, 1H), 4.40 (dd, J=10.8, 7.0 Hz, 1H), 4.29-4.21 (m, 2H), 4.02 (dd, J=10.8, 6.6 Hz, 1H), 3.94 (dt, J=13.4, 6.5 Hz, 1H), 3.44 (dt, J=5.3, 2.4 Hz, 2H), 3.05 (dd, J=11.4, 5.0 Hz, 2H), 2.02-1.90 (m, 2H), 1.34 (d, J=6.5 Hz, 6H), 1.12 (t, J=7.4 Hz, 3H).

(f) (2R,4S,4aS)-8-((S)-5-ethyl-2-oxothiazol-3-yl)-11-fluoro-2,4-dimethyl-1,2,4,4a-tetrahydro-2'H,6H-spiro[isoxazole[4,5-g][1,4]oxazine[4,3-a]quinoline-5,5'-pyrimidine]-2',4',6'(1'H,3'H)-trione (Compound 19)

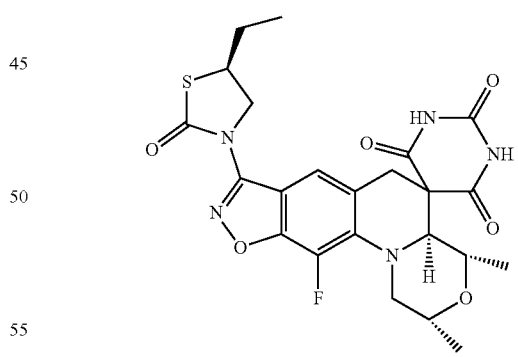

According to the synthesis method of compound 1, an intermediate I-8-19 (75 mg, 0.184 mmol) and barbituric acid (28 mg, 0.221 mmol) were used as raw materials to prepare 63 mg of light yellow solid in a yield of 66%. $^1$H NMR (400 MHz, DMSO) δ 11.69 (s, 2H), 7.41 (s, 1H), 4.34 (dd, J=10.6, 7.0 Hz, 1H), 4.11-4.03 (m, 2H), 3.95 (dd, J=11.3, 7.6 Hz, 2H), 3.82-3.74 (m, 1H), 3.70-3.59 (m, 2H), 3.15-3.06 (m, 1H), 2.90 (d, J=14.1 Hz, 1H), 1.88 (dd, J=7.4, 6.1 Hz, 1H), 1.83-1.72 (m, 1H), 1.14 (d, J=6.2 Hz, 3H), 0.97 (t, J=7.3 Hz, 3H), 0.89 (d, J=6.3 Hz, 3H); $^{13}$C NMR (126 MHz, DMSO) δ 171.40, 171.17, 168.13, 154.00 (d, J=13.0 Hz), 153.90, 149.98, 135.25, 133.76 (d, J=239.1 Hz), 122.85, 118.62, 107.33, 72.57, 72.13, 64.83, 56.73 (d, J 10=9.3 Hz), 54.80, 53.37, 45.52, 38.98, 28.05, 18.63, 18.59, 11.93; MS (ESI) m/z: [(M−1)⁻, 516.1].

Example 20: (2R,4S,4aS)-11-fluoro-2,4-dimethyl-8-((R)-5-((methanesulfonyl)methyl)-2-oxothiazol-3-yl)-1,2,4,4a-tetrahydro-2'H,6H-spiro[isoxazole[4,5-g][1,4]oxazine[4,3-a]quinoline-5,5'-pyrimidine]-2',4',6'(1'H,3'H)-trione (Compound 20)

(a) methyl (R)-(3-(5-(1,3-dioxolan-2-yl)-6,7-difluorobenzo[d]isoxazol-3-yl)-2-oxothiazol-5-yl)mesylate (I-1-20)

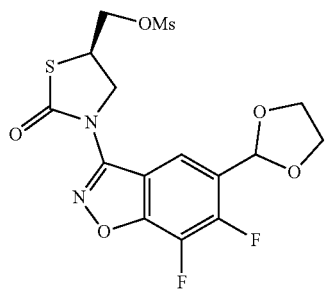 [SMILES: CS(=O)(=O)OC[C@H]1CN(c2noc3c(F)c(F)c(C4OCCO4)cc23)C(=O)S1]

According to the synthesis method of intermediate I-3-10, an intermediate I-8-6 (462 mg, 1.290 mmol), methanesulfonyl chloride (0.150 ml, 1.94 mmol) and N,N-diisopropylethylamine (0.427 ml, 2.580 mmol) were used as raw materials to prepare 540 mg of colorless oil in a yield of 96%. ¹H NMR (400 MHz, CDCl₃) δ 8.16 (dd, J=5.9, 1.6 Hz, 1H), 6.15 (s, 1H), 4.53-4.41 (m, 3H), 4.34 (dd, J=11.7, 3.0 Hz, 1H), 4.26-4.22 (m, 1H), 4.22-4.09 (m, 4H), 3.12 (s, 3H).

(b) (R)-3-(5-(1,3-dioxolan-2-yl)-6,7-difluorobenzo[d]isoxazol-3-yl)-5-((methylthio)methyl)thiazol-2-one (I-2-20)

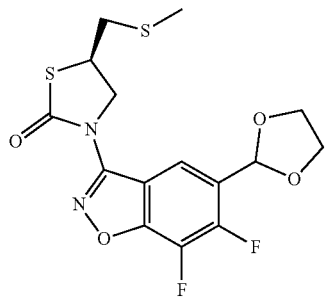 [SMILES: CSC[C@H]1CN(c2noc3c(F)c(F)c(C4OCCO4)cc23)C(=O)S1]

An intermediate I-1-20 (355 mg, 0.813 mmol) was dissolved in 5 ml of N,N-dimethylformamide at room temperature. In an ice bath, a 20% aqueous solution of sodium methyl mercaptan (0.570 ml) was added dropwise and stirred at room temperature for 1 h. After TLC detection showed that the reaction was completed, water was added and the mixture was extracted with ethyl acetate. The combined organic layers were washed with water and saturated brine, dried over anhydrous sodium sulfate, concentrated under reduced pressure and purified by column chromatography [petroleum ether:ethyl acetate=3:1] to obtain 139 mg of colorless oil in a yield of 43%. ¹H NMR (400 MHz, CDCl₃) δ 8.17 (dd, J=5.8, 1.7 Hz, 1H), 6.15 (s, 1H), 4.45 (dd, J=11.3, 7.0 Hz, 1H), 4.27 (dd, J=11.3, 4.9 Hz, 1H), 4.23-4.07 (m, 5H), 3.04-2.92 (m, 2H), 2.23 (s, 3H).

(c) (R)-3-(5-(1,3-dioxolan-2-yl)-6,7-difluorobenzo[d]isoxazol-3-yl)-5-((methanesulfonyl) methyl)thiazol-2-one (I-3-20)

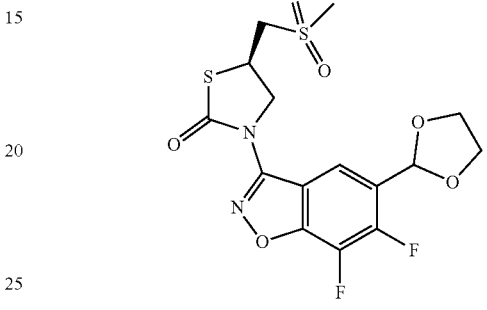

At room temperature, an intermediate I-2-20 (139 mg, 0.358 mmol) was dissolved in a mixed solution of 4 ml of methanol and 1 ml of water. Under an ice bath, sodium tungstate hydrate (12 mg, 0.036 mmol) and hydrogen peroxide (3 ml) were added and stirred for 30 min. After TLC detection showed that the reaction was completed, the reaction was quenched by adding excess sodium thiosulfate. Water was added and the mixture was extracted with ethyl acetate. The combined organic layers were washed with water and saturated brine, dried over anhydrous sodium sulfate, concentrated under reduced pressure and purified by column chromatography [petroleum ether:ethyl acetate=3:1] to obtain 62 mg of colorless oil in a yield of 41%. ¹H NMR (400 MHz, CDCl₃) δ 8.10 (dd, J=5.8, 1.7 Hz, 1H), 6.13 (s, 1H), 4.59-4.50 (m, 2H), 4.39 (dd, J=10.8, 4.3 Hz, 1H), 4.20-4.06 (m, 4H), 3.63 (dd, J=13.9, 7.3 Hz, 1H), 3.53 (dd, J=13.9, 6.0 Hz, 1H), 3.06 (s, 3H).

(d) (R)-6,7-difluoro-3-(5-((methanesulfonyl)methyl)-2-oxothiazol-3-yl)benzo[d]isoxazole-5-carbaldehyde (I-4-20)

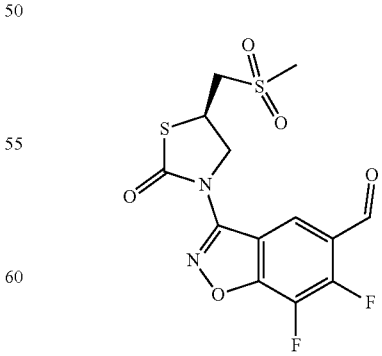

According to the synthesis method of intermediate I-7-1, an intermediate I-3-20 (60 mg, 0.143 mmol) and hydrochloric acid (2 ml) were used as raw materials to prepare 53 mg of white solid in a yield of 98%. ¹H NMR (400 MHz, CDCl₃) δ 10.32 (s, 1H), 8.56 (d, J=4.9 Hz, 1H), 4.63-4.54 (m, 2H), 4.44 (dd, J=9.6, 2.9 Hz, 1H), 3.66 (dd, J=14.2, 7.9 Hz, 1H), 3.57 (dd, J=13.8, 5.1 Hz, 1H), 3.09 (s, 3H).

(e) 6-((2R,6R)-2,6-dimethylmorpholine)-7-fluoro-3-((R)-5-((methanesulfonyl)methyl)-2-oxothiazol-3-yl)benzo[d]isoxazole-5-carbaldehyde (I-5-20)

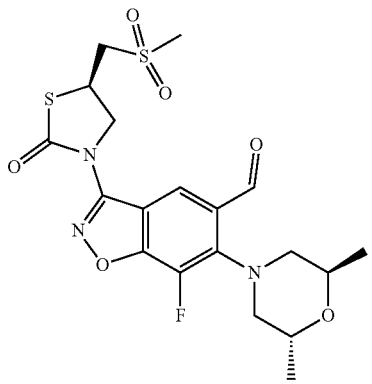 [SMILES: C[C@@H]1CN(c2c(C=O)cc3c(N4C[C@H](CS(C)(=O)=O)SC4=O)noc3c2F)C[C@@H](C)O1]

According to the synthesis method of intermediate I-8-1, an intermediate I-5-20 (50 mg, 0.133 mmol), 2R,6R-dimethylmorpholine (0.036 ml, 0.266 mmol), and N,N-diisopropyl ethylamine (0.066 ml, 0.399 mmol) were used as raw materials to prepare 42 mg of white solid in a yield of 67%. ¹H NMR (400 MHz, CDCl₃) δ 10.41 (s, 1H), 8.43 (s, 1H), 4.62-4.52 (m, 2H), 4.42 (dd, J=10.5, 3.5 Hz, 1H), 4.30-4.22 (m, 2H), 3.66 (dd, J=13.8, 7.6 Hz, 1H), 3.57 (dd, J=14.2, 5.8 Hz, 1H), 3.45 (d, J=12.4 Hz, 2H), 3.11-3.03 (m, 5H), 1.35 (d, J=6.5 Hz, 6H).

(f) (2R,4S,4aS)-11-fluoro-2,4-dimethyl-8-((R)-5-((methanesulfonyl)methyl)-2-oxothiazol-3-yl)-1,2,4,4a-tetrahydro-2'H,6H-spiro[isoxazole[4,5-g][1,4]oxazine[4,3-a]quinoline-5,5'-pyrimidine]-2',4',6'(1'H,3'H)-trione (Compound 20)

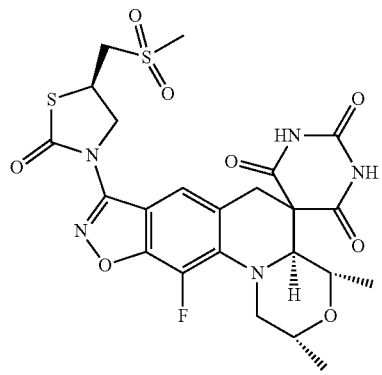

According to the synthesis method of compound 1, an intermediate I-5-20 (40 mg, 0.085 mmol) and barbituric acid (12 mg, 0.093 mmol) were used as raw materials to prepare 30 mg of light yellow solid in a yield of 60%. ¹H NMR (400 MHz, DMSO) δ 11.84 (s, 1H), 11.47 (s, 1H), 7.43 (s, 1H), 4.67-4.58 (m, 1H), 4.43 (dd, J=11.0, 7.3 Hz, 1H), 4.21 (dd, J=10.9, 7.1 Hz, 1H), 4.11 (d, J=12.9 Hz, 1H), 4.00-3.92 (m, 2H), 3.77 (dd, J=14.2, 7.6 Hz, 2H), 3.71-3.63 (m, 2H), 3.16-3.06 (m, 4H), 2.92 (d, J=14.2 Hz, 1H), 1.15 (d, J=6.2 Hz, 3H), 0.89 (d, J=6.3 Hz, 3H); ¹³C NMR (126 MHz, DMSO) δ 171.38, 170.67, 168.12, 154.04 (d, J=12.9 Hz), 153.78, 149.95, 135.31, 133.75 (d, J=239.1 Hz), 122.90, 118.72, 107.23, 72.57, 72.13, 64.87, 57.14, 56.74 (d, J=9.4 Hz), 53.82, 53.39, 41.43, 38.95, 36.97, 18.63, 18.60; MS (EI) m/z: [M⁺, 581].

Example 21: (2R,4S,4aS)-11-fluoro-2,4-dimethyl-8-((3aS,6aR)-2-oxotetrahydro-2H-cyclopentane[d]thiazol-3(3aH)-yl)-1,2,4,4a-tetrahydro-2'H,6H-spiro[isoxazole[4,5-g][1,4]oxazine [4,3-a]quinoline-5,5'-pyrimidine]-2',4',6'(1'H,3'H)-trione (Compound 21)

(a) (1S,2S)-2-((5-(1,3-dioxolan-2-yl)-6,7-difluorobenzo[d]isoxazol-3-yl)amino))cyclopentanol (I-3-21)

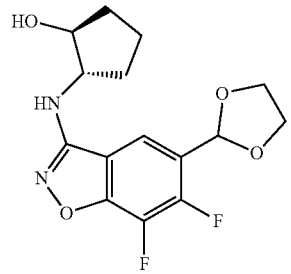 [SMILES: O[C@H]1CCC[C@@H]1Nc1noc2c(F)c(F)c(C3OCCO3)cc12]

According to the synthesis method of intermediate I-3-1, an intermediate A (700 mg, 2.833 mmol), N-chlorosuccinimide (454 mg, 3.400 mmol), (1S, 2S)-2-aminocyclopentanol hydrochloride (585 mg, 4.250 mmol), triethylamine (1.181 ml, 8.499 mmol) and cesium carbonate (3.692 g, 11.332 mmol) were used as raw materials to prepare 692 mg of white solid in a yield of 75%. ¹H NMR (400 MHz, CD₃OD) δ 7.97 (d, J=5.7 Hz, 1H), 7.17 (d, J=6.4 Hz, 1H), 6.07 (s, 1H), 4.80 (d, J=4.2 Hz, 1H), 4.10-4.00 (m, 5H), 3.68-3.61 (m, 1H), 2.16-2.05 (m, 1H), 1.90-1.81 (m, 1H), 1.74-1.65 (m, 2H), 1.59-1.46 (m, 2H).

(b) S-((1R,2S)-2-((5-(1,3-dioxolan-2-yl)-6,7-difluorobenzo[d]isoxazol-3-yl)amino)cyclopentyl)acetylthio (I-4-21)

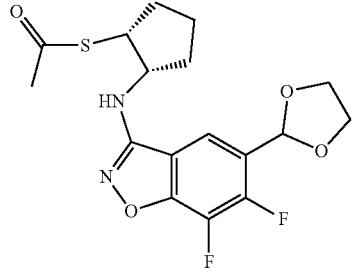 [SMILES: CC(=O)S[C@@H]1CCC[C@@H]1Nc1noc2c(F)c(F)c(C3OCCO3)cc12]

According to the synthesis method of intermediate I-4-1, an intermediate I-3-21 (400 mg, 1.227 mmol), triphenylphosphine (965 mg, 3.680 mmol), diisopropyl azodicarboxylate (0.720 ml, 3.680 mmol) and thioacetic acid (0.260 ml, 3.680 mmol) were used as raw materials to prepare 470 mg of white solid in a yield of 99%. ¹H NMR (400 MHz, CDCl₃) δ 7.44 (dd, J=5.3, 1.4 Hz, 1H), 6.11 (s, 1H), 4.63 (d, J=6.9 Hz, 1H), 4.37-4.29 (m, 1H), 4.23-4.10 (m, 5H), 2.35 (s, 3H), 2.32-2.23 (m, 2H), 1.93-1.83 (m, 2H), 1.82-1.73 (m, 2H).

(c) (3aS,6aR)-3-(5-(1,3-dioxolan-2-yl)-6,7-difluorobenzo[d]isoxazol-3-yl)hexahydro-2H-cyclopentane[d]thiazol-2-one (I-6-21)

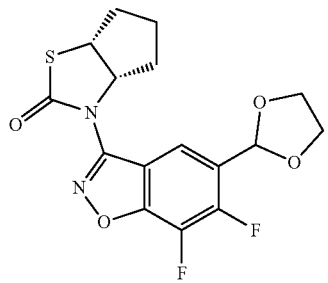 [SMILES: O=C1S[C@@H]2CCC[C@@H]2N1c1noc2c(F)c(F)c(C3OCCO3)cc12]

According to the synthesis method of intermediate I-6-1, an intermediate I-4-21 (470 mg, 1.224 mmol), sodium hydroxide (98 mg, 2.448 mmol), dithiothreitol (188 mg, 1.224 mmol), N,N-carbonyldiimidazole (397 mg, 2.448 mmol), and 4-dimethylaminopyridine (150 mg, 1.224 mmol) were used as raw materials to prepare 363 mg of white solid in a yield of 81%. ¹H NMR (400 MHz, CDCl₃) δ 8.54 (dd, J=5.9, 1.7 Hz, 1H), 6.15 (s, 1H), 5.28-5.23 (m, 1H), 5.02-4.97 (m, 1H), 4.21-4.08 (m, 4H), 2.31-2.22 (m, 2H), 1.92-1.80 (m, 4H).

(d) 6,7-difluoro-3-((3aS,6aR)-2-oxotetrahydro-2H-cyclopentane[d]thiazol-3(3aH)-yl)benzo[d]isoxazole-5-carbaldehyde (I-7-21)

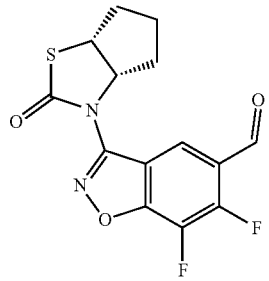 [SMILES: O=Cc1cc2c(N3C(=O)S[C@@H]4CCC[C@@H]43)noc2c(F)c1F]

According to the synthesis method of intermediate I-7-1, an intermediate I-6-21 (320 mg, 0.869 mmol) and 6M hydrochloric acid (6 ml) were used as raw materials to prepare 280 mg of white solid in a yield of 98%. ¹H NMR (400 MHz, CDCl₃) δ 10.29 (s, 1H), 8.62 (dd, J=5.8, 1.7 Hz, 1H), 5.07-5.00 (m, 1H), 4.38-4.32 (m, 1H), 2.33-2.18 (m, 2H), 2.11-1.98 (m, 3H), 1.87-1.78 (m, 1H).

(e) 6-((2R,6R)-2,6-dimethylmorpholine)-7-fluoro-3-((3aS,6aR)-2-oxotetrahydro-2H-cyclopentane[d]thiazol-3(3aH)-yl)benzo[d]isoxazole-5-carbaldehyde (I-8-21)

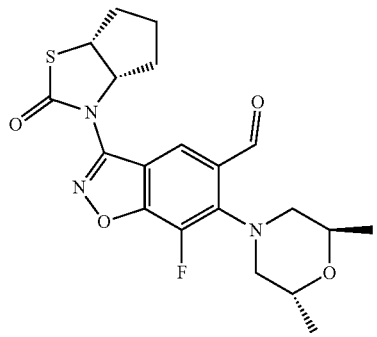 [SMILES: C[C@@H]1CN(c2c(C=O)cc3c(N4C(=O)S[C@@H]5CCC[C@@H]54)noc3c2F)C[C@@H](C)O1]

According to the synthesis method of intermediate I-8-1, an intermediate I-7-21 (280 mg, 0.864 mmol), 2R,6R-dimethylmorpholine (0.230 ml, 1.728 mmol), and N,N-diisopropyl ethylamine (0.440 ml, 2.592 mmol) were used as raw materials to prepare 161 mg of light yellow solid in a yield of 45%. ¹H NMR (400 MHz, CDCl₃) δ 10.40 (s, 1H), 8.47 (d, J=1.1 Hz, 1H), 5.06-5.00 (m, 1H), 4.35-4.30 (m, 1H), 4.29-4.22 (m, 2H), 3.43 (d, J=11.6 Hz, 2H), 3.05 (dd, J=11.4, 5.0 Hz, 2H), 2.28-2.20 (m, 2H), 2.11-2.00 (m, 3H), 1.86-1.77 (m, 1H), 1.34 (d, J=6.5 Hz, 6H).

(f) (2R,4S,4aS)-11-fluoro-2,4-dimethyl-8-((3aS,6aR)-2-oxotetrahydro-2H-cyclopentane[d]thiazol-3(3aH)-yl)-1,2,4,4a-tetrahydro-2'H,6H-spiro[isoxazole[4,5-g][1,4]oxazine[4,3-a]quinoline-5,5'-pyrimidine]-2',4',6'(1'H,3'H)-trione (Compound 21)

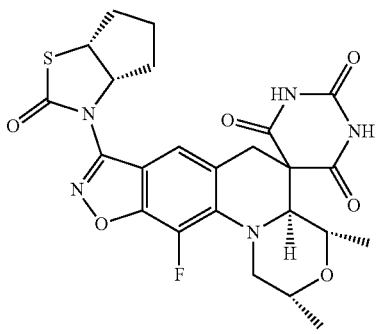

According to the synthesis method of compound 1, an intermediate I-8-21 (143 mg, 0.341 mmol) and barbituric acid (53 mg, 0.409 mmol) were used as raw materials to prepare 120 mg of white solid in a yield of 66%. ¹H NMR (400 MHz, DMSO) δ 11.71 (s, 2H), 7.37 (s, 1H), 4.97-4.92 (m, 1H), 4.40-4.34 (m, 1H), 4.08 (d, J=12.9 Hz, 1H), 3.92 (d, J=8.8 Hz, 1H), 3.83-3.73 (m, 1H), 3.71-3.57 (m, 2H), 3.14-3.02 (m, 1H), 2.89 (d, J=14.2 Hz, 1H), 2.16-2.02 (m, 2H), 1.89-1.75 (m, 3H), 1.73-1.62 (m, 1H), 1.13 (d, J=6.1 Hz, 3H), 0.88 (d, J=6.3 Hz, 3H); ¹³C NMR (126 MHz, DMSO) δ 171.38, 171.26, 168.15, 153.94 (d, J=12.9 Hz), 153.66, 149.90, 135.19, 133.75 (d, J=239.4 Hz), 122.85, 118.42, 107.85, 72.60, 72.15, 65.59, 64.82, 56.74 (d, J=9.3

Hz), 53.31, 44.79, 38.97, 35.07, 33.12, 23.54, 18.62, 18.56; MS (ESI) m/z: [(M−1)⁻, 528.2].

Example 22: (2R,4S,4aS)-11-fluoro-2,4-dimethyl-8-((3aR,6aS)-2-oxotetrahydro-2H-cyclopentane[d]thiazol-3(3aH)-yl)-1,2,4,4a-tetrahydro-2'H,6H-spiro[isoxazole[4,5-g][1,4]oxazine [4,3-a]quinoline-5,5'-pyrimidine]-2',4',6'(1'H,3'H)-trione (Compound 22)

(a) (1R,2R)-2-((5-(1,3-dioxolan-2-yl)-6,7-difluorobenzo[d]isoxazol-3-yl)amino))cyclopentanol (I-3-22)

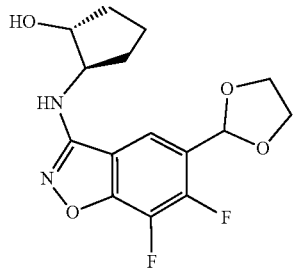 [SMILES: O[C@@H]1CCC[C@H]1Nc1noc2c(F)c(F)c(C3OCCO3)cc12]

According to the synthesis method of intermediate I-3-1, an intermediate A (1.2 g, 4.840 mmol), N-chlorosuccinimide (778 mg, 5.830 mmol), (1R,2R)-2-aminocyclopentanol hydrochloride (1 g, 7.270 nmol), triethylamine (1.681 ml, 12.100 mmol) and cesium carbonate (7.884 g, 24.200 mmol) were used as raw materials to prepare 848 mg of white solid in a yield of 55%. ¹H NMR (400 MHz, DMSO) δ 7.98 (d, J=5.5 Hz, 1H), 7.18 (d, J=6.4 Hz, 1H), 6.08 (s, 1H), 4.81 (d, J=4.2 Hz, 1H), 4.11-4.00 (m, 5H), 3.69-3.62 (m, 1H), 2.16-2.06 (m, 1H), 1.92-1.81 (m, 1H), 1.77-1.64 (m, 2H), 1.60-1.47 (m, 2H).

(b) S-((1S,2R)-2-((5-(1,3-dioxolan-2-yl)-6,7-difluorobenzo[d]isoxazol-3-yl)amino)cyclopentyl)acetylthio (I-4-22)

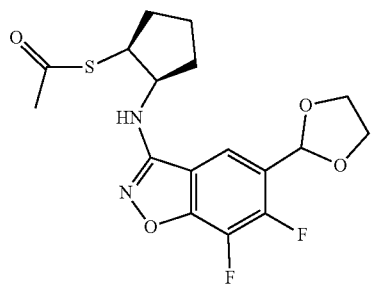 [SMILES: CC(=O)S[C@H]1CCC[C@H]1Nc1noc2c(F)c(F)c(C3OCCO3)cc12]

According to the synthesis method of intermediate I-4-1, an intermediate I-3-22 (625 mg, 1.940 mmol), triphenylphosphine (1.119 g, 4.270 mmol), diisopropyl azodicarboxylate (0.840 ml, 4.270 mmol) and thioacetic acid (0.303 ml, 4.270 mmol) were used as raw materials to prepare 650 mg of light yellow solid in a yield of 87%. ¹H NMR (400 MHz, CDCl₃) δ 7.44 (dd, J=5.3, 1.4 Hz, 1H), 6.11 (s, 1H), 4.63 (d, J=6.9 Hz, 1H), 4.37-4.29 (m, 1H), 4.23-4.10 (m, 5H), 2.35 (s, 3H), 2.32-2.23 (m, 2H), 1.93-1.83 (m, 2H), 1.82-1.73 (m, 2H).

(c) (3aR,6aS)-3-(5-(1,3-dioxolan-2-yl)-6,7-difluorobenzo[d]isoxazol-3-yl)hexahydro-2H-cyclopentane[d]thiazol-2-one (I-6-22)

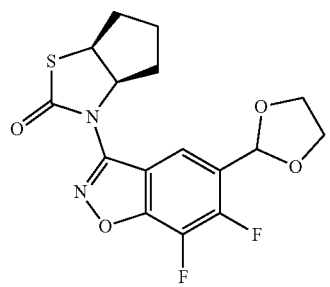 [SMILES: O=C1S[C@H]2CCC[C@H]2N1c1noc2c(F)c(F)c(C3OCCO3)cc12]

According to the synthesis method of intermediate I-6-1, an intermediate I-4-22 (650 mg, 1.690 mmol), sodium hydroxide (135 mg, 3.380 mmol), dithiothreitol (260 mg, 1.690 mmol), N,N-carbonyldiimidazole (547 mg, 3.380 mmol), and 4-dimethylaminopyridine (206 mg, 1.690 mmol) were used as raw materials to prepare 510 mg of white solid in a yield of 82%. ¹H NMR (400 MHz, CDCl₃) δ 8.16 (d, J=5.9 Hz, 1H), 6.14 (s, 1H), 5.04 (td, J=7.9, 3.6 Hz, 1H), 4.32 (td, J=7.9, 2.8 Hz, 1H), 4.24-4.05 (m, 4H), 2.31-2.16 (m, 2H), 2.12-1.94 (m, 3H), 1.86-1.75 (m, 1H).

(d) 6,7-difluoro-3-((3aR,6aS)-2-oxotetrahydro-2H-cyclopentane[d]thiazol-3(3aH)-yl)benzo[d]isoxazole-5-carbaldehyde (I-7-22)

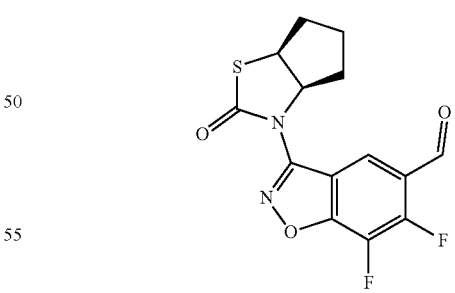

According to the synthesis method of intermediate I-7-1, an intermediate I-6-22 (500 mg, 1.360 mmol) and 6 M hydrochloric acid (8 ml) were used as raw materials to prepare 380 mg of white solid in a yield of 86%. ¹H NMR (400 MHz, CDCl₃) δ 10.29 (s, 1H), 8.62 (dd, J=5.8, 1.8 Hz, 1H), 5.03 (td, J=7.8, 3.7 Hz, 1H), 4.38-4.32 (m, 1H), 2.34-2.18 (m, 2H), 2.14-1.96 (m, 4H), 1.87-1.78 (m, 1H).

(e) 6-((2R,6R)-2,6-dimethylmorpholine)-7-fluoro-3-((3aR,6aS)-2-oxotetrahydro-2H-cyclopentane[d]thiazol-3(3aH)-yl)benzo[d]isoxazole-5-carbaldehyde (I-8-22)

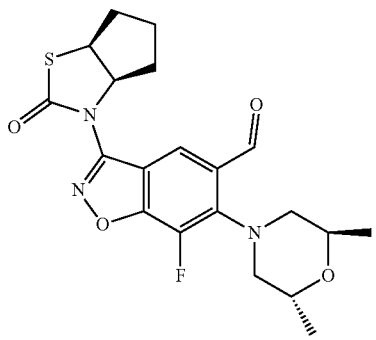 [SMILES: C[C@@H]1CN(c2c(C=O)cc3c(N4C(=O)S[C@H]5CCC[C@H]54)noc3c2F)C[C@@H](C)O1]

According to the synthesis method of intermediate I-8-1, an intermediate I-7-22 (210 mg, 0.648 mmol), 2R,6R-dimethylmorpholine (0.130 ml, 0.971 mmol), and N,N-diisopropylethylamine (0.320 ml, 1.941 mmol) were used as raw materials to prepare 192 mg of light yellow solid in a yield of 71%. $^1$H NMR (400 MHz, CDCl$_3$) δ 10.40 (s, 1H), 8.47 (s, 1H), 5.06-5.00 (m, 1H), 4.36-4.30 (m, 1H), 4.29-4.21 (m, 2H), 3.44 (d, J=11.8 Hz, 2H), 3.04 (dd, J=11.3, 5.5 Hz, 2H), 2.30-2.17 (m, 2H), 2.12-1.94 (m, 3H), 1.81 (d, J=4.1 Hz, 1H), 1.34 (d, J=6.4 Hz, 6H).

(f) (2R,4S,4aS)-11-fluoro-2,4-dimethyl-8-((3aR,6aS)-2-oxotetrahydro-2H-cyclopentane[d]thiazol-3(3aH)-yl)-1,2,4,4a-tetrahydro-2'H,6H-spiro[isoxazole[4,5-g][1,4]oxazine[4,3-a]quinoline-5,5'-pyrimidine]-2',4',6'(1'H,3'H)-trione (Compound 22)

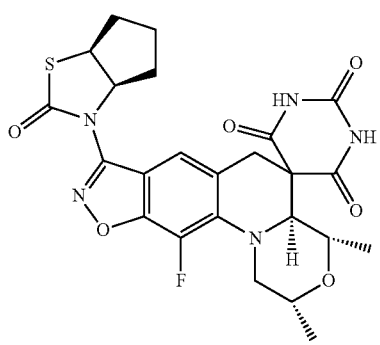

According to the synthesis method of compound 1, an intermediate I-8-22 (180 mg, 0.429 mmol) and barbituric acid (60 mg, 0.472 mmol) were used as raw materials to prepare 120 mg of white solid in a yield of 53%. $^1$H NMR (400 MHz, DMSO) δ 11.84 (s, 1H), 11.52 (s, 1H), 7.37 (s, 1H), 4.96-4.89 (m, 1H), 4.47-4.39 (m, 1H), 4.10 (d, J=14.0 Hz, 1H), 3.93 (d, J=8.6 Hz, 1H), 3.83-3.73 (m, 1H), 3.71-3.61 (m, 2H), 3.16-3.06 (m, 1H), 2.90 (d, J=14.4 Hz, 1H), 2.18-2.04 (m, 2H), 1.96-1.78 (m, 3H), 1.74-1.63 (m, 1H), 1.14 (d, J=6.1 Hz, 3H), 0.89 (d, J=6.2 Hz, 3H); $^{13}$C NMR (126 MHz, DMSO) δ 171.38, 171.15, 168.13, 153.90 (d, J=12.8 Hz), 153.75, 149.94, 135.25, 133.76 (d, J=239.1 Hz), 123.05, 118.33, 107.97, 72.58, 72.14, 65.93, 64.85, 56.74 (d, J=9.2 Hz), 53.35, 45.21, 38.97, 34.60, 33.17, 23.47, 18.64, 18.61; MS (ESI) m/z: [(M−1)$^-$, 528.2].

Example 23: (2R,4S,4aS)-11-fluoro-2,4-dimethyl-8-((3aS,6aR)-2-oxohexahydrobenzo[d]thiazol-3(2H)-yl)-1,2,4,4a-tetrahydro-2'H,6H-spiro[isoxazole[4,5-g][1,4]oxazine[4,3-a]quinoline-5,5'-pyrimidine]-2',4',6'(1'H,3'H)-trione (Compound 23)

(a) (1S,2S)-2-((5-(1,3-dioxolan-2-yl)-6,7-difluorobenzo[d]isoxazol-3-yl)amino))cyclohexanol (I-3-23)

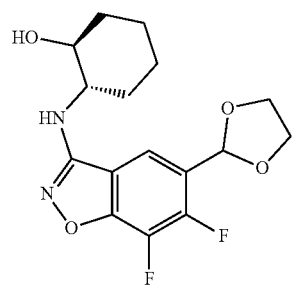 [SMILES: O[C@H]1CCCC[C@@H]1Nc1noc2c(F)c(F)c(C3OCCO3)cc12]

According to the synthesis method of intermediate I-3-1, an intermediate A (500 mg, 2.024 mmol), N-chlorosuccinimide (324 mg, 2.429 mmol), (1S, 2S)-2-aminocyclohexanol hydrochloride (399 mg, 2.631 mmol), triethylamine (0.840 ml, 6.072 mmol) and cesium carbonate (3.297 g, 10.120 mmol) were used as raw materials to prepare 377 mg of white solid in a yield of 55%. $^1$H NMR (400 MHz, DMSO) δ 8.01 (dd, J=5.6, 1.1 Hz, 1H), 7.11 (d, J=7.5 Hz, 1H), 6.09 (s, 1H), 4.71 (d, J=5.1 Hz, 1H), 4.12-4.00 (m, 4H), 3.48-3.41 (m, 1H), 3.30-3.20 (m, 1H), 2.15-2.06 (m, 1H), 1.97-1.88 (m, 1H), 1.71-1.59 (m, 2H), 1.34-1.16 (m, 4H).

(b) S-((1R,2S)-2-((5-(1,3-dioxolan-2-yl)-6,7-difluorobenzo[d]isoxazol-3-yl)amino)cyclohexyl)acetylthio (I-4-23)

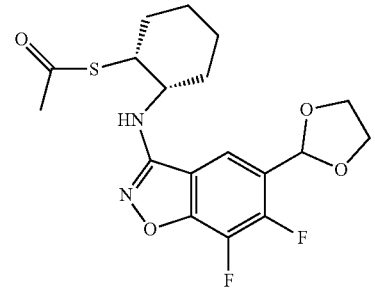 [SMILES: CC(=O)S[C@@H]1CCCC[C@@H]1Nc1noc2c(F)c(F)c(C3OCCO3)cc12]

According to the synthesis method of intermediate I-4-1, an intermediate I-3-23 (350 mg, 1.029 mmol), triphenylphosphine (810 mg, 3.087 mmol), diisopropyl azodicarboxylate (0.610 ml, 3.087 mmol) and thioacetic acid (0.220 ml, 3.087 mmol) were used as raw materials to prepare 200 mg of white solid in a yield of 49%. $^1$H NMR (400 MHz, CDCl$_3$) δ 7.42 (dd, J=5.4, 1.0 Hz, 1H), 6.10 (s, 1H), 4.74 (d, J=6.6 Hz, 1H), 4.31-4.27 (m, 1H), 4.20-4.09 (m, 4H), 4.04-3.98 (m, 1H), 2.38 (s, 3H), 2.12-1.93 (m, 4H), 1.80-1.61 (m, 4H).

(c) (3aS,6aR)-3-(5-(1,3-dioxolan-2-yl)-6,7-difluorobenzo[d]isoxazol-3-yl)hexahydrobenzo[d]thiazol-2(3H)-one (I-6-23)

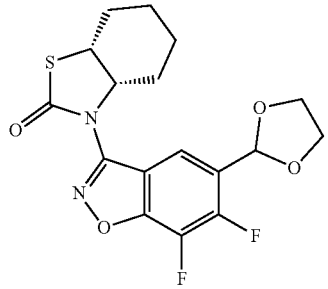 [SMILES: O=C1S[C@@H]2CCCC[C@@H]2N1c1noc2c(F)c(F)c(C3OCCO3)cc12]

According to the synthesis method of intermediate I-6-1, an intermediate I-4-23 (200 mg, 0.502 mmol), sodium hydroxide (40 mg, 1.004 mmol), dithiothreitol (77 mg, 0.502 mmol), N,N-carbonyldiimidazole (163 mg, 1.004 mmol), and 4-dimethylaminopyridine (61 mg, 0.502 mmol) were used as raw materials to prepare 50 mg of colorless oil in a yield of 26%. $^1$H NMR (400 MHz, CDCl$_3$) δ 8.11 (d, J=5.8 Hz, 1H), 6.15 (s, 1H), 4.57-4.51 (m, 1H), 4.40-4.36 (m, 1H), 4.22-4.07 (m, 4H), 2.49-2.41 (m, 1H), 2.14-2.08 (m, 1H), 2.04-1.94 (m, 2H), 1.82-1.62 (m, 4H).

(d) 6,7-difluoro-3-((3aS,6aR)-2-oxohexahydrobenzo[d]thiazol-3(2H)-yl)benzo[d]isoxazole-5-carbaldehyde (I-7-23)

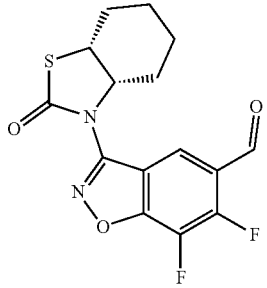 [SMILES: O=Cc1cc2c(N3C(=O)S[C@@H]4CCCC[C@@H]43)noc2c(F)c1F]

According to the synthesis method of intermediate I-7-1, an intermediate I-6-23 (50 mg, 0.131 mmol) and 6 M hydrochloric acid (3 ml) were used as raw materials to prepare 40 mg of white solid in a yield of 90%. $^1$H NMR (400 MHz, CDCl$_3$) δ 10.30 (s, 1H), 8.55 (dd, J 6.0, 1.5 Hz, 1H), 4.59-4.51 (m, 1H), 4.42-4.38 (m, 1H), 2.52-2.44 (m, 1H), 2.16-2.09 (m, 1H), 2.06-1.94 (m, 2H), 1.84-1.66 (m, 4H).

(e) 6-((2R,6R)-2,6-dimethylmorpholine)-7-fluoro-3-((3aS,6aR)-2-hexahydrobenzo[d]thiazol-3(2H)-yl)benzo[d]isoxazole-5-carbaldehyde (I-8-23)

According to the synthesis method of intermediate I-8-1, an intermediate I-7-23 (60 mg, 0.177 mmol), 2R,6R-dimethylmorpholine (0.060 ml, 0.444 mmol), and N,N-diisopropyl ethylamine (0.090 ml, 0.531 mmol) were used as raw materials to prepare 43 mg of white solid in a yield of 56%. $^1$H NMR (400 MHz, CDCl$_3$) δ 10.40 (s, 1H), 8.41 (d, J=1.1 Hz, 1H), 4.56-4.50 (m, 1H), 4.40-4.35 (m, 1H), 4.29-4.22 (m, 2H), 3.43 (d, J=12.0 Hz, 2H), 3.04 (dd, J=11.3, 5.3 Hz, 2H), 2.46-2.41 (m, 1H), 2.13-1.96 (m, 4H), 1.77-1.65 (m, 3H), 1.34 (d, J=6.5 Hz, 6H).

(f) (2R,4S,4aS)-11-fluoro-2,4-dimethyl-8-((3aS,6aR)-2-oxohexahydrobenzo[d]thiazol-3(2H)-yl)-1,2,4,4a-tetrahydro-2'H,6H-spiro[isoxazole[4,5-g][1,4]oxazine[4,3-a]quinoline-5,5'-pyrimidine]-2',4',6'(1'H,3'H)-trione (Compound 23)

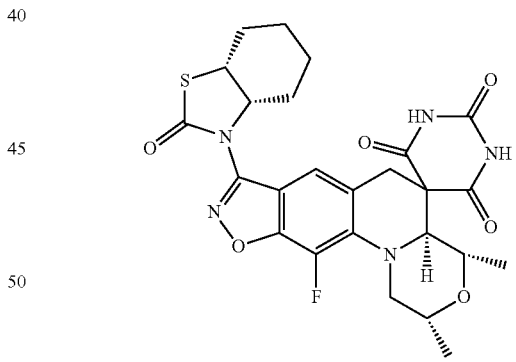

According to the synthesis method of compound 1, an intermediate I-8-23 (40 mg, 0.091 mmol) and barbituric acid (14 mg, 0.111 mmol) were used as raw materials to prepare 32 mg of white solid in a yield of 64%. $^1$H NMR (400 MHz, DMSO) δ 11.65 (s, 2H), 7.32 (s, 1H), 4.53-4.46 (m, 1H), 4.40 (dd, J=9.7, 4.7 Hz, 1H), 4.09 (d, J=12.8 Hz, 1H), 3.92 (d, J=8.8 Hz, 1H), 3.83-3.74 (m, 1H), 3.69-3.60 (m, 2H), 3.13-3.05 (m, 1H), 2.88 (d, J=14.3 Hz, 1H), 2.19-2.10 (m, 1H), 1.99-1.92 (m, 2H), 1.88-1.77 (m, 1H), 1.57-1.47 (m, 3H), 1.36-1.26 (m, 1H), 1.13 (d, J=6.1 Hz, 3H), 0.88 (d, J=6.3 Hz, 3H); $^{13}$C NMR (126 MHz, DMSO) δ 171.53, 171.47, 168.24, 153.77 (d, J=13.0 Hz), 153.40, 150.03, 135.28, 133.73 (d, J=239.3 Hz), 123.21, 117.90, 108.07, 72.61, 72.14, 64.88, 61.83, 56.76 (d, J=9.3 Hz), 53.27, 45.39, 38.95, 27.53, 26.06, 21.75, 20.97, 18.64, 18.60; MS (ESI) m/z: [(M−1)⁻, 542.2].

Example 24: (2R,4S,4aS)-11-fluoro-2,4-dimethyl-8-((3aR,6aS)-2-oxohexahydrobenzo[d]thiazol-3(2H)-yl)-1,2,4,4a-tetrahydro-2'H,6H-spiro[isoxazole[4,5-g][1,4]oxazine[4,3-a]quinoline-5,5'-pyrimidine]-2',4',6'(1'H,3'H)-trione (Compound 24)

(a) (1R,2R)-2-((5-(1,3-dioxolan-2-yl)-6,7-difluorobenzo[d]isoxazol-3-yl)amino))cyclohexanol (I-3-24)

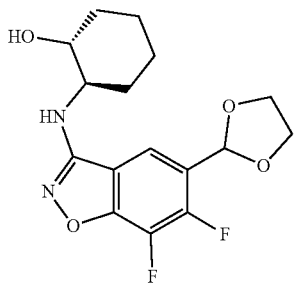 [SMILES: O[C@@H]1CCCC[C@H]1Nc1noc2c(F)c(F)c(C3OCCO3)cc12]

According to the synthesis method of intermediate I-3-1, an intermediate A (1.100 g, 4.450 mmol), N-chlorosuccinimide (713 mg, 5.340 mmol), (1R,2R)-2-aminocyclohexanol hydrochloride (1.000 g, 6.550 mmol), triethylamine (1.547 ml, 11.130 mmol) and cesium carbonate (7.260 g, 22.26 mmol) were used as raw materials to prepare 1.000 g of white solid in a yield of 66%. ¹H NMR (400 MHz, DMSO) δ 8.01 (d, J=4.6 Hz, 1H), 7.11 (d, J=7.5 Hz, 1H), 6.09 (s, 1H), 4.71 (d, J=5.1 Hz, 11H), 4.12-4.00 (m, 4H), 3.44 (td, J=9.2, 4.9 Hz, 11H), 3.30-3.20 (m, 1H), 2.15-2.06 (m, 1H), 1.97-1.88 (m, 1H), 1.71-1.59 (m, 2H), 1.34-1.16 (m, 4H).

(b) S-((1S,2R)-2-((5-(1,3-dioxolan-2-yl)-6,7-difluorobenzo[d]isoxazol-3-yl)amino)cyclohexyl)acetylthio (I-4-24)

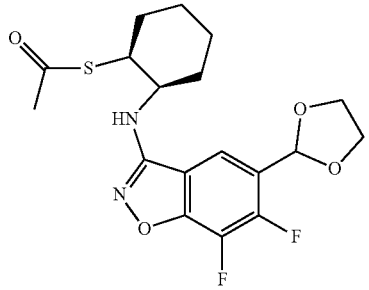 [SMILES: CC(=O)S[C@H]1CCCC[C@H]1Nc1noc2c(F)c(F)c(C3OCCO3)cc12]

According to the synthesis method of intermediate I-4-1, an intermediate I-3-24 (1.000 g, 2.940 mmol), triphenylphosphine (1.696 g, 6.460 mmol), diisopropyl azodicarboxylate (1.273 ml, 6.460 mmol) and thioacetic acid (0.460 ml, 6.460 mmol) were used as raw materials to prepare 195 mg of white solid in a yield of 17%. ¹H NMR (400 MHz, CDCl₃) δ 7.42 (dd, J=5.4, 1.0 Hz, 11H), 6.10 (s, 1H), 4.74 (d, J=6.6 Hz, 11H), 4.31-4.27 (m, 11H), 4.20-4.09 (m, 4H), 4.04-3.98 (m, 1H), 2.38 (s, 3H), 2.12-1.93 (m, 4H), 1.80-1.61 (m, 4H).

(c) (3aR,6aS)-3-(5-(1,3-dioxolan-2-yl)-6,7-difluorobenzo[d]isoxazol-3-yl)hexahydrobenzo[d]thiazol-2(3H)-one (I-6-24)

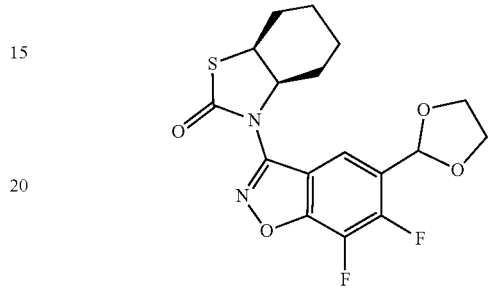

According to the synthesis method of intermediate I-6-1, an intermediate I-4-24 (93 mg, 0.233 mmol), sodium hydroxide (18 mg, 0.466 mmol), dithiothreitol (36 mg, 0.233 mmol), N,N-carbonyldiimidazole (75 mg, 0.466 mmol), and 4-dimethylaminopyridine (28 mg, 0.233 mmol) were used as raw materials to prepare 55 mg of colorless oil in a yield of 62%. ¹H NMR (400 MHz, CDCl₃) δ 8.11 (dd, J=5.9, 1.7 Hz, 1H), 6.15 (s, 1H), 4.57-4.50 (m, 1H), 4.38 (dd, J=8.9, 4.5 Hz, 1H), 4.23-4.06 (m, 4H), 2.45 (d, J=13.0 Hz, 1H), 2.14-1.91 (m, 4H), 1.83-1.61 (m, 4H), 1.38-1.32 (m, 2H).

(d) 6,7-difluoro-3-((3aR,6aS)-2-oxohexahydrobenzo[d]thiazol-3(2H)-yl)benzo[d]isoxazole-5-carbaldehyde (I-7-24)

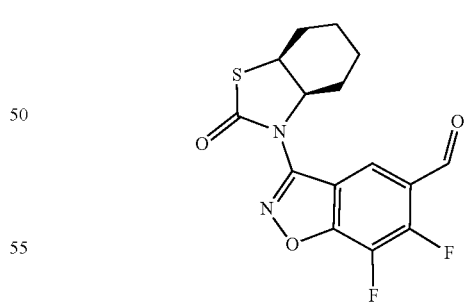

According to the synthesis method of intermediate I-7-1, an intermediate I-6-24 (50 mg, 0.131 mmol) and 6 M hydrochloric acid (3 ml) were used as raw materials to prepare 44 mg of white solid in a yield of 99%. ¹H NMR (400 MHz, CDCl₃) δ 10.30 (s, 1H), 8.55 (dd, J=5.8, 1.8 Hz, 1H), 4.58-4.52 (m, 1H), 4.40 (dd, J=8.7, 4.9 Hz, 1H), 2.51-2.43 (m, 1H), 2.16-2.08 (m, 1H), 2.07-1.92 (m, 2H), 1.84-1.76 (m, 1H), 1.76-1.63 (m, 2H), 1.39-1.32 (m, 2H).

(e) 6-((2R,6R)-2,6-dimethylmorpholine)-7-fluoro-3-((3aR,6aS)-2-hexahydrobenzo[d]thiazol-3(2H)-yl)benzo[d]isoxazole-5-carbaldehyde (I-8-24)

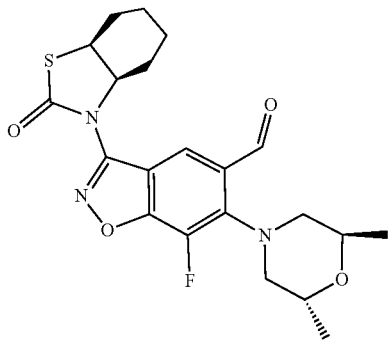 [SMILES: C[C@@H]1CN(c2c(C=O)cc3c(N4C(=O)S[C@H]5CCCC[C@H]54)noc3c2F)C[C@@H](C)O1]

According to the synthesis method of intermediate I-8-1, an intermediate I-7-24 (65 mg, 0.192 mmol), 2R,6R-dimethylmorpholine (0.039 ml, 0.288 mmol), and N,N-diisopropyl ethylamine (0.095 ml, 0.576 mmol) were used as raw materials to prepare 44 mg of white solid in a yield of 53%. $^1$H NMR (400 MHz, CDCl$_3$) δ 10.41 (s, 1H), 8.42 (d, J=1.1 Hz, 1H), 4.56-4.50 (m, 11H), 4.39-4.34 (m, 11H), 4.29-4.20 (m, 2H), 3.43 (d, J=11.9 Hz, 2H), 3.05 (dd, J=12.7, 5.0 Hz, 2H), 2.46-2.38 (m, 1H), 2.15-1.92 (m, 3H), 1.81-1.63 (m, 3H), 1.40-1.36 (m, 1H), 1.34 (d, J=6.4 Hz, 6H).

(f) (2R,4S,4aS)-11-fluoro-2,4-dimethyl-8-((3aR,6aS)-2-oxohexahydrobenzo[d]thiazol-3(2H)-yl)-1,2,4,4a-tetrahydro-2'H,6H-spiro[isoxazole[4,5-g][1,4]oxazine[4,3-a]quinoline-5,5'-pyrimidine]-2',4',6'(1'H,3'H)-trione (Compound 24)

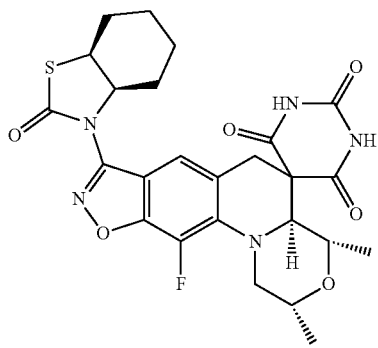

According to the synthesis method of compound 1, an intermediate I-8-24 (40 mg, 0.091 mmol) and barbituric acid (14 mg, 0.111 mmol) were used as raw materials to prepare 30 mg of white solid in a yield of 60%. $^1$H NMR (400 MHz, DMSO) δ 11.85 (s, 1H), 11.48 (s, 1H), 7.30 (s, 1H), 4.52-4.43 (m, 2H), 4.10 (d, J=13.2 Hz, 11H), 3.94 (d, J=8.9 Hz, 11H), 3.84-3.74 (m, 1H), 3.71-3.61 (m, 2H), 3.16-3.06 (m, 1H), 2.92 (d, J=13.8 Hz, 1H), 2.29-2.19 (m, 1H), 1.99-1.88 (m, 2H), 1.87-1.74 (m, 1H), 1.64-1.45 (m, 3H), 1.36-1.27 (m, 1H), 1.14 (d, J=6.1 Hz, 3H), 0.89 (d, J=6.3 Hz, 3H); $^{13}$C NMR (126 MHz, DMSO) δ 171.37, 171.35, 168.11, 153.72 (d, J=12.9 Hz), 153.51, 149.93, 135.36, 133.88 (d, J=239.4 Hz), 123.17, 117.91, 108.08, 72.57, 72.16, 64.83, 62.13, 56.77 (d, J=9.6 Hz), 53.39, 45.57, 38.93, 27.12, 26.09, 21.97, 20.68, 18.64, 18.60; MS (ESI) m/z: [(M−1)$^-$, 542.2].

Example 25: (2R,4S,4aS)-11-fluoro-2,4-dimethyl-8-(5-methylene-2-oxothiazol-3-yl)-1,2,4,4a-tetrahydro-2'H,6H-spiro[isoxazole[4,5-g][1,4]oxazine[4,3-a]quinoline-5,5'-pyrimidine]-2',4',6'(1'H,3'H)-trione (Compound 25)

(a) (R)-3-(5-(1,3-dioxolan-2-yl)-6,7-difluorobenzo[d]isoxazol-3-yl)-5-(iodomethyl)thiazol-2-one (I-1-25)

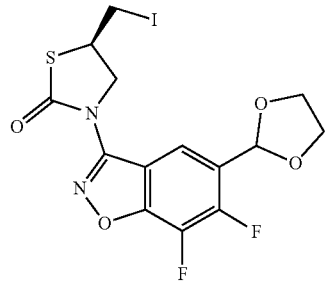 [SMILES: O=C1S[C@@H](CI)CN1c1noc2c(F)c(F)c(C3OCCO3)cc12]

At room temperature, an intermediate I-1-20 (100 mg, 0.229 mmol) was added into 3 ml of N,N-dimethylformamide. Under the protection of argon, sodium iodide (343 mg, 2.291 mmol) was added and the mixture was warmed to 60° C. and reacted for 8 hours. TLC detection showed that the reaction was completed. Water was added and the mixture was extracted with ethyl acetate. The combined organic layers were washed with water and saturated brine, dried over anhydrous sodium sulfate, concentrated under reduced pressure and purified by column chromatography [petroleum ether:ethyl acetate=5:1] to obtain 105 mg of colorless oil in a yield of 98%. $^1$H NMR (400 MHz, CDCl$_3$) δ 8.13 (dd, J=5.9, 1.5 Hz, 1H), 6.13 (s, 1H), 4.45 (dd, J=11.5, 7.0 Hz, 1H), 4.25 (dd, J=11.5, 4.0 Hz, 1H), 4.22-4.04 (m, 5H), 3.60-3.48 (m, 2H).

(b) 3-(5-(1,3-dioxolan-2-yl)-6,7-difluorobenzo[d]isoxazol-3-yl)-5-methylenethiazol-2-one (I-2-25)

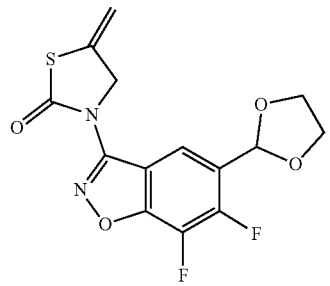 [SMILES: C=C1CN(c2noc3c(F)c(F)c(C4OCCO4)cc23)C(=O)S1]

At room temperature, the intermediate I-1-25 (105 mg, 0.229 mmol) was dissolved in THF, and 1,8-diazabicycloundec-7-ene (0.171 ml, 1.146 mmol) was added. Under the protection of argon, the reaction was performed under ultrasonic condition for 5 minutes, and TLC detection showed that the reaction was completed. The mixture was directly concentrated under reduced pressure and purified by column chromatography [petroleum ether:ethyl acetate=5:1] to obtain 65 mg of white solid in a yield of 83%. $^1$H NMR (400 MHz, CDCl$_3$) δ 8.30 (dd, J=6.0, 1.8 Hz, 1H), 6.16 (s, 1H), 5.48 (q, J=2.2 Hz, 1H), 5.34 (q, J=2.4 Hz, 1H), 4.96 (t, J=2.3 Hz, 2H), 4.24-4.06 (m, 4H).

(c) 6,7-fluoro-3-(5-methylene-2-oxothiazol-3-yl)benzo[d]isoxazole-5-carbaldehyde (I-3-25)

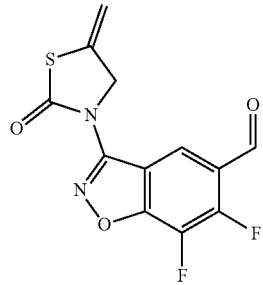 [SMILES: C=C1CN(c2noc3c(F)c(F)c(C=O)cc23)C(=O)S1]

According to the synthesis method of intermediate I-7-1, an intermediate I-2-25 (110 mg, 0.323 mmol) and 6 M hydrochloric acid (3 ml) were used as raw materials to prepare 77 mg of white solid in a yield of 80%. $^1$H NMR (400 MHz, CDCl$_3$) δ 10.31 (s, 1H), 8.75 (dd, J=5.8, 1.8 Hz, 1H), 5.51 (dd, J=4.4, 2.2 Hz, 1H), 5.37 (dd, J=4.7, 2.3 Hz, 1H), 4.97 (t, J=2.3 Hz, 2H).

(d) 6-((2R,6R)-2,6-dimethylmorpholine)-7-fluoro-3-(5-methylene-2-oxothiazol-3-yl)benzo[d]isoxazole-5-carbaldehyde (I-4-25)

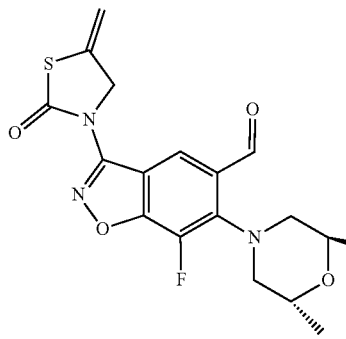

According to the synthesis method of intermediate I-8-1, an intermediate I-3-25 (72 mg, 0.243 mmol), 2R,6R-dimethylmorpholine (0.045 ml, 0.362 mmol), and N,N-diisopropyl ethylamine (0.120 ml, 0.729 mmol) were used as raw materials to prepare 73 mg of white solid in a yield of 77%. $^1$H NMR (400 MHz, CDCl$_3$) δ 10.39 (s, 1H), 8.59 (d, J=0.8 Hz, 1H), 5.49 (q, J=2.1 Hz, 1H), 5.35 (dd, J=4.7, 2.4 Hz, 1H), 4.95 (t, J=2.3 Hz, 2H), 4.30-4.21 (m, 2H), 3.44 (d, J=12.0 Hz, 2H), 3.06 (dd, J=11.4, 5.2 Hz, 2H), 1.34 (d, J=6.4 Hz, 6H).

(e) (2R,4S,4aS)-11-fluoro-2,4-dimethyl-8-(5-methylene-2-oxothiazol-3-yl)-1,2,4,4a-tetrahydro-2'H,6H-spiro[isoxazole[4,5-g][1,4]oxazine[4,3-a]quinoline-5,5'-pyrimidine]-2',4',6'(1'H, 3'H)-trione (Compound 25)

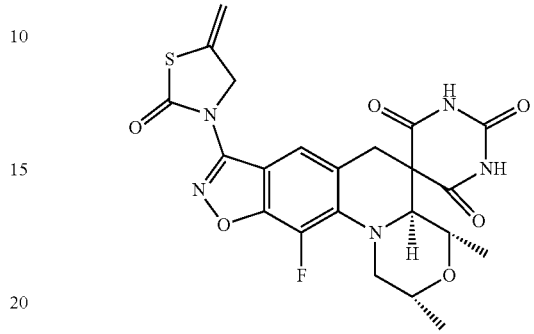

According to the synthesis method of compound 1, an intermediate I-4-25 (69 mg, 0.176 mmol) and barbituric acid (25 mg, 0.194 mmol) were used as raw materials to prepare 10 mg of white solid in a yield of 11%. $^1$H NMR (400 MHz, DMSO) δ 11.84 (s, 1H), 11.48 (s, 1H), 7.52 (s, 1H), 5.55 (d, J=1.7 Hz, 1H), 5.42 (d, J=1.8 Hz, 1H), 5.02-4.91 (m, 2H), 4.11 (d, J=12.8 Hz, 1H), 3.94 (d, J=8.8 Hz, 1H), 3.84-3.75 (m, 1H), 3.72-3.62 (m, 2H), 3.16-3.06 (m, 1H), 2.92 (d, J=14.0 Hz, 1H), 1.15 (d, J=6.1 Hz, 3H), 0.89 (d, J=6.3 Hz, 3H); $^{13}$C NMR (126 MHz, DMSO) δ 171.37, 168.66, 168.12, 154.17 (d, J=13.0 Hz), 153.09, 149.94, 135.32, 133.91, 133.72 (d, J=239.1 Hz), 122.92, 118.72, 109.39, 106.96, 72.59, 72.13, 64.85, 56.73 (d, J=9.5 Hz), 55.08, 53.33, 39.00, 18.63, 18.60; MS(EI) m/z: [M$^+$, 501].

Example 26

In Vitro Antibacterial Activity Assay

1. Strains Used in the Experiments

The following strains isolated in clinic were used in antibacterial activity screening in vitro: five strains of methicillin-resistant *Staphylococcus aureus* or MRSA, five strains of methicillin-sensitive *Staphylococcus aureus* or MSSA, five strains of methicillin-resistant *Staphylococcus epidermidis* or MRSE, five strains of methicillin-sensitive *Staphylococcus epidermidis* or MSSE, three strains of penicillin-resistant *Streptococcus pneumoniae* or PRSP, and three strains of *Streptococcus pyogenes*.

The above strains were clinically isolated pathogenic bacteria collected in Sichuan and Beijing in December 2015. They were identified by the collection unit via a VITEK-60 automatic microbiological identification instrument, and then re-identified by conventional methods in the laboratory. Before the experiment, each strain was purified by a single colony on an agar plate, and the cells freshly cultured at 37° C. overnight were appropriately diluted for the experiment. Quality control strain was *Staphylococcus aureus* ATCC25923 purchased from the Clinical Testing Center of the Ministry of Health of the People's Republic of China.

2. Medium and Culture Condition

Medium: MH (Mueller-Hinton, hydrolyzed casein) broth (OXOID);

Culture condition: Incubate at 35-37° C. for 16-18 h.

3. Experimental Method

The MIC value of each test sample for the tested strain was determined by micro broth dilution method recommended by Performance Standards for Antimicrobial Susceptibility Testing (Twenty-Third Informational Supplement; M02-A11, M07-A9 and M11-A8, 2013) of American Clinical and Laboratory Standards Institute (CLSI).

After diluting each test sample to different concentrations in MH broth, 100 µl of each sample solution at different concentrations was pipetted into a sterilized 96-well polystyrene plate. In the first to twelfth wells, the drug solution was added, and the final drug concentrations in each well were 64, 32, 16, 8, 4, 2, 1, 0.5, 0.25, 0.125, 0.06, and 0.03 mg/L. The well without drug and without bacteria was set as blank control well. The well with bacteria and without drug was set as a bacterial growth control well.

The test bacterial solution was adjusted with physiological saline to a bacterial suspension equivalent to 0.5 Maisson turbidity standard, and diluted 1:100 with MH broth. The drug solution was added so that the final concentration of the bacterial solution was about $10^4$ CFU/ml; then 100 µl of bacterial solution was pipetted into the above wells (the total volume in each well was 200 µl). The plate was sealed and placed in a 35-37° C. incubator for 18-20 h, and then the results were determined. The OD600 value was measured with a microplate reader, and the minimum drug concentration that completely inhibited bacterial growth in the small well was minimum inhibitory concentration (MIC). When *Streptococcus pneumoniae* was tested, sterile defibrillated sheep blood was added into the Colombian broth culture medium at a final concentration of 5% and cultivation was conducted in a 5% $CO_2$ and 35-37° C. incubator for 18-20 hours.

The results of the in vitro antibacterial activity are shown in Table 1.

TABLE 1

In vitro antibacterial activity test results of some compounds of the present invention

| | MIC(µg/ml) | | | | | |
|---|---|---|---|---|---|---|
| Compound No. | MRSA[a] (5) | MSSA[b] (5) | MRSE[c] (5) | MSSE[d] (5) | PRSP[e] (3) | Spy[f] (3) |
| 1 | <0.03-0.06 | <0.03 | <0.03 | <0.03 | <0.03 | <0.03 |
| 2 | <0.03-0.25 | <0.03-0.06 | <0.03 | <0.03 | <0.03 | <0.03 |
| 3 | 0.03-0.25 | <0.03-0.125 | 0.03-0.06 | <0.03-0.06 | <0.03-0.03 | <0.03 |
| 4 | 0.03-0.5 | 0.25-0.5 | 0.03-0.125 | 0.03-0.125 | 0.25-1 | 0.125-0.25 |
| 5 | 0.03-0.25 | 0.25-0.5 | 0.06-0.25 | 0.03-0.125 | 0.125-1 | 0.125-0.25 |
| 6 | <0.03-1 | 0.06-0.125 | <0.03-0.06 | <0.03 | 0.06-0.25 | <0.03-0.06 |
| 8 | 0.03-0.5 | 0.03-0.25 | <0.03-0.03 | <0.03-0.125 | <0.03-0.5 | 0.25-0.5 |
| 10 | 0.25-0.5 | 0.06-0.25 | 0.03-0.125 | 0.03-0.25 | 0.125 | 0.125-1 |
| 16 | <0.03-0.06 | <0.03-0.06 | <0.03 | <0.03 | <0.03-0.06 | <0.03 |
| 19 | <0.03 | <0.03 | <0.03 | <0.03-0.06 | <0.03-0.06 | <0.03 |
| 21 | <0.03-0.125 | <0.03-0.125 | <0.03-0.06 | <0.03-0.125 | <0.03-0.125 | <0.03-0.125 |
| 25 | <0.03 | <0.03 | <0.03 | <0.03 | <0.03 | <0.03 |
| AZD0914 | 0.06-1 | 0.125-0.25 | 0.06-0.25 | 0.06-0.25 | 0.25-1 | 0.25-0.5 |
| levofloxacin | 16->64 | 4->64 | 4->64 | 0.5-4 | 1 | 0.5-1 |

[a]Methicillin resistant *S. aureus*.
[b]Methicillin sensitive *S. aureus*.
[c]Methicillin resistant *S. epidermidis*.
[d]Methicillin sensitive *S. epidermidis*.
[e]Penicillin resistant *S. pneumoniae*.
[f]*S. pyogenes*.

It can be seen from Table 1 that the representative compounds of the present invention have very good antibacterial activities in vitro, which are much better than the existing positive control drug AZD0914, and overcome the disadvantage of lacking strong antibacterial activity of AZD0914.

In particular, compound 1, compound 2, compound 3, compound 16, compound 19, and compound 25 have much better in vitro antibacterial activities against MRSA, MSSA, MRSE, MSSE, PRSP, and Spy than the control drug AZD0914, which are about 8 times of the activity of AZD0914. The in vitro antibacterial activities of compound 6, compound 8, compound 10 and compound 21 are about 2-4 times of the activity of AZD0914.

The representative compounds of the present invention still have strong antibacterial activities against levofloxacin-resistant *Staphylococcus aureus* and *Staphylococcus epidermidis*, indicating that the compounds of the present invention have no cross-resistance with fluoroquinolones.

Example 27

In Vivo Pharmacokinetics Test in Mice

Healthy female CD-1 mice were randomly divided into five groups and each group comprised three mice. The tested compound was administered orally. The specific regimen was shown in Table 2 below.

TABLE 2

The administration regimen for mice in pharmacokinetic experiment in vivo

| group | animal female | test sample | dosage (mg/kg) | concentration* (mg/ml) | volume (ml/kg) | sample collection | way | solvent |
|---|---|---|---|---|---|---|---|---|
| G1 | three mice | compound 1 | 10.0 | 1.00 | 10.0 | plasma | PO (oral) | 100% (0.5% sodium methyl cellulose) |
| G2 | three mice | compound 2 | 10.0 | 1.00 | 10.0 | plasma | PO | |
| G3 | three mice | compound 3 | 10.0 | 1.00 | 10.0 | plasma | PO | |
| G4 | three mice | compound 8 | 10.0 | 1.00 | 10.0 | plasma | PO | |
| G5 | three mice | compound 16 | 10.0 | 1.00 | 10.0 | plasma | PO | |
| G6 | three mice | AZD0914 | 10.0 | 1.00 | 10.0 | plasma | PO | |

0.030 mL of blood was taken from the orbit of each animal each time and anticoagulated with $EDTAK_2$. The collection time was as follows. PO group: 15 m, 30 mi, 1 h, 2 h, 4 h, 6 h, 8 h, and 24 h after administration of the test compound. The collected blood samples were placed on ice and centrifuged within 30 minutes to separate the plasma (centrifugation conditions: 5000 rpm, 10 minutes, room temperature). The samples were stored at −80° C. before analysis. The experimental results are shown in Table 3.

TABLE 3 pharmacokinetic data in orally administered mice

| | $t_{1/2}$ (h) | $T_{max}$ (h) | $C_{max}$ (ng·mL$^{-1}$) | $AUC_{0 \to t}$ (h·ng·mL$^{-1}$) | MRT (h) |
|---|---|---|---|---|---|
| compound 1 | 2.90 ± 1.72 | 1.33 ± 0.577 | 1548 ± 52 (about 8 times) | 7334 ± 943 (about 10 times) | 3.70 ± 0.95 |
| compound 2 | 6.20 ± 1.40 | 2.67 ± 1.15 | 2576 ± 713 (about 14 times) | 24241 ± 5642 (about 32 times) | 8.94 ± 2.15 |
| compound 3 | 2.70 ± 0.143 | 0.583 ± 0.382 | 2188 ± 223 (about 12 times) | 12034 ± 2835 (about 16 times) | 4.85 ± 0.99 |
| compound 8 | 2.51 ± 0.08 | 0.583 ± 0.382 | 2051 ± 88 (about 11 times) | 8240 ± 940 (about 11 times) | 3.72 ± 0.76 |
| compound 16 | 1.59 ± 0.495 | 1.17 ± 0.764 | 2376 ± 411 (about 13 times) | 8057 ± 1469 (about 11 times) | 3.45 ± 0.788 |
| AZD0914 | 3.41 ± 0.944 | 0.583 ± 0.382 | 183 ± 134 | 748 ± 215 | 7.06 ± 2.92 |

The excellent metabolic properties are the key indicators of the compound drugability. The pharmacokinetic experiments have proven that the compounds of the present invention have ideal metabolic characteristics. Compared with the positive control drug AZD0914, the drug exposure is greatly improved, and the comprehensive metabolic characteristics are far superior to the positive control drug AZD0914.

The maximum blood concentration $C_{max}$ of the compound of the present invention is 8-14 times of that of the positive control drug AZD0914, and the drug exposure $AUC_{0 \to t}$ is 10-32 times of that of the positive control drug AZD0914.

Example 28

In Vivo Pharmacokinetic Test of Compounds of the Present Invention in Rats

Nine SD rats were randomly divided into three groups and each group comprised three mice. The specific regimen was shown in Table 4 below.

0.100 mL of blood was taken from the orbit of each animal each time and anticoagulated with $EDTAK_2$. The collection time was as follows. (1) PO group (10.0 mg/kg): 15 min, 30 min, 1 h, 2 h, 4 h, 6 h, 8 h, 24 h after administration of the test compound; PO group (100 mg/kg): 15 min, 30 min 1 h, 2 h, 4 h, 6 h, 8 h, 10 h, 24 h, 36 h, 48 h; (2) IV group: 5 min, 15 min, 30 min, 1 h, 2 h, 4 h, 6 h, 8 h, 24 h after administration of the test compound. The collected blood samples were placed on ice and centrifuged within 30 minutes to separate the plasma (centrifugation conditions: 5000 rpm, 10 minutes, 4° C.). The samples were stored at −80° C. before analysis. The experimental results are shown in Table 5.

TABLE 4

Administration regimen

| group | animal male | Test compound | dosage (mg/kg) | concentration* (mg/mL) | volume (mL/kg) | sample collection | administration route | solvent |
|---|---|---|---|---|---|---|---|---|
| G1 | three rats | Compound 2 | 10.0 | 2.00 | 5.00 | plasma | IV | 5% DMSO (dimethyl sulfoxide) + 1% Solutol (solubilizer) + 10% EtOH + 75% saline |
| G2 | three rats | | 10.0 | 0.667 | 15.0 | plasma | PO | 5% DMSO + 95% (0.5% sodium methyl cellulose) |
| G3 | three rats | | 100 | 6.67 | 15.0 | plasma | PO | |

TABLE 5

Main pharmacokinetic parameters of SD rats after oral (PO) or intravenous (IV) administration of Compound 2

| Dose: IV/PO (mg/kg) | 10 mg/kg | 100 mg/kg |
|---|---|---|
| $AUC_{0-t}$ (h · ng · mL$^{-1}$, PO) | 46598 ± 7538 | 509230 ± 65872 |
| $C_{max}$ (ng · mL$^{-1}$, PO) | 4430 ± 1250 | 32069 ± 7934 |
| $T_{max}$ (h, PO) | 5.33 ± 1.15 | 5.33 ± 1.15 |
| $T_{1/2}$ (h, PO) | 4.38 ± 1.21 | 4.19 ± 0.23 |
| MRT (h, PO) | 7.54 ± 0.773 | 11.1 ± 2.11 |
| % F | 52.0 ± 8.41 | 55.1 ± 7.1 |
| $AUC_{0-t}$ (h · ng · mL$^{-1}$, IV) | 89577 ± 9072 | ND |
| $T_{1/2}$ (h, IV) | 4.93 ± 0.844 | ND |
| Cl(ml · kg$^{-1}$ · min$^{-1}$, IV) | 1.82 ± 0.214 | ND |
| Vdss (L · kg$^{-1}$, IV) | 0.675 ± 0.0578 | ND |
| MRT (h, IV) | 6.22 ± 0.601 | ND |

It can be seen from Table 5 that after the compound of the present invention is administered orally at doses of 10 mg/kg and 100 mg/kg, respectively, the drug exposure and the dose show a good linear correlation, indicating that the compound of the present invention is well absorbed.

Example 29

In Vivo Antibacterial Activity of Compounds of the Present Invention Against MRSA 1. Test Strain Based on the results of the in vitro test, the clinically isolated methicillin-resistant *Staphylococcus aureus* MRSA15-3 (see Table 6 below) was selected as a candidate test strain for in vivo protection experiments.

TABLE 6

In vitro antibacterial activity of the compound of the present invention and the control drug against *Staphylococcus aureus* MRSA15-3-MIC (mg/L)

| | MIC (mg/L) | |
|---|---|---|
| Strain name | Compound 2 | AZD0914 |
| *Staphylococcus aureus* MRSA15-3 | <0.03 | 0.125 |

2. Test Animal

Healthy Kunming mice: aged about 4 weeks, 18-22 g, half male and half male, SPF grade.

Expected number of mice used: 200 mice

3. Test Method for In Vivo Protection 3.1 Bacteria Liquid Preparation

One day before the infection of the test bacteria, 2-3 single colonies were picked, inoculated into 2 mL of MH broth, and incubated at 37° C. for 6 h. 0.1 ml of such bacterial solution was transferred to 10 mL of MH broth, and incubated at 37° C. for 18 h. This bacterial solution was the original bacterial stock solution. The bacterial stock solution was diluted in proportion with 5% dry yeast solution for future use (freshly prepared on the same day).

3.2 Minimum Lethal Dose (MLD) Test

Healthy Kunming mice, weighing 18 to 22 grams, were randomly divide into groups and each group comprised 5-10 mice, half male and half male. The above-mentioned bacterial solution with different dilution concentration were taken and injected into the mice intraperitoneally at a dose of 0.5 ml per 20 g mice weight. They were observed for 7-14 days after infection, and the death numbers of mice were recorded. The minimum dose of bacteria that causes 100% death of mice is the minimum lethal dose (MLD), which is used as the infectious bacteria dose in the in vivo protection test.

3.3 Preparation of Drug Solution and Route of Administration

Preparation of medicinal solution: the test drug was prepared with 0.5% sodium carboxymethyl cellulose and diluted to the required concentration solution for later use.

Route of administration: intragastric administration

Dosing volume: 0.5 ml/20 g BW (BW, body weight)

3.4 Grouping

With reference to relevant literature, the proposed dosage range of test compound was set to 20-2.5 mg/kg. The drug was accurately weighed and converted to the effective drug weight according to the potency. The drug was prepared with 0.5% sodium carboxymethyl cellulose into a solution having the required concentration, and the interval between dose groups was 1:0.5.

Grouping: AZD0914 group (20, 10, 5, 2.5 g·kg$^{-1}$), Compound 2 group (20, 10, 5, 2.5 g·kg$^{-1}$), infection control group, blank control group, 1-aminobenzotriazole (ABT) toxicity control.

3.5 Experimental Method of In Vivo Protection and Statistics of Results

The mice were fasted and given water for 18 hours before the test, and were randomly divided into groups according to body weight. Each group contained eight mice, half male and half female, and each mouse was injected intraperitoneally with the test bacteria solution with a dose of 0.5 ml per 20 g mouse body weight. 0.5 h and 4 h after infection, the mice were administered via intragastric administration according to the designed dose, 0.5 ml per 20 g mouse body weight. They were observed for 7-14 days and the death numbers of mice were recorded. Based on the death numbers of mice, half effective dose ED50 and 95% confidence limit were calculated by Bliss method using DAS1.0 software edited by Sun Ruiyuan, et al.

Since the mice metabolic clearance rate of the control drug AZD0914 was too high and the metabolic properties were not ideal, the mice in AZD0914 control group must be orally administered with a cytochrome P450 inhibitor, 1-aminobenzotriazole (ABT) at a dose of 50 mg/kg two hours before infection. After 12 hours, the mice were orally administered with 50 mg/kg ABT again. The mice in the compound group did not require oral administration of ABT.

The mice in the infection control group were only infected with bacteria and were not administered with the medicine, and the same volume of saline was administered via intragastric administration after infection. The mice in the blank control group were not infected with bacteria, the same volume of saline was administered via intraperitoneal injection, and the same volume of saline was administered via intragastric administration.

4. Test Results

The in vivo antibacterial activity test results of the systemic infection model are shown in Table 7.

TABLE 7

In vivo protective effect of the compounds of the present invention on *S. aureus* MRSA15-3 infected mice ($ED_{50}$)

| Drug | Administration route | $ED_{50}$ (95% confidence limit) (mg/kg) |
|---|---|---|
| Compound 2 | i.g. (intragastric administration) | 2.54 0.11-3.71 |
| AZD0914 | i.g. (intragastric administration) | 11.51 7.28-25.79 |

It can be seen from Table 7 that oral administration of Compound 2 of the present invention has a four-fold stronger in vivo protective effect on *S. aureus* MRSA15-3 infected mice than that of the positive control drug AZD0914, so that the effect is far superior to that of AZD0914.

In summary, the compounds of the present invention have better drugability than the existing positive control drug AZD0914, and are expected to become a better antibacterial drug.

All documents mentioned in the present invention are incorporated by reference in this application, as if each document was individually incorporated by reference. In addition, it should be understood that after reading the above-mentioned teaching content of the present invention, those skilled in the art can make various changes or modifications to the present invention, and these equivalent forms also fall within the scope defined by the appended claims of the present application.

We claim:

1. A compound represented by the general formula I, or an enantiomer, a diastereomer, a racemate and a mixture thereof, or a pharmaceutically acceptable salt thereof,

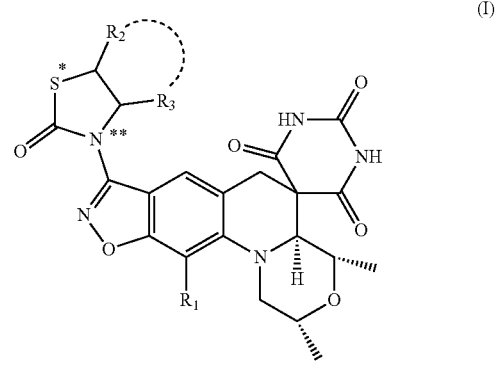

(I)

wherein, $R_1$ is hydrogen, halogen or cyano;

$R_2$ and $R_3$ are each independently hydrogen, phenyl, substituted or unsubstituted $C_1$-$C_6$ alkyl, or $=CH_2$, and the term "substituted" refers to a substitution with a substituent selected from the group consisting of $C_1$-$C_6$ alkoxy, phenyl, halogen, —$N_3$, —$S(O_2)C_1$-$C_6$ alkyl, —$NHCOC_1$-$C_6$ alkyl, —$CONHC_1$-$C_6$ alkyl, —$OR_4$, $C_1$-$C_6$ alkylthio, $C_2$-$C_6$ alkenyl, $C_2$-$C_6$ alkynyl; or $R_2$, $R_3$ and the attached carbon atoms together form a 4-7 membered aliphatic ring;

$R_4$ is hydrogen, or $C_1$-$C_6$ haloalkyl;

* and ** each independently represent a racemic, S-type or R-type.

2. The compound of claim 1, wherein $R_1$ is fluorine, chlorine or cyano.

3. The compound of claim 1, wherein $R_2$ is hydrogen, phenyl, substituted or unsubstituted $C_1$-$C_4$ alkyl, or $=CH_2$, and the term "substituted" refers to a substitution with a substituent selected from the group consisting of halogen, —$OR_4$, $C_1$-$C_4$ alkoxy, —$N_3$, —$NHCOC_1$-$C_4$ alkyl, —$S(O_2)$ $C_1$-$C_4$ alkyl; $R_4$ is hydrogen or $C_1$-$C_4$ haloalkyl;

$R_3$ is hydrogen, substituted or unsubstituted $C_1$-$C_4$ alkyl, or phenyl, wherein the term "substituted" refers to a substitution with a substituent selected from the group consisting of: phenyl;

or $R_2$ and $R_3$ together with the attached carbon atoms form a 5-6 membered aliphatic ring.

4. The compound of claim 1, wherein $R_2$ is hydrogen, phenyl, substituted or unsubstituted $C_1$-$C_3$ alkyl, or $=CH_2$, and the term "substituted" refers to a substitution with a substituent selected from the group consisting of fluorine, chlorine, —$OR_4$, $C_1$-$C_3$ alkoxy, —$N_3$, —$NHCOC_1$-$C_3$ alkyl, —$S(O_2)C_1$-$C_3$ alkyl; $R_4$ is hydrogen or trifluoromethyl;

$R_3$ is hydrogen, $C_1$-$C_3$ alkyl, phenyl, or benzyl;

or $R_2$ and $R_3$ together with the attached carbon atoms form a 5-6 membered aliphatic ring.

5. The compound of claim 1, wherein $R_4$ is hydrogen or trifluoromethyl.

6. The compound of claim 1, wherein the compound is:
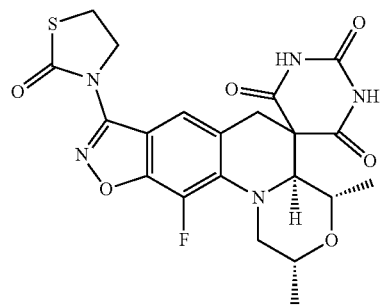
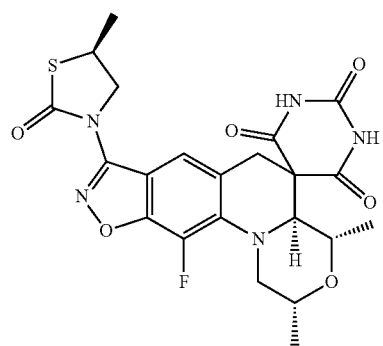
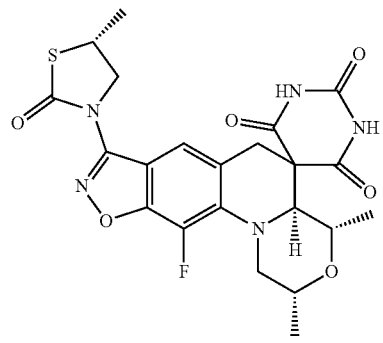
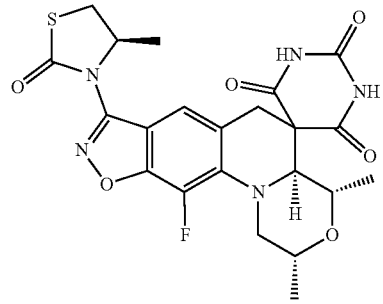
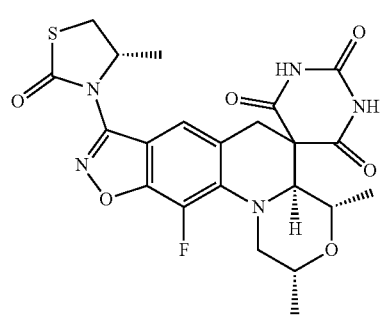
-continued
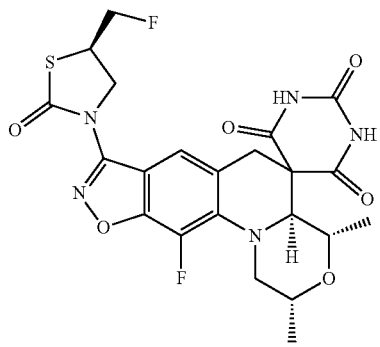
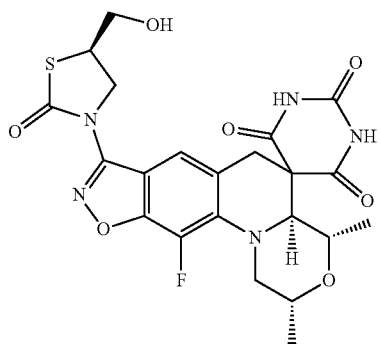
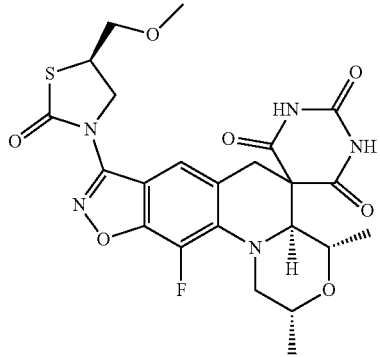
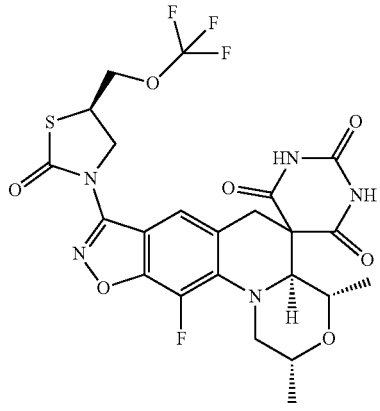

119
-continued
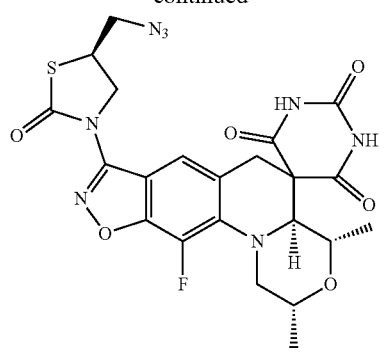
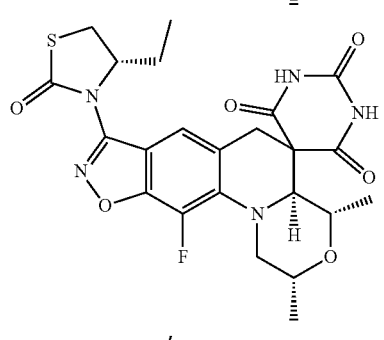
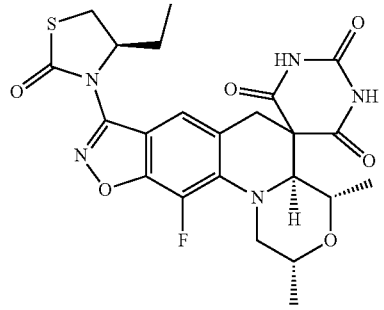
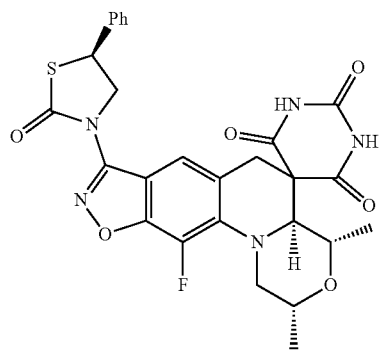
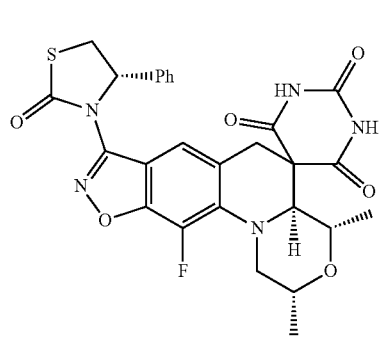
120
-continued
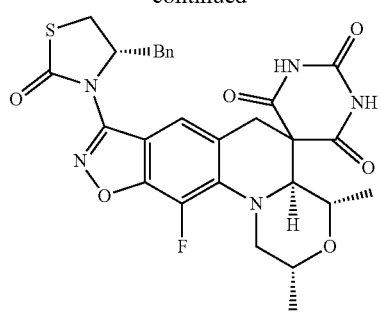
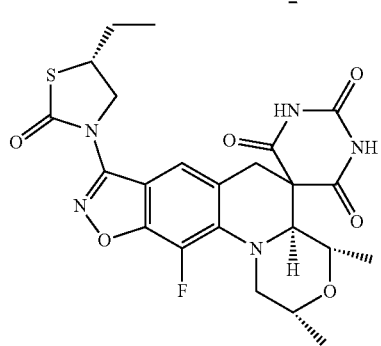
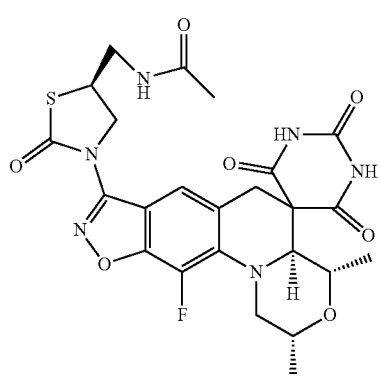
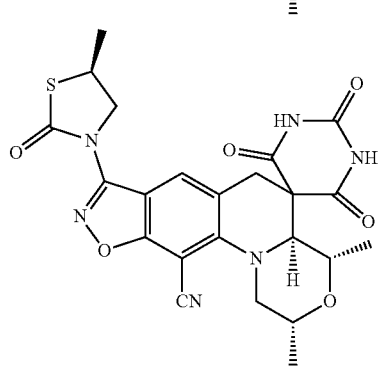
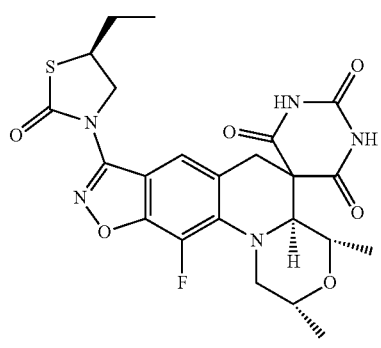

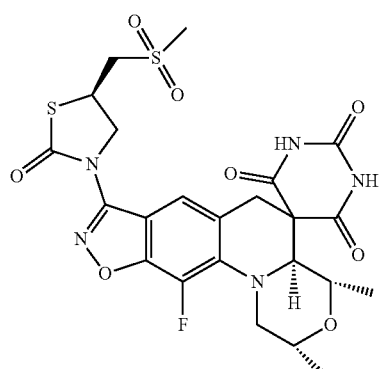
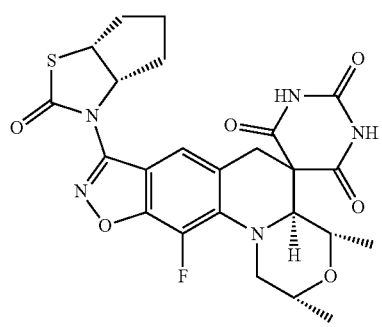
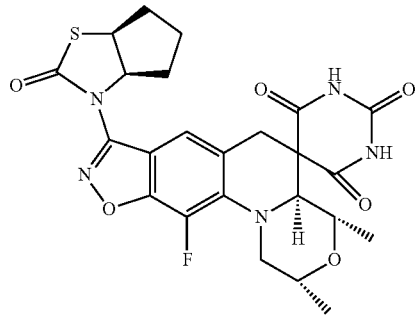
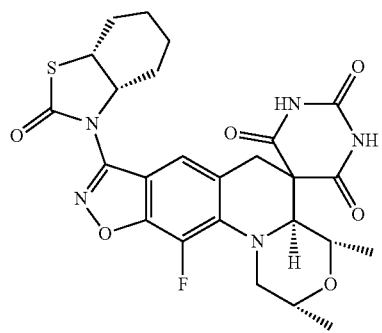
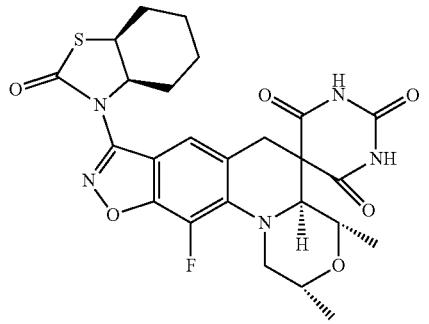
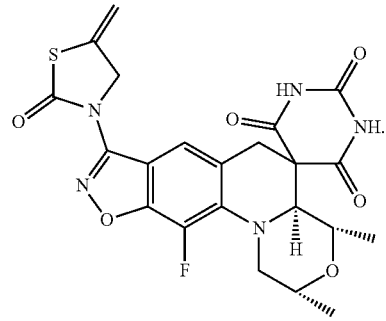
or
7. A pharmaceutical composition which comprises the compound or enantiomer, diastereomer, racemate and mixture thereof, or pharmaceutically acceptable salt thereof of claim 1; and
a pharmaceutically acceptable carrier or excipient.
8. A method for preparing the compound of claim 1 which comprises the following steps:
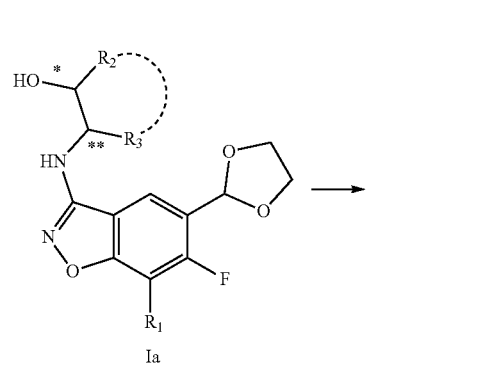
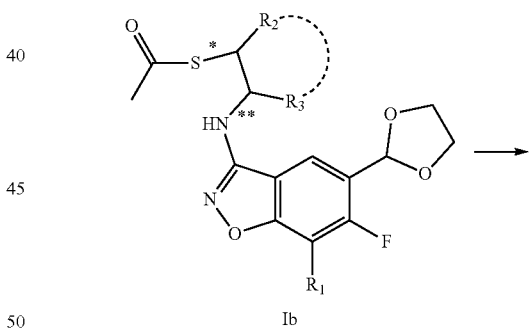
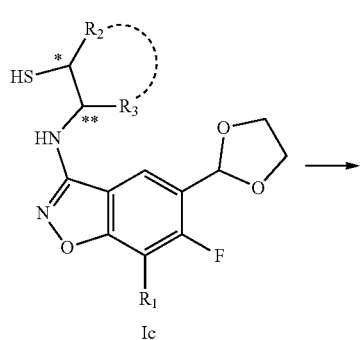

-continued

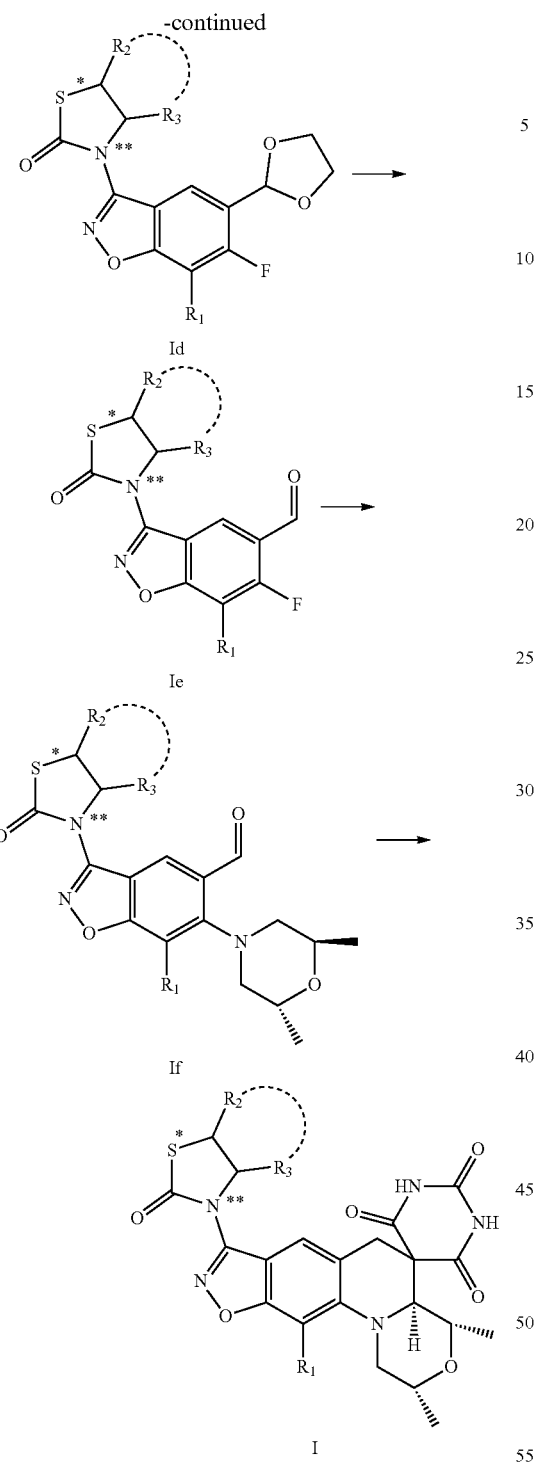

(i) subjecting an intermediate Ia to Mitsunobu reaction, thereby forming an intermediate Ib;
(ii) subjecting the intermediate Ib to hydrolysis reaction, thereby forming an intermediate Ic;
(iii) subjecting the intermediate Ic to nucleophilic substitution reaction, thereby forming an intermediate Id;
(iv) subjecting the intermediate Id to a deprotection reaction, thereby forming an intermediate Je;
(v) subjecting the intermediate Je to nucleophilic substitution reaction, thereby forming an intermediate If;
(vi) reacting the intermediate If with barbituric acid, thereby forming a compound represented by formula I, in each formula Ia, Ib, Ic, Id, Ie and If, $R_1$, $R_2$, and $R_3$ are defined as in claim 1.

9. An intermediate of a compound of formula I, which has a structure represented by Formula Ib, Ic, Id, Ie or If:

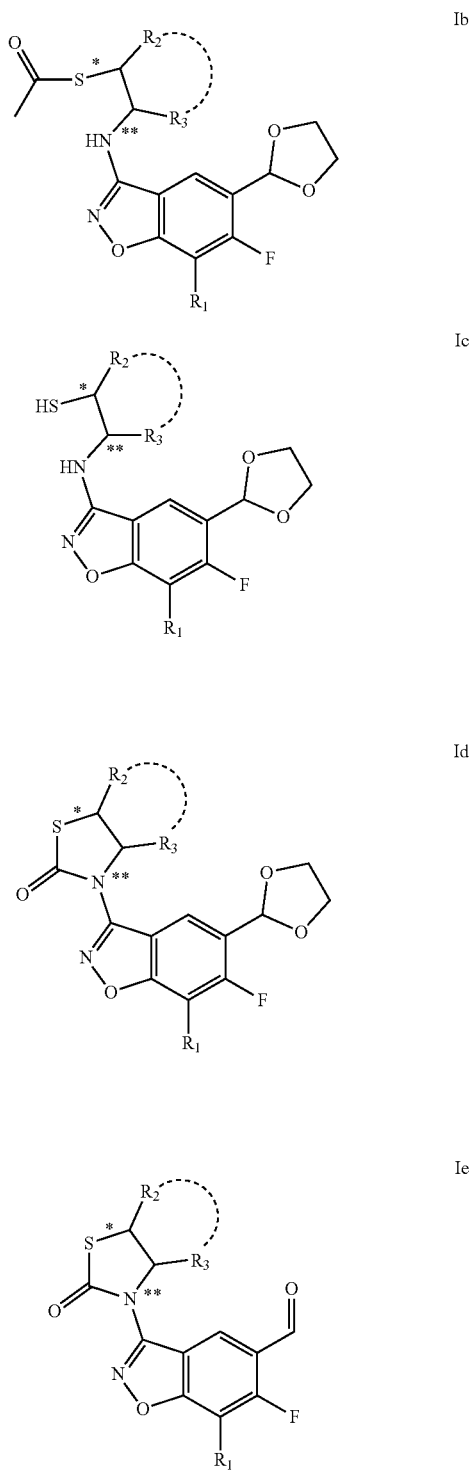

-continued
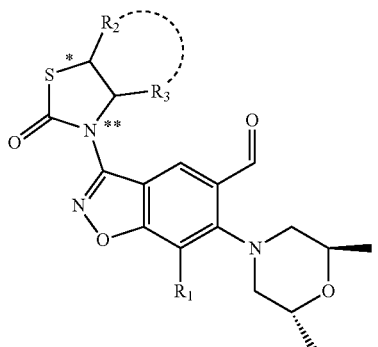
in each formula, *, , $R_1$, $R_2$, and $R_3$ are defined as in claim 1**.
10. A method for treating a bacterial infectious disease comprising administering the compound or enantiomer, diastereomer, racemate and mixture thereof, or pharmaceutically acceptable salt thereof of claim 1 to a subject in need thereof.
* * * * *